United States Patent
Ingber et al.

(10) Patent No.: US 10,472,612 B2
(45) Date of Patent: Nov. 12, 2019

(54) CELL CULTURE SYSTEM

(71) Applicant: PRESIDENT AND FELLOWS OF HARVARD COLLEGE, Cambridge, MA (US)

(72) Inventors: Donald E. Ingber, Boston, MA (US); Hyun Jung Kim, Brookline, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 357 days.

(21) Appl. No.: 15/388,171

(22) Filed: Dec. 22, 2016

(65) Prior Publication Data
US 2017/0101628 A1 Apr. 13, 2017

Related U.S. Application Data

(62) Division of application No. 14/001,838, filed as application No. PCT/US2012/026934 on Feb. 28, 2012.

(Continued)

(51) Int. Cl.
C12M 1/00 (2006.01)
C12M 3/00 (2006.01)
(Continued)

(52) U.S. Cl.
CPC ............ *C12N 5/0697* (2013.01); *C12M 21/08* (2013.01); *C12M 23/20* (2013.01); *C12M 23/26* (2013.01); *C12M 23/34* (2013.01); *C12M 23/38* (2013.01); *C12M 25/02* (2013.01); *C12M 27/02* (2013.01); *C12M 29/04* (2013.01); *C12M 29/06* (2013.01); *C12M 35/04* (2013.01); *C12M 35/08* (2013.01); *C12M 41/12* (2013.01); *C12M 41/26* (2013.01); *C12M 41/40* (2013.01); *C12M 41/44* (2013.01); *C12N 1/14* (2013.01); *C12N 1/20* (2013.01);
(Continued)

(58) Field of Classification Search
CPC ...... C12M 21/08; C12M 25/02; C12M 41/40; C12M 23/16; C12M 23/34; C12M 25/14; C12M 35/04

See application file for complete search history.

(56) References Cited

U.S. PATENT DOCUMENTS 3,300,386 A 1/1967 Aron-Brunetiere et al.
3,313,290 A 4/1967 Chance et al.
(Continued)

FOREIGN PATENT DOCUMENTS

WO 2004/059299 A1 7/2004
WO 2010/009307 A2 1/2010
(Continued)

OTHER PUBLICATIONS

US 6,465,252 B1, 10/2002, Toner et al. (withdrawn)
(Continued)

*Primary Examiner* — Nathan A Bowers
(74) *Attorney, Agent, or Firm* — Nixon Peabody LLP; David S. Resnick; Nicole D. Kling

(57) ABSTRACT

The embodiments of the invention described herein relate to systems and methods for culturing and/or maintaining intestinal cells, tissues and/or organoids in vitro. The cells, tissues and/or organoids cultured according to the methods and systems described herein can mimic or reproduce natural intestinal epithelial structures and behavior as well as support co-culture of intestinal microflora.

34 Claims, 21 Drawing Sheets

Related U.S. Application Data

(60) Provisional application No. 61/447,540, filed on Feb. 28, 2011.

(51) Int. Cl.
  *C12N 5/071* (2010.01)
  *C12M 1/12* (2006.01)
  *C12M 1/42* (2006.01)
  *C12N 1/14* (2006.01)
  *C12N 1/20* (2006.01)
  *C12M 1/06* (2006.01)
  *C12M 1/34* (2006.01)
  *C12N 5/074* (2010.01)

(52) U.S. Cl.
  CPC ........... *C12N 5/068* (2013.01); *C12N 5/0679* (2013.01); *C12N 5/0696* (2013.01)

(56) References Cited

U.S. PATENT DOCUMENTS

| | | |
|---|---|---|
| 3,722,504 A | 3/1973 | Sawyer |
| 3,941,662 A | 3/1976 | Munder et al. |
| 3,948,732 A | 4/1976 | Haddad et al. |
| 4,225,671 A | 9/1980 | Puchinger et al. |
| 4,436,824 A | 3/1984 | Bishop |
| 4,446,229 A | 5/1984 | Indech |
| 4,537,860 A | 8/1985 | Tolbert et al. |
| 4,610,878 A | 9/1986 | Wilson et al. |
| 4,629,686 A | 12/1986 | Gruenberg |
| 4,650,766 A | 3/1987 | Harm et al. |
| 4,673,650 A | 6/1987 | Braden |
| 4,720,462 A | 1/1988 | Rosenson |
| 4,734,372 A | 3/1988 | Rotman |
| 4,737,455 A | 4/1988 | De Baetselier |
| 4,749,654 A | 6/1988 | Karrer et al. |
| 4,835,102 A | 5/1989 | Bell et al. |
| 4,839,280 A | 6/1989 | Banes |
| 4,851,354 A | 7/1989 | Winston et al. |
| 4,929,542 A | 5/1990 | Risley |
| 4,940,853 A | 7/1990 | Vandenburgh |
| 5,002,890 A | 3/1991 | Morrison |
| 5,043,260 A | 8/1991 | Jauregui |
| 5,108,926 A | 4/1992 | Klebe |
| 5,160,490 A | 11/1992 | Naughton et al. |
| 5,217,899 A | 6/1993 | Shapiro et al. |
| 5,290,684 A | 3/1994 | Kelly |
| 5,316,905 A | 5/1994 | Mori et al. |
| 5,348,879 A | 9/1994 | Shapiro et al. |
| 5,486,335 A | 1/1996 | Wilding et al. |
| 5,496,697 A | 3/1996 | Parce et al. |
| 5,498,392 A | 3/1996 | Wilding et al. |
| 5,587,128 A | 12/1996 | Wilding et al. |
| 5,612,188 A | 3/1997 | Shuler et al. |
| 5,637,469 A | 6/1997 | Wilding et al. |
| 5,726,026 A | 3/1998 | Wilding et al. |
| 5,744,366 A | 4/1998 | Kricka et al. |
| 5,750,329 A | 5/1998 | Quinn et al. |
| 5,820,769 A | 10/1998 | Chou |
| 5,900,160 A | 5/1999 | Whitesides et al. |
| 5,906,828 A | 5/1999 | Cima et al. |
| 6,048,723 A | 4/2000 | Banes |
| 6,054,277 A | 4/2000 | Furcht et al. |
| 6,133,030 A | 10/2000 | Bhatia et al. |
| 6,197,575 B1 | 3/2001 | Griffith et al. |
| 6,255,106 B1 | 7/2001 | Marx et al. |
| 6,306,644 B1 | 10/2001 | Marx et al. |
| 6,329,195 B1 | 12/2001 | Pfaller |
| 6,454,924 B2 | 9/2002 | Jedrzejewski et al. |
| 6,472,202 B1 | 10/2002 | Banes |
| 6,530,370 B1 | 3/2003 | Heinonen |
| 6,562,616 B1 | 5/2003 | Toner |
| 6,586,235 B1 | 7/2003 | Banes |
| 6,630,801 B2 | 10/2003 | Schuurmans |
| 6,645,432 B1 | 11/2003 | Anderson et al. |
| 6,645,759 B2 | 11/2003 | Banes |
| 6,653,124 B1 | 11/2003 | Freeman |
| 6,730,516 B2 | 5/2004 | Jedrzejewski et al. |
| 6,921,253 B2 | 7/2005 | Shuler et al. |
| 6,998,265 B2 | 2/2006 | Banes |
| 7,049,057 B2 | 5/2006 | Atala et al. |
| 7,288,405 B2 | 10/2007 | Shuler et al. |
| 7,314,718 B1 | 1/2008 | Dasgupta et al. |
| 7,438,856 B2 | 10/2008 | Jedrzejewski et al. |
| 7,745,209 B2 | 6/2010 | Martin et al. |
| 7,763,456 B2 | 7/2010 | Li et al. |
| 7,790,028 B1 | 9/2010 | Weinberg et al. |
| 7,960,166 B2 | 6/2011 | Vacanti et al. |
| 7,964,078 B2 | 6/2011 | Lee et al. |
| 7,976,795 B2 | 7/2011 | Zhou et al. |
| 7,977,089 B2 | 7/2011 | Wikswo et al. |
| 7,985,336 B2 | 7/2011 | Weinberg et al. |
| 8,030,061 B2 | 10/2011 | Shuler et al. |
| 8,147,562 B2 | 4/2012 | Vacanti et al. |
| 8,187,863 B2 | 5/2012 | Sim et al. |
| 8,268,152 B2 | 9/2012 | Stelzle et al. |
| 8,273,572 B2 | 9/2012 | Martin et al. |
| 8,318,479 B2 | 11/2012 | Domansky et al. |
| 8,343,740 B2 | 1/2013 | Gonda et al. |
| 8,357,528 B2 | 1/2013 | Vacanti et al. |
| 8,460,546 B2 | 6/2013 | Weinberg et al. |
| 8,470,589 B2 | 6/2013 | Martin et al. |
| 8,647,861 B2 | 2/2014 | Ingber et al. |
| 9,079,189 B2 | 7/2015 | Garcia et al. |
| 9,182,387 B2 | 11/2015 | Goldkorn et al. |
| 9,322,752 B2 | 4/2016 | Wanders et al. |
| 2002/0129813 A1 | 9/2002 | Litherland et al. |
| 2002/0173033 A1 | 11/2002 | Hammerick et al. |
| 2003/0021792 A1 | 1/2003 | Roben et al. |
| 2003/0082795 A1 | 5/2003 | Shuler et al. |
| 2003/0096405 A1 | 5/2003 | Takayama et al. |
| 2003/0175824 A1 | 9/2003 | Pishko et al. |
| 2003/0180807 A1 | 9/2003 | Hess et al. |
| 2003/0215941 A1 | 11/2003 | Campbell et al. |
| 2004/0034435 A1 | 2/2004 | Atala |
| 2004/0132166 A1 | 7/2004 | Miller et al. |
| 2005/0032205 A1 | 2/2005 | Smith et al. |
| 2005/0169962 A1 | 8/2005 | Bhatia et al. |
| 2005/0266393 A1 | 12/2005 | Baxter et al. |
| 2005/0273995 A1 | 12/2005 | Kanagasabapathi et al. |
| 2006/0019326 A1 | 1/2006 | Vacanti et al. |
| 2006/0099116 A1 | 5/2006 | Manger et al. |
| 2006/0154361 A1 | 7/2006 | Wikswo et al. |
| 2006/0263336 A1 | 11/2006 | Caplan |
| 2006/0270023 A1 | 11/2006 | Leduc et al. |
| 2007/0015273 A1 | 1/2007 | Shuler et al. |
| 2007/0015274 A1 | 1/2007 | Shuler et al. |
| 2007/0015275 A1 | 1/2007 | Shuler et al. |
| 2007/0020693 A1 | 1/2007 | Shuler et al. |
| 2007/0026519 A1 | 2/2007 | Shuler et al. |
| 2007/0037273 A1 | 2/2007 | Shuler et al. |
| 2007/0037275 A1 | 2/2007 | Shuler et al. |
| 2007/0037277 A1 | 2/2007 | Shuler et al. |
| 2007/0048727 A1 | 3/2007 | Shuler et al. |
| 2007/0122794 A1 | 5/2007 | Shuler et al. |
| 2007/0122896 A1 | 5/2007 | Shuler et al. |
| 2007/0144514 A1 | 6/2007 | Yeates et al. |
| 2007/0166816 A1 | 7/2007 | Campbell et al. |
| 2007/0172943 A1 | 7/2007 | Freedman et al. |
| 2007/0207194 A1 | 9/2007 | Grayburn et al. |
| 2007/0224677 A1 | 9/2007 | Neumann |
| 2007/0243627 A1 | 10/2007 | Takayama et al. |
| 2007/0272000 A1 | 11/2007 | Kahl et al. |
| 2007/0275435 A1 | 11/2007 | Kim et al. |
| 2007/0275455 A1 | 11/2007 | Hung et al. |
| 2007/0275882 A1 | 11/2007 | Meijer et al. |
| 2007/0281353 A1 | 12/2007 | Vacanti et al. |
| 2008/0032380 A1 | 2/2008 | Kleis et al. |
| 2008/0064088 A1 | 3/2008 | Shuler et al. |
| 2008/0166794 A1 | 7/2008 | Shuler et al. |
| 2008/0166795 A1 | 7/2008 | Shuler et al. |
| 2008/0233607 A1 | 9/2008 | Yu et al. |
| 2008/0318334 A1 | 12/2008 | Robotti |
| 2009/0028755 A1 | 1/2009 | Jedrzejewski et al. |

(56) References Cited

U.S. PATENT DOCUMENTS

| | | |
|---|---|---|
| 2009/0074623 A1 | 3/2009 | Park et al. |
| 2009/0078614 A1 | 3/2009 | Varghese et al. |
| 2009/0131858 A1 | 5/2009 | Fissell et al. |
| 2009/0134235 A1 | 5/2009 | Ivri |
| 2009/0220932 A1 | 9/2009 | Ingber et al. |
| 2010/0041128 A1 | 2/2010 | Banes et al. |
| 2010/0043494 A1 | 2/2010 | Gascon et al. |
| 2010/0267136 A1 | 10/2010 | Vacanti et al. |
| 2010/0294986 A1 | 11/2010 | Sultana et al. |
| 2010/0304355 A1 | 12/2010 | Shuler et al. |
| 2010/0323439 A1 | 12/2010 | Takayama et al. |
| 2011/0000482 A1 | 1/2011 | Gumaste et al. |
| 2011/0027804 A1 | 2/2011 | Yarmush et al. |
| 2011/0053207 A1 | 3/2011 | Hoganson et al. |
| 2011/0086382 A1 | 4/2011 | Marx |
| 2011/0183312 A1 | 7/2011 | Huang |
| 2011/0250585 A1 | 10/2011 | Ingber et al. |
| 2011/0269226 A1 | 11/2011 | Van Noort et al. |
| 2011/0287469 A1 | 11/2011 | Guenther et al. |
| 2012/0003732 A1 | 1/2012 | Hung et al. |
| 2012/0028355 A1 | 2/2012 | Sato et al. |
| 2012/0088693 A1 | 4/2012 | Lee et al. |
| 2012/0135446 A1 | 5/2012 | Collins et al. |
| 2012/0135452 A1 | 5/2012 | Shuler et al. |
| 2012/0199487 A1 | 8/2012 | Stelzle et al. |
| 2012/0214189 A1 | 8/2012 | Shuler et al. |
| 2012/0318726 A1 | 12/2012 | Charest et al. |
| 2012/0322097 A1 | 12/2012 | Charest et al. |
| 2013/0059322 A1 | 3/2013 | Hung et al. |
| 2013/0109594 A1 | 5/2013 | Gonda et al. |
| 2013/0157360 A1 | 6/2013 | March et al. |
| 2014/0038279 A1 | 2/2014 | Ingber et al. |
| 2014/0158233 A1 | 6/2014 | Leslie et al. |
| 2014/0186414 A1 | 7/2014 | Ingber et al. |
| 2014/0199764 A1 | 7/2014 | Domansky et al. |
| 2014/0342445 A1 | 11/2014 | Ingber et al. |
| 2015/0004077 A1 | 1/2015 | Wikswo et al. |
| 2015/0079670 A1 | 3/2015 | Domansky et al. |
| 2015/0209783 A1 | 7/2015 | Ingber et al. |
| 2015/0306596 A1 | 10/2015 | Thompson et al. |

FOREIGN PATENT DOCUMENTS

| | | |
|---|---|---|
| WO | 2010/118857 A2 | 10/2010 |
| WO | 2012032646 A1 | 3/2012 |
| WO | 2013/158939 A1 | 10/2013 |
| WO | 2014/210364 A2 | 12/2014 |
| WO | 2015/006751 A1 | 1/2015 |
| WO | 2015/013332 A1 | 1/2015 |
| WO | 2015/138032 A2 | 9/2015 |
| WO | 2015/138034 A2 | 9/2015 |

OTHER PUBLICATIONS

Basson, "Paradigms for mechanical signal transduction in the intestinal epithelium", Digestion 68(4):217-225 (2004).

Carvalho et al., "A three-dimensional tissue culture model for the study of attach and efface lesion formation by enteropathogenic and enterohaemorrhagic *Escherichia coli*", Cell. Microbiol. 7(12):1771-1781 (2005).

Chaturvedi et al., "Repetitive deformation activates focal adhesion kinase and ERK mitogenic signals in human Caco-2 intestinal epithelial cells through src and rac1", J. Biol. Chem. 282(1):14-28 (2006).

Eveillard et al., "Identification and characterization of adhesive factors of Clostridium difficile involved in adhesion to human colonic enterocyte-like Caco-2 and mucus-secreting HT29 cells in culture", Molecular Microbiology 7(3):371-381 (1993).

Grajek and Olejnik, Polish Journal of Food and Nutrition Sciences, 13/54(1s):5-24 (2004). "Epithelial cell cultures in vitro as a model to study functional properties of food."

Huh et al., "Reconstituting Organ-Level Lung Functions on a Chip", Science 328:1662-1668 (2010).

Imura et al., "Micro Total Bioassay System for Ingested Substances: Assessment of Intestinal Absorption, Hepatic Metabolism, and Bioactivity", Anal. Chem. 82(24):9983-9988 (2010).

Kim et al., "Co-culture of epithelial cells and bacteria for investigating host-pathogen interactions", Lab Chip 10(1):43-50 (2010).

Kim et al., "Microfluidic Co-culture of Epithelial Cells and Bacteria for Investigating Soluble Signal-mediated Interactions", Journal of Visualized Experiments 38 (2010). (4 pages).

Kimura et al., "An integrated microfluidic system for long-term perfusion culture and on-line monitoring of intestinal tissue models", Lab on a Chip 8(5):741-746 (2008).

Konkel et al., "Translocation of Campylobacter jejuni across Human Polarized Epithelial Cell Monolayer Cultures", The Oxford Journal of Infectious Diseases 166(2):308-315 (1992).

Lee et al., "The ability of *Salmonella* to enter mammalian cells is affected by bacterial growth state", Proc. Natl. Acad. Sci. USA 87(11):4304-4308 (1990).

Mahler et al., "Characterization of a Gastrointestinal Tract Microscale Cell Culture Analog Used to Predict Drug Toxicity", Biotechnology and Bioengineering 104(1):193-205 (2009).

Murnin et al., "Effects of glutamine isomers on human (Caco-2) intestinal epithelial proliferation, strain-responsiveness, and differentiation", J. Gastrointest. Surg. 4(4):435-442 (2000).

Womack et al., "Quantitative assessment of villous motility." Am. J. Physiol. 252(2 Pt 1):G250-256 (1987).

Zhang et al., "Regulation of the Intestinal epithelial response to cyclic strain by extracellular matrix proteins", FASEB J. 17(8):926-928 (2003).

Sato et al., "Single Lgr5 stem cells build crypt-villus structures in vitro without a mesenchymal niche" Nature 459(7244):262-265 (2009).

FLUIDIC CONDITION (W/O STRETCHING)

STATIC CONDITION (TRANSWELL)

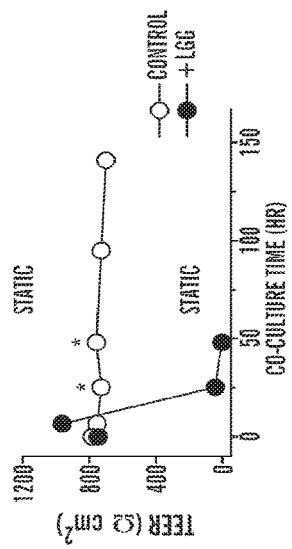
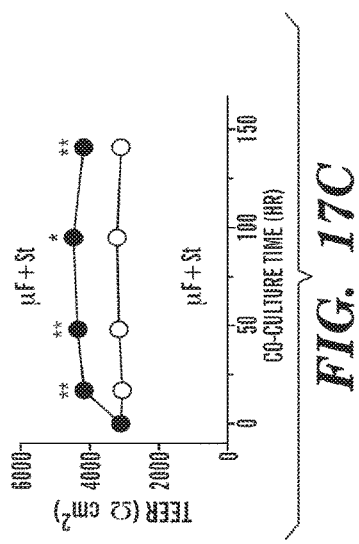
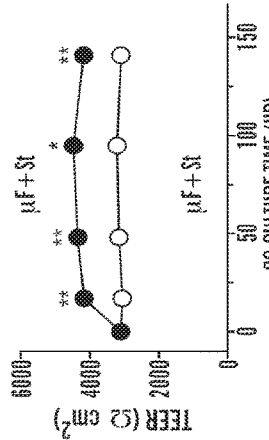
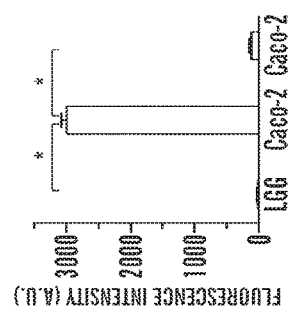
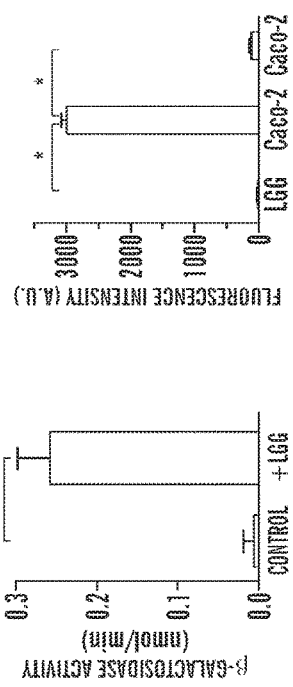
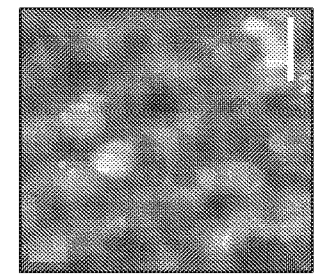
FIG. 17A  FIG. 17B  FIG. 17C  FIG. 17D  FIG. 17E

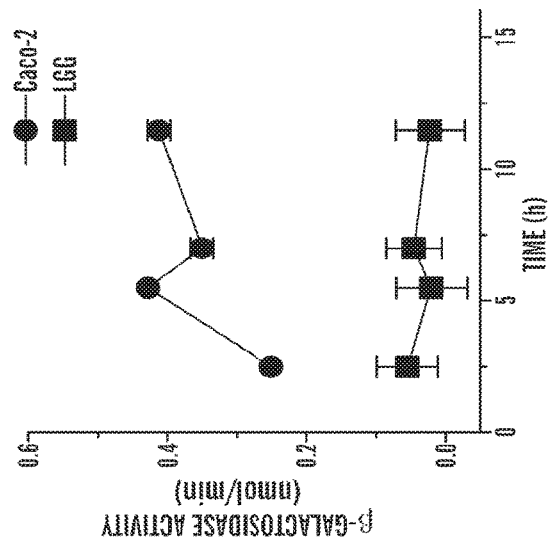
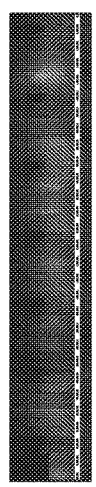
FIG. 18A
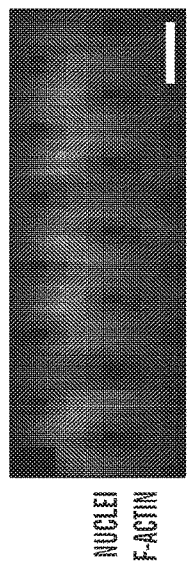
FIG. 18B
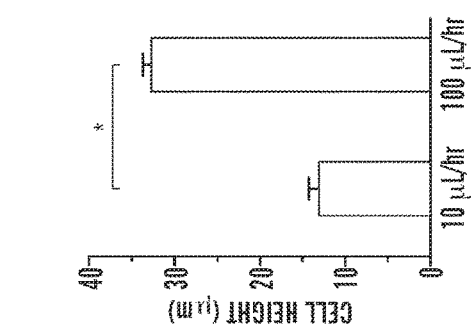
FIG. 18C
FIG. 19

CELL CULTURE SYSTEM

CROSS REFERENCE TO RELATED APPLICATIONS

This application is a divisional application of co-pending application U.S. Ser. No. 14/001,838 filed Oct. 11, 2013, which is a 35 U.S.C. § 371 National Phase Entry Application of International Application No. PCT/US12/26934 filed Feb. 28, 2012, which designates the U.S., and which claims benefit under 35 U.S.C. § 119(e) of U.S. Provisional Patent Application No. 61/447,540 filed Feb. 28, 2011, the contents of each of which are incorporated herein by reference in their entireties.

GOVERNMENT SUPPORT

This invention was made in part with U.S. Government support from grant ES016665-01A1 from the National Institute of Environmental Health Sciences. The U.S. Government has certain rights in this invention.

FIELD OF THE INVENTION

The systems and methods of the invention as described herein relate to the culturing and maintaining of in vitro intestinal organoids.

BACKGROUND

Drug development has been hampered because it relies on the use of animal models that are costly, labor-intensive, time-consuming and questionable ethically.[1] Of even greater concern is that animal models often do not predict results obtained in humans,[2-3] and this is a particular problem when addressing challenges relating to metabolism, transport, and oral absorption of drugs and nutrients.[4-5] For these reasons, there has been increasing interest in development of in vitro models of human intestinal function, including cell culture systems that utilize Transwell filter inserts[6-7] which enable trans-epithelial barrier and transport studies,[8-9] and miniaturized microfluidic models that also support long-term culture.[10-14] Others have attempted to recreate the normal three-dimensional (3D) architecture of the intestinal lining in vitro by culturing human intestinal epithelial (e.g. Caco-2) cells on hydrogel substrates that were microengineered to mimic the shape, size and density of human intestinal villi.[11] However, none of the existing in vitro intestinal models recapitulate the mechanically active microenvironment of living intestine (peristaltic motions and intralumenal fluid flow) that is critical for normal organ physiology,[15] as well as for development of Crohn's disease and other intestinal disorders.[16-17] Another limitation of existing in vitro gut models is that it has not been possible to grow living microbes on the luminal surface of cultured intestinal epithelium for extended periods as normally occurs in living intestine. This is a key problem because microbial symbionts normally contribute significantly to intestinal barrier function, metabolism and absorption of drugs and chemicals, and to many diseases.[18-22] Development of an in vitro living cell-based model of the intestine that mimics the mechanical, structural, absorptive, transport and pathophysiological properties of the human gut along with its crucial microbial symbionts could accelerate pharmaceutical development, and potentially replace animal testing.

SUMMARY OF THE INVENTION

Described herein are systems and methods relating to cell culture systems for maintaining and/or culturing intestinal organoids and/or intestinal epithelial cells in vitro. The embodiments of the invention described herein are based upon the inventors' discovery that providing fluid flow, shear stress, and/or mechanical stress allows more physiologically relevant recapitulation of the intestinal environment. The systems and methods described herein can be used for the purposes of studying or examining pharmacology, toxicology, drug development, drug delivery, drug metabolism, drug-drug interaction drug bioavailability, drug clearance, multi-organ interactions, diagnostics, therapeutics, nutritional applications, physiology of the intestinal barrier, gastrointestinal (GI) disease models and their mechanism, etiology of disease in the GI tract, wound healing, tissue regeneration, tissue engineering, intestinal homeostasis, intestinal stem cell researches, host-microbes interactions, microbial communities in the GI tract, microbial biofilm in the mucus layer, and probiotics therapies.

In one aspect, the invention described herein relates to a cell culture system comprising, (i) a fluidic device having a fluid channel connected to a fluid source, the fluid source supplying fluid to the fluid channel; (ii) a membrane positioned within the channel between membrane support elements, at least portion of the membrane being flexible; (iii) a membrane strain mechanism coupled to the membrane support elements capable of moving the membrane support elements and causing the membrane to stretch along at least one dimension of the membrane; and (iv) at least one layer of intestinal epithelial cells attached to at least one surface of the membrane; wherein the shear stress on the fluid flowing through the fluid channel is less than 1.0 dyne/cm$^2$.

In some embodiments, the shear stress on the fluid flowing through the fluid channel is from 0.008 to 0.08 dyne/cm$^2$. In some embodiments, the shear stress on the fluid flowing through the fluid channel is approximately 0.018 dyne/cm$^2$. In some embodiments, the shear stress on the fluid flowing through the fluid channel can vary over time. In some embodiments, the shear stress on the fluid flowing through the fluid channel can vary over time from 0 to 1000 dyne/cm$^2$. In some embodiments, the shear stress on the fluid flowing through the fluid channel can vary over time from 0.008 to 0.08 dyne/cm$^2$.

In some embodiments, the membrane is caused to stretch from 0% to 50%. In some embodiments, the membrane is caused to stretch from 5% to 15%. In some embodiments, the membrane is caused to stretch approximately 10%. In some embodiments, the membrane is caused to stretch more than 15% to create an abnormal condition/state of the intestinal epithelial cells.

In some embodiments, the membrane is caused to stretch in a cyclic manner at a rate in the range of 0.01 Hz to 2 Hz. In some embodiments, the membrane is caused to stretch in a cyclic manner at a rate in the range of 0.05 Hz to 0.25 Hz. In some embodiments, the membrane is caused to stretch in a cyclic manner at a rate of 0.15 Hz. In some embodiments, the membrane is caused to stretch in a cyclic manner at a rate greater than 0.2 Hz to create an abnormal condition/state of the intestinal epithelial cells. In some embodiment, the membrane is caused to stretch in an irregular or intermittent manner.

In some embodiments, the fluid flows through the fluid channel at a flow rate less than 500 µL/hr. In some embodiments, the fluid flows through the fluid channel at a flow rate less than 100 µL/hr. In some embodiments, the fluid flows through the fluid channel at a flow rate from 0 to 50 µL/hr. In some embodiments, the fluid flows through the fluid channel at a flow rate of approximately 30 µL/hr.

In some embodiments, the system further comprises at least one type of attachment molecule that supports adhesion of a plurality of living cells coating at least one side of the membrane. In some embodiments, the at least one attachment molecule is selected from the group consisting of: collagen; collagen type I; MATRIGEL™; extracellular matrix; laminin; proteoglycan; vitronectin; fibronectin; poly-D-lysine; polypeptides; oligonucleotides; DNA; and polysaccharide.

In some embodiments, the intestinal epithelial cells are mammalian or human cells. In some embodiments, intestinal epithelial cells are selected from the group consisting of: Caco2 cells; HT-29 cells; primary small intestine epithelial cells; primary large intestine epithelial cells; iPS cells; ESC cells; stem cells; paneth cells; crypt cells; and mucus-secreting cells. In some embodiments, the intestinal epithelial cells of the system further comprise villi structures. In some embodiments, the system further comprises at least one layer of endothelial cells on at least the second surface of the membrane.

In some embodiments, the membrane is positioned such that it divides the fluid channel into a first cell culture channel and a second cell culture channel. In some embodiments, the first cell culture channel comprises intestinal epithelial cells. In some embodiments, the second cell culture channel comprises cells selected from the group consisting of: endothelial cells, immune cells, and connective tissue cells.

In some embodiments, the system further comprises microbial cells or pathogens. In some embodiments, the microbial cells are maintained in the system for at least 1 day. In some embodiments, the microbial cells are selected from the group consisting of: *Lactobacillus*; *Bacterioides*; *Ruminococcus*; *Peptococcus*; *Peptostreptococcus*; *Bifidobacterium*; *Escherichia*; *Achromobacter*; *Acidaminococcus fermentans*; *Acinetobacter cacoaceticus*; *Aeromonas*; *Alcaligenes faecalis*; *Bacillus*; *Butyriviberio fibrosolvens*; *Camplyobacter*; *Campylobacter coli*; *Clostridium difficile*; *Clostridium sordelli*; *Enterobacter cloacae*; *Enterococcus faecalis*; *Enterococcus faecium*; *Escherichia coli*; *Flavobacterium*; *Mycobacterium*; *Mycoplasma*; *Plesiomonas shigelloides*; *Propionibacterium acnes*; *Pseudomonas aeruginosa*; *Ruminococcus bromii*; *Sarcina*; *Staphylococcus aureus*; *Streptococcus anginosus*; *Veillonella*; *Vibrio*; *Yersinia enterocolitica*; *Lactobacillus rhamnosus*; *Lactobacillus rhamnosus GG*; *Bifidobacterium breve*; *Bifidobacterium longum*; *Bifidobacterium infantis*; *Lactobacillus acidophilus*; *Lactobacillus plantarum*; *Lactobacillus paracasei*; *Lactobacillus bulgaricus*; and *Streptococcus thermophilus*. In some embodiments, the microbial cells are pathogenic. In some embodiments, the pathogens are selected from the group consisting of: enterotoxigenic *Escherichia coli*; *Bilophila wadsworthia*; *Shigella*; *Yersinia*; *Pleisiomonas*; *Vibrio*; *Aeromonas*; *Campylobacter*; *Crytosporidia*; *Coccidosis*; *Salmonella*; *Helicobacter pylori*; *Clostridium difficile*; *Salmonella kedougou*; *Bacteroides*; *Clostridium*; *Firmicutes*; *Shigellia dysenteriae*; *Salmonella enterica*; *Salmonella typhi*; *Listeria*; *Listeria monocytogenes*; *Vibrio parahaemolyticus*; *Proteus*; *Vibrio cholerae*; *Enterococcus faecalis*; *Yersinia enterocolitica*; and *Campylobacter jejuni*; rotavirus; norwalk-like viruses; adenoviruses; astroviruses; sapporo-like viruses; toroviruses; coronaviruses; picornaviruses; herpes viruses; noroviruses; *Candida*; *Aspergillus*; *Candida albicans*; single-celled parasites; multi-celled parasites; ameobas; worms; tape worms; protozoans; flukes; roundworms; pinworms; hookworms; *Giradia lamblia*; *cryptosporidium*; and *Entamoeba histolytica*. In some embodiments, the microbial cells are aerobic. In some embodiments, the microbial cells are anaerobic. In some embodiments, the system comprises both aerobic and anaerobic microbial cells. In some embodiments, the microbial cells are present in the first cell culture channel.

In some embodiments, the system further comprises an anaerobic gas chamber in contact with at least part of the first cell culture channel. In some embodiments, an oxygen gradient is established in the fluid flowing through the first cell culture channel.

In some embodiments, the membrane is at least partially porous. In some embodiments, at least one pore aperture in the membrane is between 0.5 µm and 10 µm along a width dimension. In some embodiments, the membrane comprises PDMS. In some embodiments, the membrane is caused to stretch due to vacuum pressure.

In some embodiments, the system further comprises: (i) a first chamber wall of the device positioned adjacent to the at least one fluid channel, wherein the membrane is mounted to the first chamber wall; (ii) a first operating channel adjacent to the at least one fluid channel on an opposing side of the first chamber wall, wherein a pressure differential applied between the first operating channel and the at least one fluid channel causes the first chamber wall to flex in a first desired direction to expand or contract along the plane defined by the membrane; and (iii) a vacuum system providing a pressure differential between the at least one fluid channel the at least one operating channels, wherein the membrane stretches along the plane in response to the pressure differential. In some embodiments, the system further comprises a second chamber wall of the device positioned adjacent to the at least one fluid channel, wherein an opposing end of the membrane is mounted to the second chamber wall; and a second operating channel positioned adjacent to the at least one fluid channel on an opposing side of the second chamber wall, wherein the pressure differential between to the second operating channel and the at least one fluid channel causes the second chamber wall to flex in a second desired direction to expand or contract along the plane defined by the membrane.

In some embodiments, the fluidics device comprises a microfluidic chip.

In some embodiments, the system is connected or coupled to a second cell culture system comprising cells or tissue which are not intestinal in origin. In some embodiments, the second cell culture system comprises liver cells or tissue.

In one aspect, the invention described herein relates to a method of producing an intestinal organoid comprising; providing a fluid suitable for maintaining intestinal epithelial cells to the cell culture system as described herein such that the fluid contacts the intestinal epithelial cells; and culturing the intestinal epithelial cells in vitro. In some embodiments, the method further comprises culturing the cells at least until villi structures are evident.

In one aspect, the invention described herein relates to a system for evaluating intestinal effector agents comprising a cell culture system as described herein.

In one aspect, the invention described herein relates to a method of evaluating intestinal treatments; comprising contacting the cells of a cell culture system as described herein with at least one candidate intestinal treatment effector; and measuring the response of the cells in the system to determine the effect of the at least one candidate intestinal effector agent.

BRIEF DESCRIPTION OF THE DRAWINGS

FIG. 6A depicts a schematic of 'dynamic condition' representing mechanical deformations with constant flow. FIG. 6B depicts a schematic of 'fluidic condition' where no mechanical deformations under constant flow. FIG. 6C depicts a schematic of 'static condition' showing a conventional Transwell system where there is no mechanical deformations and no flow as well.

FIG. 12A depicts a schematic of the Gut-on-a-Chip device showing the flexible porous ECM-coated membrane lined by gut epithelial cells crossing horizontally through the middle of the central microchannel, and full height vacuum chambers on both sides. FIG. 12B depicts a photographic image of the Gut-on-a-Chip device composed of clear PDMS elastomer. A syringe pump was used to perfuse (direction indicated by arrows) blue and red dyes through tubing to the upper and lower microchannels, respectively, to visualize these channels. FIG. 12C depicts a cross-sectional view of the top and bottom channels (both 150 µm high) of the Gut-on-a-Chip; square inset shows a top view of a portion of the porous membrane (10 µm pores; bar, 20 µm). FIG. 12D depicts schematics (top) and phase contrast images (bottom) of intestinal monolayers cultured within the Gut-on-a-Chip in the absence (left) or presence (right) of mechanical strain (30%; arrow indicated direction) exerted by applying suction to the vacuum chambers. Red and blue outlines indicate the shape of a single Caco-2 cell before (red) and after (blue) mechanical strain application (bar, 20 µm). Note that the cell distorts in the direction of the applied tension. FIG. 12E depicts a graph of the quantitation of the mechanical strain produced in the ECM-coated, flexible, porous PDMS membrane (open circles) and in the adherent gut epithelial cells (closed circles) as a function of pressure applied by the vacuum controller.

FIGS. 14A-14D depict the morphology of Caco-2 epithelial cells in different cell culture devices. FIG. 14A depicts the morphology of the Caco-2 epithelial cells cultured in the static Transwell system for 21 days. FIGS. 14B-14C depict the morphology of Caco-2 epithelial cells in the Gut-on-a-Chip with microfluidic flow (30 µL/hr; µF) without (FIG. 14B) or with (FIG. 14C) application of cyclic mechanical strain (10%; 0.15 Hz; µF+St) for 3 days. Schematics (left) show the system layout; fluorescence views (center) show the distribution of the tight junction protein, occludin, in the epithelial monolayers; and the confocal fluorescence views (right) show of a vertical cross section of the epithelium highlighting cell shape and polarity (nuclei in blue and F-actin in green). The regular array of small white circles in (FIG. 14B) and (FIG. 14C) are pores visible beneath the epithelial monolayer; the dashed white line indicates top of anchoring substrate (bar, 20 µm). FIG. 14D depicts a graph of the average height of Caco-2 cells grown in static Transwell cultures or the microfluidic Gut-on-a-Chip without (µF) or with (µF+St) mechanical strain (* $p<0.001$).

FIG. 15A depicts phase contrast views of a Caco-2 cell monolayer at 58, 132, and 170 hours of culture in the presence of flow and cyclic strain (30 µL/hr, 10% strain, 0.15 Hz). Note the planar epithelial monolayer visible at early times takes on an undulating quality with regions in and out of focus at later times that is suggestive of villi formation. FIG. 15B depicts a confocal fluorescence view of a vertical cross section of a region of the undulating epithelium at 170 h confirming the presence of intestinal villi lined by consistently polarized columnar epithelial cells labeled with F-actin (green) with basal nuclei (blue) and apical mucin expression (magenta) separated by a crypt. The regular array of small white circles are pores visible beneath the epithelial monolayer; bar, 20 µm.

FIG. 16A depicts the tight junctional integrity of the epithelium quantified by measuring TEER of the Caco-2 monolayer. FIG. 16B depicts the apparent paracellular permeability ($P_{app}$) measured by quantitating fluorescent dextran transport through the Caco-2 monolayer cultured under static conditions for 5 or 21 days, or in the microfluidic Gut-on-a-Chip in the absence (µF) or presence (µF+St) of cyclic strain for 5 days (*** $p<0.05$). FIG. 16C depicts intestinal cell differentiation assessed by measuring brush border aminopeptidase activity in Caco-2 cells cultured under static conditions for 5 or 21 days, or in the microfluidic Gut-on-a-Chip in the absence (µF) or presence (µF+St) of cyclic strain for 5 days (* $p<0.001$, ** $p<0.01$).

FIGS. 17A-17E depict the results of long-term microbial co-culture on a human intestinal epithelial monolayer in the Gut-on-a-Chip. A bacterium originally isolated from human intestine, *Lactobacillus rhamnosus* GG (LGG), was cultured on the surface of a Caco-2 monolayer grown within the Gut-on-a-Chip. FIG. 17A depicts phase contrast views from above of LGG and Caco-2 cells co-cultured for 96 hours and viewed at low (left) and high (right) magnification, which show microcolonies of LGG cells (white arrows) that remain tightly adherent to the apical surface of the Caco-2 cell monolayer after exposure to continuous fluidic flow (bar, 20 µm in all views). FIG. 17B depicts simultaneous live/dead staining of a Caco-2 monolayer co-cultured with LGG for 96 hours demonstrating that virtually all epithelial cells remained viable (green). FIG. 17C depicts barrier functions of the Caco-2 monolayer cultured in the absence (open circles) or presence (closed circles) of LGG cells in Transwell (Static) or microfluidic Gut-on-a-Chip with cyclic strain (µF+St; 40 µL/hr, 10% cell strain, 0.15 Hz). Note that error bars were smaller than the symbol size (* $p<0.01$, ** $p<0.05$). FIG. 17D depicts assessment of the functionality of viable LGG cells co-cultured with Caco-2 cells for 96 hours carried out by measuring the catalytic activity of β-galactosidases in LGG cells co-cultured with Caco-2 cells in Gut-on-a-chip with mechanical strain (+LGG; 40 µL/hr, 10% cell strain, 0.15 Hz) or in Caco-2 cells cultured alone as a control (*$p<0.01$). FIG. 17E depicts a graph of the amount of fluorescence, a measure of calcein AM cleavage, detected under various conditions, demonstrating that the fluorescent staining in FIG. 17B is contributed by viable Caco-2 cells, and is not an artifact of viable LGG cells.

FIGS. 18A-18C demonstrate that fluid flow is a critical factor for the control of cell shape and polarity in Caco-2 cells. Confocal fluorescence views of a vertical cross section through a Caco-2 monolayer cultured in the Gut-on-a-Chip using flow rates of 10 μL/hr (FIG. 18A) or 100 μL/hr (FIG. 18B) for 20 hours in the absence of cyclic strain, confirming that higher flow rates (30-100 μL/hr) specifically induce polarization and formation of a columnar epithelium. FIG. 18C depicts quantification of the mean heights of Caco-2 cells cultured at either 10 μL/hr or 100 μL/hr without mechanical strain (*, p<0.0001; bar, 20 μm).

FIG. 19 depicts assessment of β-Galactosidase activity in live LGG cells and Caco-2 cells cultured independently. Live LGG cells actively cleaved the β-galactosidase substrate, ONPG, and produced a progressive increase of optical density of the O-nitrophenol product (closed circles), whereas human Caco-2 epithelial cells did not exhibit any specific β-Galactosidase (closed squares). Differences in activity expressed by LGG versus Caco-2 cells were significant (p<0.001) at all time points.

DETAILED DESCRIPTION OF THE INVENTION

Figure 1:
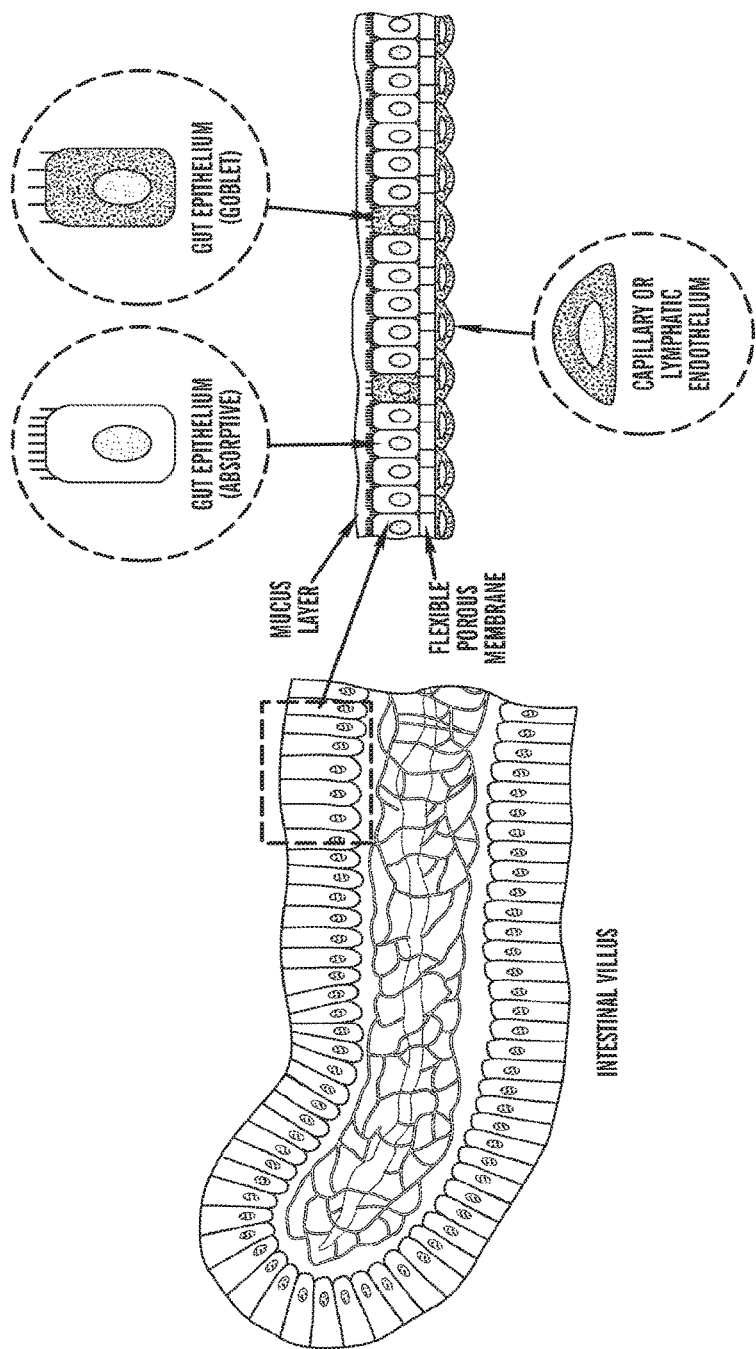
FIG. 1 depicts a structural recapitulation of the human intestinal villus. A porous membrane is surrounded by the gut epithelium and capillary endothelium.

For convenience, certain terms employed herein, in the specification, examples and appended claims are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

As used herein the term "comprising" or "comprises" is used in reference to compositions, methods, and respective component(s) thereof, that are essential to the method or composition, yet open to the inclusion of unspecified elements, whether essential or not.

As used herein the term "consisting essentially of" refers to those elements required for a given embodiment. The term permits the presence of elements that do not materially affect the basic and novel or functional characteristic(s) of that embodiment.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); The ELISA guidebook (Methods in molecular biology 149) by Crowther J. R. (2000). Definitions of common terms in molecular biology can also be found in Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8).

Unless otherwise stated, the present invention was performed using standard procedures, as described, for example in U.S. Pat. Nos. 4,965,343, and 5,849,954; Sambrook et al., Molecular Cloning: A Laboratory Manual (3 ed.), Cold Spring Harbor Laboratory Press, Cold Spring Harbor, N.Y., USA (2001); Davis et al., Basic Methods in Molecular Biology, Elsevier Science Publishing, Inc., New York, USA (1995); Current Protocols in Cell Biology (CPCB) (Juan S. Bonifacino et. al. ed., John Wiley and Sons, Inc.); Culture of Animal Cells: A Manual of Basic Technique by R. Ian Freshney, Publisher: Wiley-Liss; 5th edition (2005); and Animal Cell Culture Methods (Methods in Cell Biology, Vol. 57, Jennie P. Mather and David Barnes editors, Academic Press, 1st edition, 1998) which are all incorporated by reference herein in their entireties.

The terms "decrease," "reduce," "reduced", and "reduction" are all used herein generally to mean a decrease by a statistically significant amount relative to a reference. However, for avoidance of doubt, "reduce," "reduction", or "decrease" typically means a decrease by at least 10% as compared to the absence of a given treatment and can include, for example, a decrease by at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, up to and including, for example, the complete absence of the given entity or parameter as compared to the absence of a given treatment, or any decrease between 10-99% as compared to the absence of a given treatment.

The terms "increased", "increase", or "enhance" are all used herein to generally mean an increase by a statically significant amount; for the avoidance of any doubt, the terms "increased", "increase", or "enhance" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

As used herein, "maintaining" or "culturing" refers to continuing the viability of a tissue or population of cells. A maintained tissue will have a population of metabolically active cells. The number of these cells can be roughly stable over a period of at least 3 days or can grow.

As used herein, the terms "microfluidic device" and "microfluidic chip" are used interchangeably and refer to a structure or substrate having microfluidic structures contained therein or thereon. In some embodiments, the chip can be detachably connected to a microfluidic system.

As used herein, the term "stem cell" refers to cells that are undifferentiated and have the ability to differentiate into the desired cell type, i.e. endothelial cells or intestinal epithelial cells.

As used herein, the term "embryonic stem cell" refers to cells that are totipotent and derived from tissue formed after fertilization but before the end of gestation, including pre-embryonic tissue (such as, for example, a blastocyst), embryonic tissue, or fetal tissue taken any time during gestation, typically but not necessarily before approximately 10-12 weeks gestation. Embryonic stem cells can be obtained directly from suitable tissue, including, but not limited to human tissue, or from established embryonic cell lines. In one embodiment, embryonic stem cells are obtained as described by Thomson et al. (U.S. Pat. Nos. 5,843,780 and 6,200,806; Science 282:1145, 1998; Curr. Top. Dev. Biol. 38:133 ff, 1998; Proc. Natl. Acad. Sci. U.S.A. 92:7844, 1995 which are incorporated by reference herein in their entirety).

As used herein, the terms "induced pluripotent stem cell" or "iPSC", which are used interchangeably herein, refer to pluripotent cells derived from differentiated cells. For example, iPSCs can be obtained by overexpression of transcription factors such as Oct4, Sox2, c-Myc and Klf4 according to the methods described in Takahashi et al. (Cell, 126: 663-676, 2006). Other methods for producing iPSCs are described, for example, in Takahashi et al. Cell, 131: 861-872, 2007 and Nakagawa et al. Nat. Biotechnol. 26: 101-106, 2008; which are incorporated by reference herein in their entirety.

The term "statistically significant" or "significantly" refers to statistical significance and generally means a two standard deviation (2SD) below normal, or lower, concentration of the marker. The term refers to statistical evidence that there is a difference. It is defined as the probability of making a decision to reject the null hypothesis when the null hypothesis is actually true. The decision is often made using the p-value.

Other than in the operating examples, or where otherwise indicated, all numbers expressing quantities of ingredients or reaction conditions used herein should be understood as modified in all instances by the term "about." The term "about" when used in connection with percentages can mean±1%.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Other terms are defined herein within the description of the various aspects of the invention.

Figure 5:
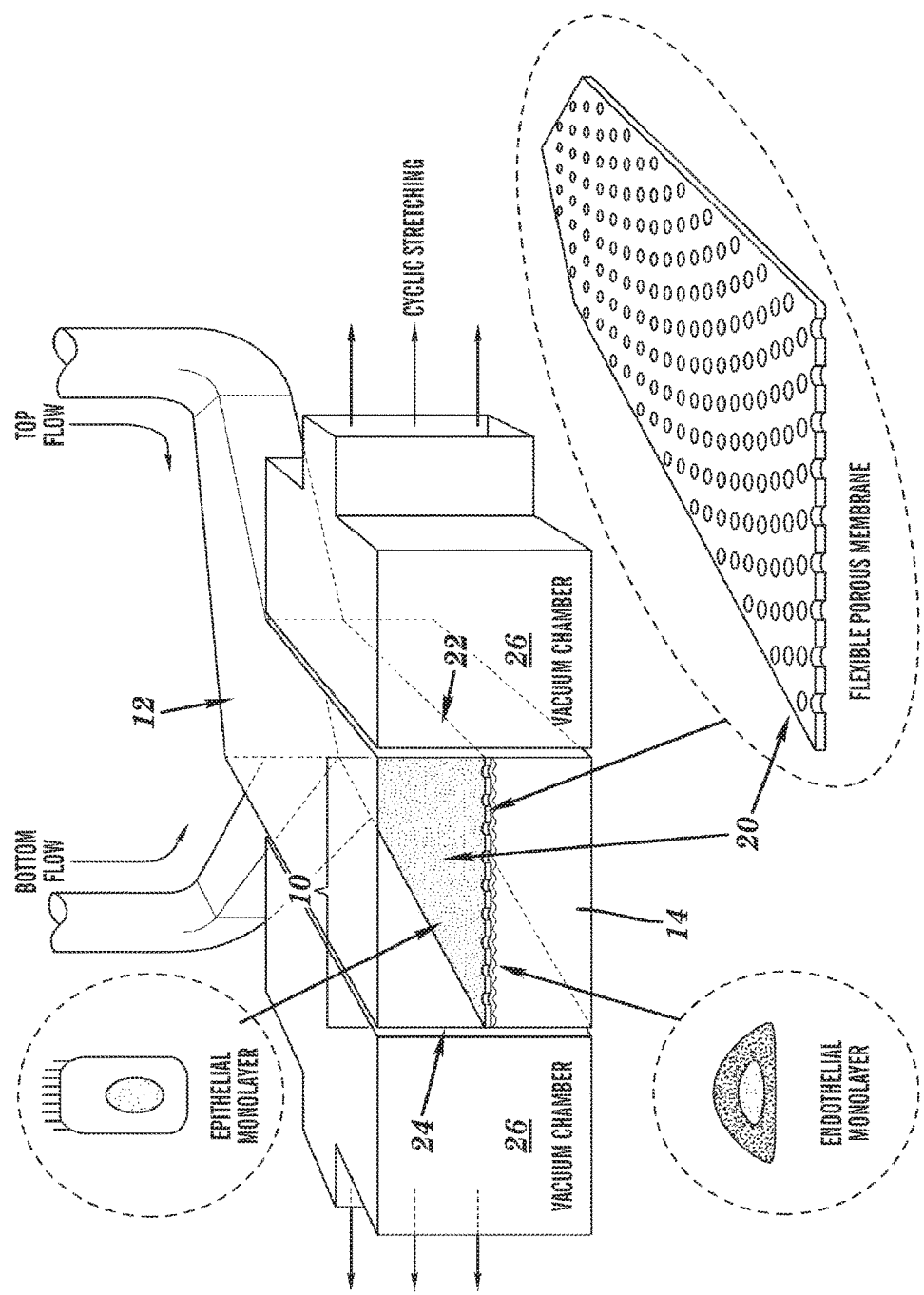
FIG. 5 depicts a schematic of one embodiment of the gut-on-a-chip device to co-culture intestinal epithelium on one side and capillary or lymphatic endothelium on the other side of a flexible porous membrane (10 μm pores in diameter with 30 μm spacing, 30 μm in thickness).

Throughout the specification and figures, the cell culture systems described herein are referred to interchangeably as "gut on a chip." FIG. 5 depicts one embodiment of the cell culture system described herein. In accordance with some embodiments of the invention described herein, the cell culture system can comprise a fluidic device having a fluid channel 10 connected to a fluid source, the fluid source supplying fluid to the fluid channel 10. The size and shape of the fluid channel 10 can vary according to the desired size and shape of the organoid and/or the volume and flow rate of fluid that is to be provided.

As used herein "fluidic device" refers to a device of any size or orientation which comprises one or more fluid channels and is suitable for the culture of living cells. A fluidic device can be capable of moving any amount of fluid within the fluid flow ranges described herein below, e.g. a fluidic device can be a microfluidic device or a device capable of moving larger volumes of fluid. As used herein, the term "channel" refers to any capillary, channel, tube, or groove that is deposed within or upon a substrate. A channel can be a microchannel; i.e. a channel that is sized for passing through microvolumes of liquid.

A fluid source can be a reservoir or other container comprising a volume of fluid such that the fluid can be caused to move from the fluid source and through the one or more channels of the fluidic device. The fluid source can be coupled to the one or more channels of the fluidic device by any means of conducting a fluid, e.g. tubing, piping, channels, or the like. The fluidic device and/or the fluid source can comprise ports. As used herein, the term "port" refers to a portion of the cell culture system described herein which provides a means for fluid and/or cells to enter and/or exit the system and/or to enter and/or exit portions of the system. The port can be of a size and shape to accept and/or secure a connection with tubes, connections, or adaptors of a fluidic or microfluidic system and allow passage of fluid and/or cells when attached to a fluidic or microfluidic system.

In accordance with the various embodiments of the invention, the fluid flows from a fluid source through the fluid channel 10 of the device toward a fluid collection reservoir (not shown). Either positive or negative fluid pressure, or both, can be used to cause the fluid to flow through the fluid channel 10. In accordance with some embodiments of the invention, the fluid in fluid source can be pressurized and a valve can be provided between the fluid source and the fluid channel 10 to control the flow of fluid into the channel. In accordance with some embodiments of the invention, a vacuum source can be connected to the outlet port of the fluid channel 10 to draw the fluid through the fluid channel 10. In accordance with some embodiments of the invention, gravity can be used to cause the fluid to flow through the fluid channel 10. For example, the fluid source can be elevated above the device and the fluid collection reservoir can places below the device to provide fluid pressure that causes fluid to flow through the fluid channel 10. A valve at the fluid source or in the fluid flow path can be used to control the rate of fluid flow. In accordance with some embodiments of the invention, one or more pumps can be used cause the fluid to flow from the fluid source through the fluid channel 10.

Figure 21:
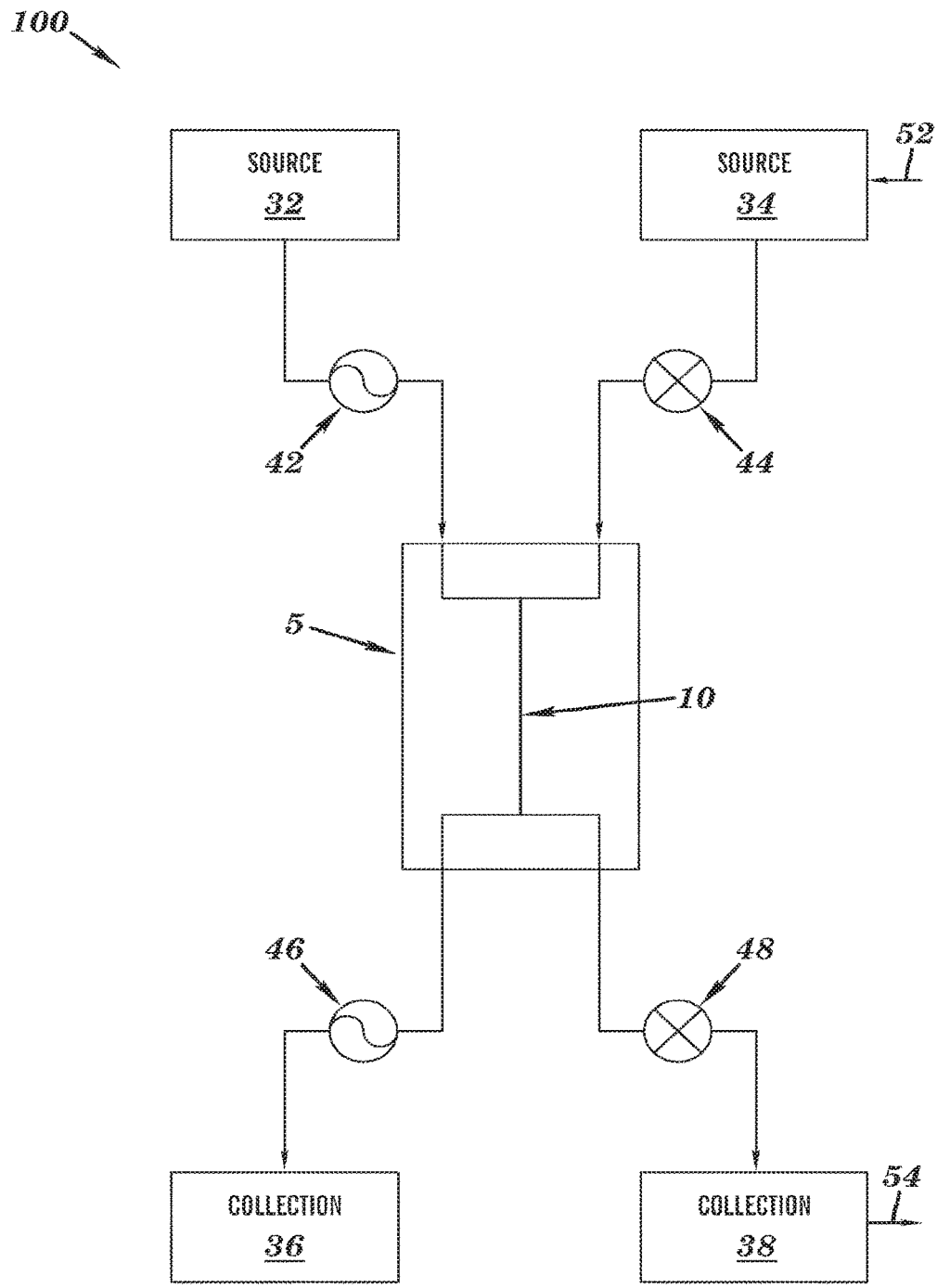
FIG. 21 depicts a diagrammatic view of one embodiment of a system as described herein.

FIG. 21 shows, for illustration purposes, a diagrammatic view of a system 100 according to one embodiment of the invention. The system 100 can include one or more fluid sources (e.g., 32, 34) connected to the microfluidic device 5 (e.g., such as that shown in FIGS. 3, 5, 6 and 12), the microfluidic device 5 including one or more fluid channels 10 which can be connected to one or more fluid collection reservoirs (e.g., 36, 38). In some embodiments, the fluid source 32, 34 can be a simple plastic container holding and supplying on fluid or a container with two or more separate compartments to hold and supply different fluids. In some embodiments, the fluid source 34 can be pressurized by connecting the source container to a supply of pressurize gas 52 (e.g., air or other inert gas) or other fluid (e.g., water, media), the pressure causing the fluid to flow out of the source 34 into the device 5 and through the fluid channel 10. In this embodiment, the source container can be a sealed metal or plastic container sufficient to sustain the pressure. In some embodiments, the fluid collection reservoir 38 can be connected to a source of vacuum 54, the vacuum causing the fluid to flow into the device 5 and through the fluid channel 10 toward the fluid collection reservoir 38. In addition to or as an alternative to pressurization or vacuum, the fluid source 32, 34, containers can be elevated to provide positive pressure to the microfluidic device 5. In some embodiments of the invention, valves 44, 48 can be provided to control the flow of fluid through the device 5. The valves 44, 48, can be connected to a control system, such as computer system 700, to permit automated control of the valves and the fluid flow.

In some embodiments of the invention, the system can include one or pumps 42, 46 to pump the fluid from the fluid source 32, to the microfluidic device 5 and through fluid channel 10 to the fluid collection reservoir 36. In some embodiments of the invention, one pump (e.g., 42 or 46) can be used. In other embodiments of the invention, two or more pumps 42, 46, can be used. The pumps 42, 46, can be connected to a control system, such as computer system 700, to permit automated control of the pumps and the fluid flow. The pumps 46, 48 can be any dynamic or displacement pump, for example, a syringe pump, a peristaltic pump, or positive displacement pump.

In accordance with some embodiments of the invention described herein and as depicted in FIG. 5, the cell culture system can further comprise a membrane 20 positioned within the channel and attached to one or more membrane support elements 22, 24. In some embodiments, the membrane 20 can divide the fluid channel 10 into a first cell culture channel 12 and second cell culture channel 14. The first and second cell culture channels may be in any orientation. By way of non-limiting example, the membrane 20 dividing the cell culture channels can extend along a single plane horizontally, such as depicted in FIG. 5, such that one cell culture channel is located directly above the other cell culture channel. Alternatively, the membrane 20 dividing the cell culture channels can extend along a single plane vertically, such that the two cell culture channels are located in a side-by-side arrangement with neither channel being above the other. Alternatively, the membrane 20 dividing the cell culture channels can be a tubular and/or cylindrical membrane, such that a first cell culture channel is located within the tube formed by the membrane and a second cell culture channel comprises the space between the membrane and the walls of the fluid channel 10. In accordance with some embodiments of the cell culture system described herein, the membrane support elements can be coupled to membrane strain mechanisms 26 capable of moving the membrane support elements and causing the membrane to stretch along at least one dimension of the membrane.

In some embodiments, the membrane is at least partially flexible. In some embodiments the membrane is flexible in at least one dimension, e.g., the membrane can stretch in one dimension, or in two dimensions, or in three dimensions. A membrane can be made of any partially flexible biocompatible material. In some embodiments, the membrane can be made of PDMS. Further examples of biocompatible materials are described below herein.

In some embodiments the membrane is at least partially porous. In some embodiments, the pores of the membrane can be from 0.5 µm to 10 µm in diameter. In some embodiments, the pores of the membrane can be approximately 10 µm in diameter. In some embodiments, the pores of the membrane can be approximately 5 µm in diameter. In embodiments wherein transmigration of cells across the membrane (e.g. immune cells), is desired, pores of approximately 5 µm in diameter are particularly useful. In some embodiments, the pores can be irregularly spaced. In some embodiments, the pores can be regularly spaced. In some embodiments, the pores can be 5 µm or further apart, e.g. 5 µm apart, 10 µm, apart, 25 µm apart, 50 um apart, 100 µm apart, 1000 µm apart, 5 mm apart, or further apart.

In some embodiments, the membrane can be planar. In some embodiments, the membrane can be cylindrical. In some embodiments, the membrane is from 15 µm or greater in thickness, e.g. 15 µm or greater in thickness, 20 µm or greater in thickness, 25 µm or greater in thickness, 30 µm or greater in thickness, 35 µm or greater in thickness, or 40 µm or greater in thickness. In some embodiments, the membrane can be from 15 µm to 40 µm in thickness. In some embodiments, the membrane can be from 25 µm to 30 µm in thickness. In some embodiments, the membrane can be approximately 30 µm in thickness.

In some embodiments, a membrane 20 is attached to at least two membrane support elements 22, 24 in the fluid channel. As used herein, "a membrane support element" is a portion of the cell culture system to which the membrane is attached. A membrane support element can be a wall of the fluid channel or a separate structure such as a post, a series of posts, a clamp, or a port comprised by the fluid channel. In some embodiments, a membrane support element 22, 24 can change position, change orientation, and/or flex; thereby imparting a strain or movement to the membrane 20. In some embodiments, at least one membrane support element is coupled to a membrane strain mechanism. In some embodiments, a first membrane support element is coupled to a membrane strain mechanism and a second membrane support element is not coupled to a membrane strain mechanism. In some embodiments, two or more membrane support elements are coupled to a membrane strain mechanism. As used herein, a "membrane strain mechanism" refers to a means of causing a membrane support element 22, 24 to change position, change orientation, and/or flex; thereby causing a membrane to stretch in at least one direction. A membrane strain mechanism can cause the membrane to stretch by moving or flexing the membrane support element. Non-limiting examples of membrane strain mechanisms include vacuum chambers, fluid chambers connected to pumps, plungers, and the like.

As shown in FIGS. 3, 5, 6 and 12, the membrane strain mechanism can include one or more vacuum chambers 26 that cause the walls 22, 24 of the fluid channel 10 to flex outward causing the membrane 20 attached to the walls to be stretched between the walls 22, 24 of the fluid channel 10. In an alternative embodiment, the membrane 20 can be stretched between the walls 22, 24 of the fluid channel 10 in the rest position and a positive pressure can be applied to the chambers 26 to cause the walls 22, 24 to flex inward reducing and/or removing the strain on the membrane 20. Other mechanisms can be used to apply a strain to on the membrane 20. In accordance with the invention, additional pneumatic chambers can be provided around the fluid channel 10 in order to provide localized strain on the membrane 20 or strain the membrane 20 along different dimensions.

Figure 22A:
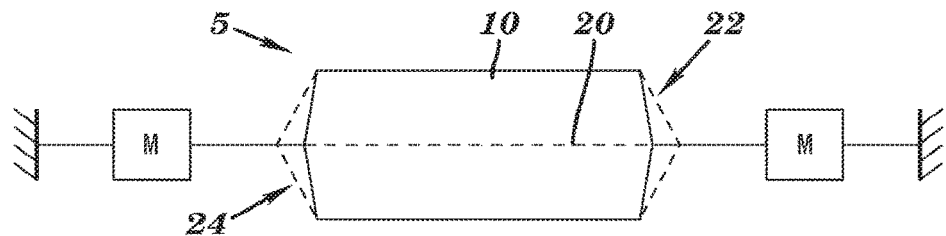
FIGS. 22A-22D depict some examples of alternative mechanisms that can be used to apply a strain on the membrane of the system described herein.

FIGS. 22A-22D show some examples of alternative mechanisms that can be used to apply a strain on the membrane 20. FIG. 22A shows one embodiment of the invention wherein the membrane 20 is attached to the walls 22, 24 of the device 5 and one or both of the walls 22, 24 are flexible and attached to a motor M that allows the walls to be flexed applying a strain on the membrane 20. In accordance with the invention, the motor M can be any device capable of applying a force on the walls 22, 24, including for example, a pneumatic or hydraulic cylinder, an electric motor and a lead screw or cable and pulley, or a solenoid. Where additional force is desired, mechanisms that utilize leverage and/or mechanical advantage, such as an over-center mechanism, can be used.

Figure 22B:
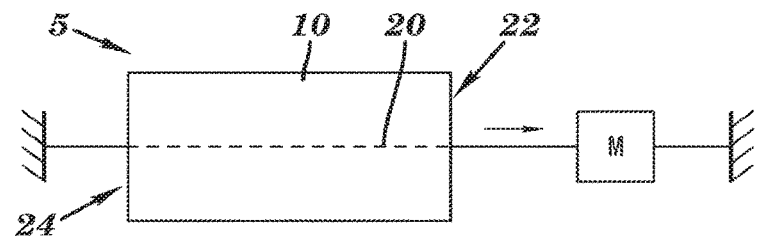

In accordance with an alternative embodiment of the invention, the motor M can be directly coupled to the membrane 20 which is free to be stretched, for example, through a slot or other opening in the fluid channel 10 as shown in FIG. 22B. Seals can be provided to prevent fluids from leaking out of the fluid channel 10. In some embodiments, the membrane can be coupled to a cable or cord that can be pulled taut to apply a strain on the membrane and one or more pulleys can be provided to enable the cable or cord to be tightened easily. The cable or cord can be tightened, for example, by winding the cable or cord around a pulley using an electric motor. In an alternative embodiment, the membrane 20 can be strained by winding it around a shaft extending parallel to one edge of the membrane 20.

Figure 22C:
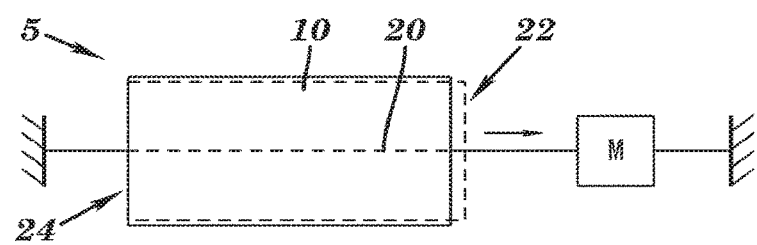

In accordance with an alternative embodiment of the invention, the fluid channel 10 can be formed from two rigid elements 22, 24, wherein one element 22 slides within the other element 24, as shown in FIG. 22C. As previously described, a motor M can be used to move element 22 relative to element 24 and apply a strain to the membrane 20 which is coupled or attached at opposite edges to elements 22 and 24. In some embodiment, a seal along the overlapping surfaces or a bellows can be used to seal the fluid channel 10.

Figure 22D:
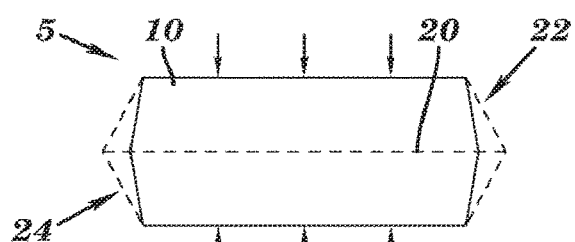

I accordance with an alternative embodiment of the invention, the fluid channel 10 can be formed of a flexible housing wherein the membrane 20 extends between two side walls 22, 24. In this embodiment, a force can be applied to the top and/or bottom of the fluid channel 10 causing the side walls 22 and 24 to flex outwardly straining the membrane 20. The forces causing the strain can be aided by the fluid flowing through the fluid channel 10 which will expand sideways the top and bottom walls come together. In this embodiment, as shown in FIG. 22D, the side walls 22 and 24 can be configured to flex along predefined portions of the side walls, for example where the side walls 22, 24 meet the top and bottom walls of the fluid channel 10 and where the membrane 20 is coupled or attached to the side walls 22, 24. In this embodiment, the pressure on the top and/or bottom of the fluid channel can be applied sequentially along the longitudinal axis of the fluid channel 10 that extends from the inlet ports to the outlet ports, for example, to simulate peristaltic motion.

In the embodiment shown in FIG. 5, the membrane support elements 22, 24 comprise a first and second wall of the fluid channel 10 and the membrane strain mechanisms 26 are vacuum chambers. The membrane is mounted to the first chamber wall (first membrane support element) 22 and the second chamber wall (second membrane support element) 24. Each operating channel 26 is located adjacent to each membrane support element 22, 24 such that the operating channel 26 is located on the opposing side of the membrane support element 22, 24 with reference to the to the fluid channel 10 and the other operating channel 26. A pressure differential (as compared to the fluid channel 10) is applied via vacuum to each operating channel 26, causing the membrane support element to flex in a desired direction and thus causing the membrane 20 to either expand or contract in that direction. Each operating channel 26 is connected to a vacuum system capable of providing the pressure differential. The operating channels 26 can be connected to the same vacuum system or to separate vacuum systems. The operating channel 26 can be connected to a vacuum system via a port in the operating channel and tubing.

In some embodiments, the membrane is caused to stretch from 0 to 50%. In some embodiments, the membrane is caused to stretch from 5% to 15%. In some embodiments, the membrane is caused to stretch approximately 10%. In some embodiments, the membrane can be caused to stretch more than 15% in order to create an abnormal condition and/or state of the intestinal epithelial cells. In some embodiments, the membrane is capable of being stretched more than 20%. In some embodiments, the membrane can be caused to stretch in an irregular or intermittent manner. In some embodiments, the membrane can be caused to stretch in a cyclic manner. In some embodiments, the membrane can be caused to stretch at a cyclic rate of from 0.01 Hz to 2 Hz. In some embodiments, the membrane can be caused to stretch at a cyclic rate of from 0.05 Hz to 0.25 Hz. In some embodiments, the membrane can be caused to stretch at a cyclic rate of less than 0.2 Hz. In some embodiments, the membrane can be caused to stretch at a cyclic rate of from 0.01 Hz to 0.18 Hz. In some embodiments, the membrane can be caused to stretch at a cyclic rate of approximately 0.15 Hz. In some embodiments, the membrane can be caused to stretch at a cyclic rate of 0.15 Hz. In some embodiments, the membrane can be caused to stretch at a cyclic rate of more than 0.2 Hz to create an abnormal condition and/or state of the intestinal epithelial cells, e.g. modeling hypercontractility of the bowels.

In some embodiments, the cell culture system can be a microfluidic system. As used herein, the term "microfluidic system" refers to a machine capable of the manipulation of microliter and/or nanoliter volumes of fluids. As depicted by the embodiment of the cell culture system presented in FIG. 12B, the microfluidic system can comprise a microfluidic chip 50 which can comprise at least the channel(s) and membrane elements of the cell culture system as described herein. In some embodiments of the invention, the size and shape of the chip 50 can be selected to enable the chip to be used in a particular microfluidic system. In some embodiments, the size, shape and configuration of the chip 50 can be selected so that the chip can be used as a replacement for other chips provided by manufacturers or suppliers for a particular microfluidic system. In some embodiments, the chip 50 can include one or more inlet ports 60 connected to one or more outlet ports 62 by one or more microfluidic channels 10. The ports 60, 62 can be provided in the appropriate size and shape necessary to accept the tubes and/or connectors of a particular microfluidic system. In some embodiments, the inlet port(s) 60 and the outlet port(s) 62 can be connected to enable fluid entering the inlet port(s)

60 to pass through some or all of the fluid channel(s) 10 before reaching the outlet port(s) 62. In some embodiments, multiple ports can be connected to a fluid channel. In the embodiment depicted in FIG. 12B, each of the two cell culture channels is 1,000 µm wide, 10,000 µm long, and 150 µm in height. The operating channels 44, 46 are 330 µm in height, 1,684 µm in width, and 9,089 µm in length. The membrane 20 is a 30 µm thick PDMS membrane with 10 µm diameter pores spaced 25 µm apart measured from center to center. In some embodiments, the chip 50 can be 15,000 µm in width; 25,000 µm in length; and 5,000 µm in height.

Figure 23:
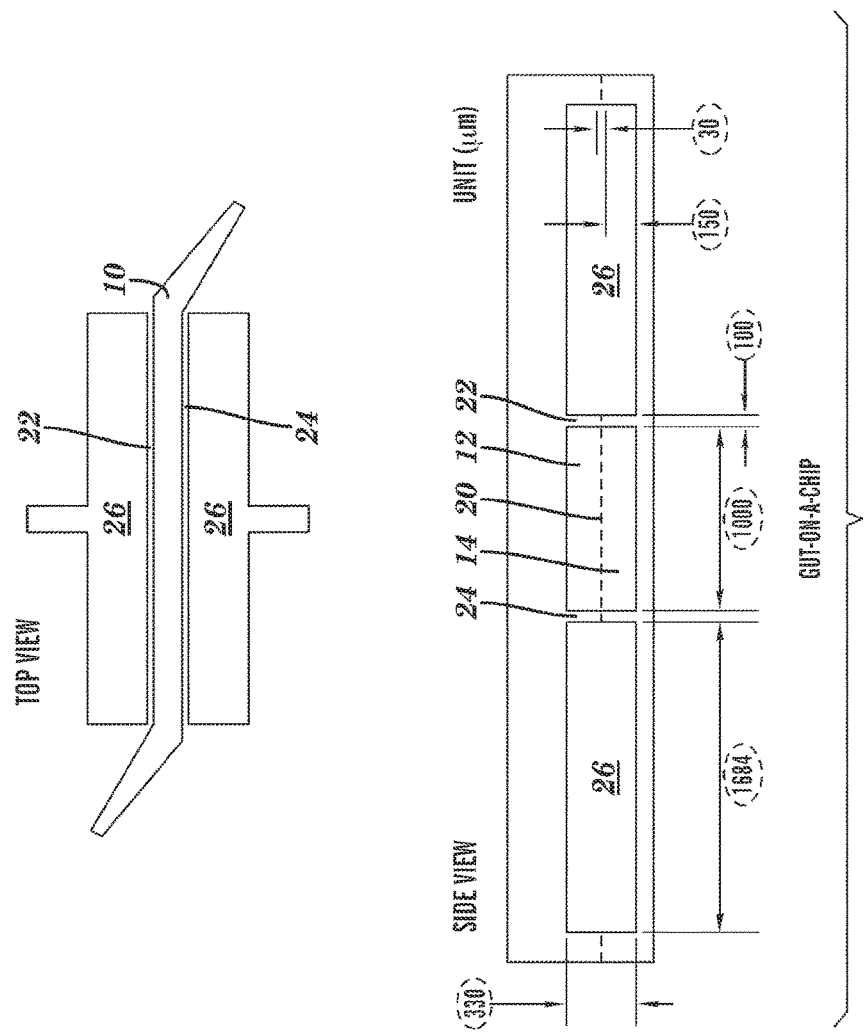
FIG. 23 depicts a schematic of one embodiment of the system described herein. Numbers in dashed circles are measurements of the specified features in m.

FIG. 23 depicts one embodiment of the system described herein. In this embodiment, the fluid channel 10 is 1,000 µm wide, 10,000 µm long, and 330 µm in height; the two cell culture channels are each 1,000 µm wide, 10,000 µm long, and 150 µm in height. The vacuum chambers 26 are 1,684 µm wide, 9,089 µm long, and 330 µm in height. The membrane 20 is a 30 µm thick PDMS membrane with 10 µm diameter pores spaced 25 µm apart measured from center to center.

The dimensions of the fluid channel 10 and cell culture channels 12 and 14 can be defined as ratios. In some embodiments, the height:width ratio of the fluid channel 10 can be 1:2 or greater, e.g. 1:2 or greater, 1:2.5 or greater, 1:3 or greater, or 1:35 or greater. In some embodiments, the height:width ration of the fluid channel 10 is approximately 1:3. In some embodiments, the height:width ratio of the fluid channel 10 can be 1:5 or greater, e.g. 1:5 or greater, 1:10 or greater, 1:20 or greater, or 1:30 or greater. In some embodiments, the height:width ratio of the fluid channel 10 can be approximately 1:30. In some embodiments, the ratio of the width of the fluid channel 10 to the width of the vacuum chamber 26 can be 1:0.75 or greater, e.g. 1:0.75 or greater, 1:1 or greater, 1:1.25 or greater, 1:1.5 or greater, or 1:1.75 or greater. In some embodiments, the ratio of the width of the fluid channel 10 to the width of the vacuum chamber 26 can be from 1:1 to 1:2. In some embodiments, the ratio of the width of the fluid channel 10 to the width of the vacuum chamber 26 can be approximately 1:1.68.

In some embodiments, the width:length ratio of a cell culture channel 12, 14 can be 1:5 or greater, e.g. 1:6 or greater, 1:7 or greater, 1:10 or greater, 1:15 or greater, 1:20 or greater, or 1:30 or greater. In some embodiments, the width:length ratio of a cell culture channel 12, 14 can be from 1:6 to 1:20. In some embodiments, the width:length ratio of a cell culture channel 12, 14 can be approximately 1:10. In some embodiments, the height:width ratio of a cell culture channel 12, 14 can be 1:5 or greater, e.g. 1:5 or greater, 1:6 or greater, 1:7 or greater, 1:8 or greater, 1:10 or greater, or 1:15 or greater. In some embodiments, the height:width ratio of a cell culture channel 12, 14 can be from 1:5 to 1:10. In some embodiments, the height:width ratio of a cell culture channel 12, 14 can be approximately 1:6.67. In some embodiments, the height:length ratio of a cell culture channel 12, 14 can be 1:20 or greater, e.g. 1:20 or greater, 1:25 or greater, 1:30 or greater, 1:40 or greater, 1:50 or greater, 1:60 or greater, 1:70 or greater, 1:80 or greater, or 1:100 or greater. In some embodiments, the height:length ratio of a cell culture channel 12, 14 can be from 1:20 to 1:100. In some embodiments, the height:length ratio of a cell culture channel 12, 14 can be approximately 1:66.67.

Figure 12C:
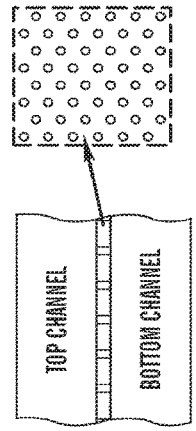
FIGS. 12A-12E depict one embodiment of the human Gut-on-a-Chip device.
Figure 12B:
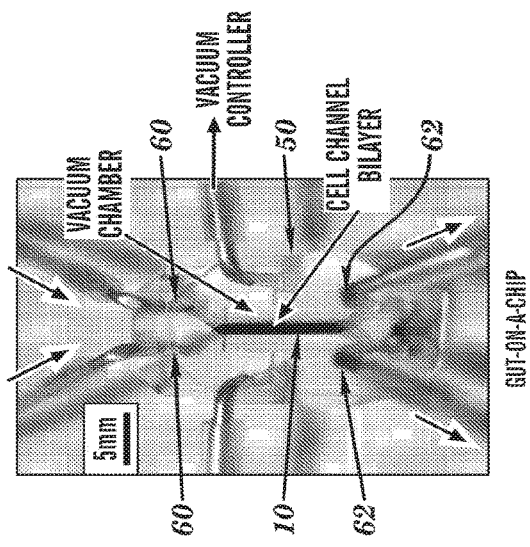
Figure 12A:
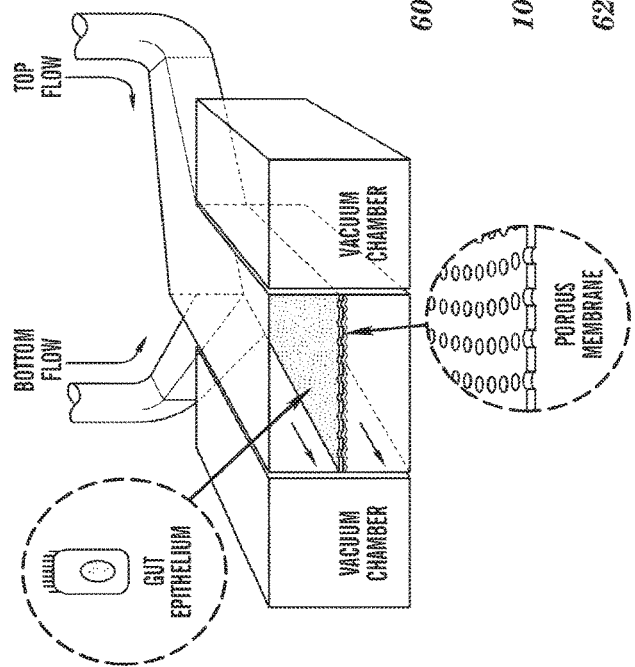
Figure 12E:
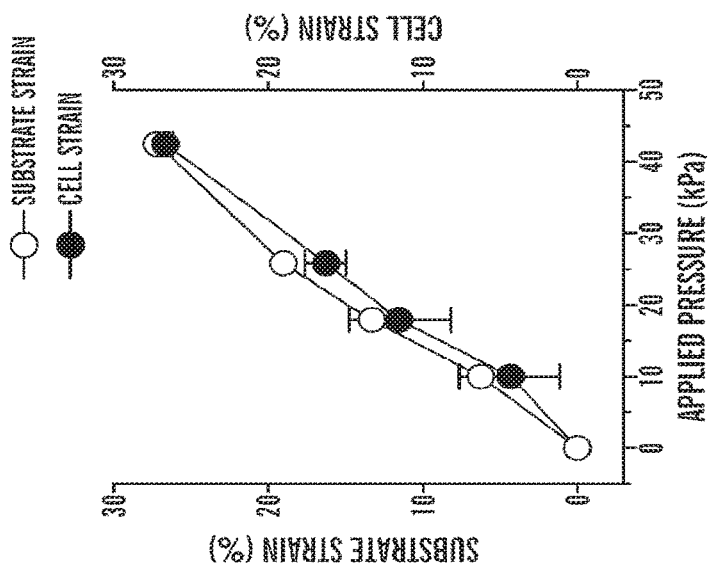
Figure 12D:
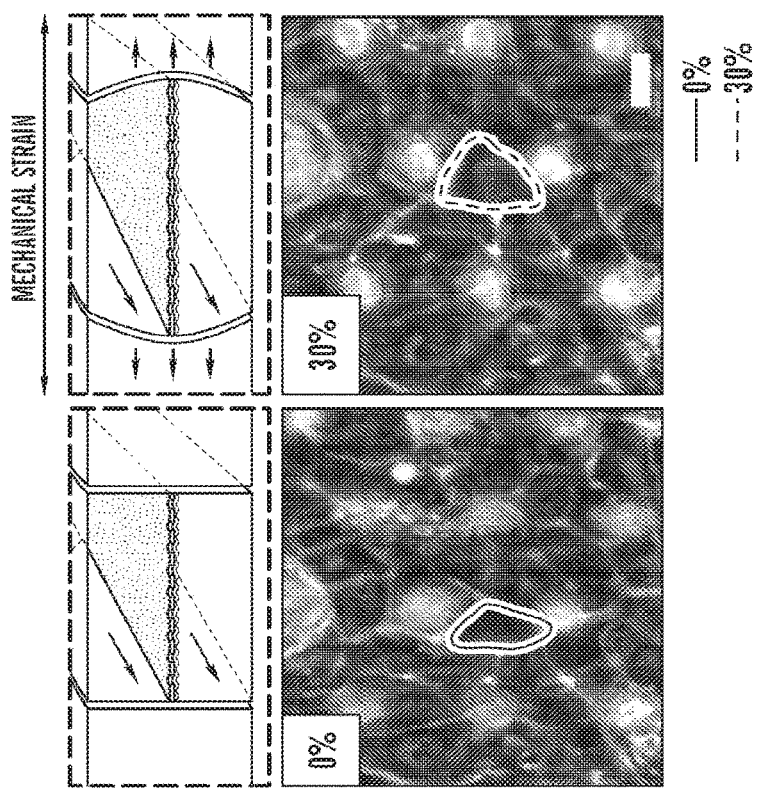
Figure 13:
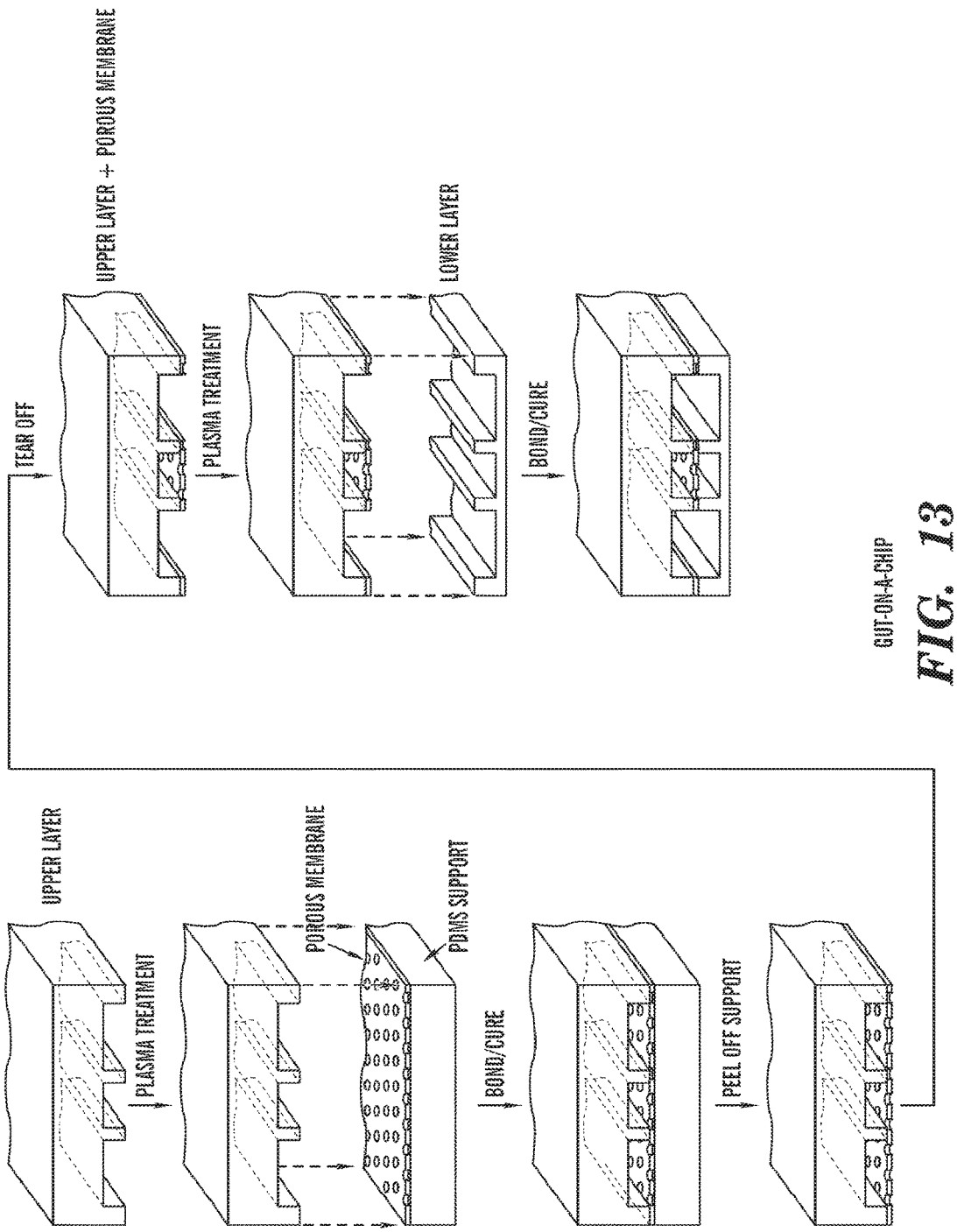
FIG. 13 depicts a schematic of the microfabrication process of one embodiment of the device described herein. The Gut-on-a-Chip microdevice can be fabricated from three PDMS layers (an upper layer, a porous membrane, and a lower layer), which are sequentially bonded and modified to create the central cell culture channel with upper (blue) and lower (orange) channels, and two lateral vacuum chambers. The regions of the porous PDMS membrane that spanned the vacuum chambers (grey) can be physically torn off during the process to create full height chambers.

The structures of the cell culture system described herein (e.g. the membrane, ports and/or the membrane support structures) can be formed, such as by etching, 3-D printing, machining, or micro-machining. In some embodiments, the cell culture system described herein is etching-free. In one embodiment, the embodiment of the cell culture system depicted in FIG. 12B can be formed as follows. The cell culture system can be fabricated from a flexible clear polydimethylsiloxane (PDMS; Sylgard, Dow Corning) polymer. The aligned upper and lower microchannels can be of the same size (150 µm high×1,000 µm wide) and separated by a 30 µm thick PDMS membrane containing 10 µm diameter circular pores with a 25 µm spacing (center to center) (FIGS. 12A-12C). As shown in FIG. 13, the upper and lower microchannel layers can be individually prepared by casting PDMS prepolymer (15:1 w/w ratio of PDMS to curing agent) on a microfabricated mold of the inverse channel design made of photoresist (SU-8 100, Microchem, Newton, Mass.). The porous membrane (FIG. 12C, right inset) can be prepared by casting PDMS prepolymer on a microfabricated silicon wafer containing post arrays with circular pillars (10 µm diameter×30 µm high with 25 µm spacing; MEMS and Nanotechnology Exchange, Reson, Va.), overlaying the prepolymer with a cured, flat, silanized PDMS support layer, placing a 3 kg weight on the setup, and curing the polymer at 60° C. for 12 hours. After peeling the porous PDMS membrane and support layer from the wafer, the surface of the porous membrane can be exposed to plasma generated by a laboratory corona treater (BD-20AC, Electro-Technic Products, Inc., Chicago, Ill.), as can be the upper microchannel layer. The plasma-treated surfaces of the porous PDMS membrane and upper microchannel layer can be then immediately placed in conformal contact. Incubation of the whole setup at 80° C. overnight results in irreversible bonding of the two PDMS layers. The PDMS support layer can be then peeled off the bottom of the PDMS porous membrane and portions of this membrane located over the lateral vacuum chambers can be torn off using forceps to make full-height hollow vacuum chambers. The exposed surface of the torn PDMS membrane and top surface of a lower PDMS microchannel layer with same shape to the upper layer can then be exposed to plasma, aligned, pressed together under a stereoscope (Zeiss Discovery V20 Stereo Microscope, Carl Zeiss MicroImaging Gmb, Germany), and cured at 80° C. overnight to produce the entire bonded device containing hollow vacuum chambers on either side of the main microchannel (FIG. 12A and FIG. 13). Tubing (Tygon 3350 silicone tubing, ID ½2", OD ³⁄₃₂", Beaverton, Mich.) can be connected from fluid medium and vacuum sources to the upper and lower microfluidic channels, respectively, using hub-free stainless steel blunt needles (18G; Kimble Chase, Vineland, N.J.). This allows control of the flow of culture medium within the central microchannel, and regulation of the application of vacuum to the side chambers under computer control to exert cyclic mechanical strain to mimic peristaltic motions (FIG. 12D).

The cell culture system described herein can be made of a biocompatible flexible material or a biocompatible non-flexible material according to the design and application requirements. It should be noted that the designs depicted in the Figures are exemplary and the cell culture system described herein is not limited to the configurations shown in the Figures. The cell culture system and/or portions thereof can be made of a flexible material, including but not limited to, a biocompatible material such as polydimethyl siloxane (PDMS), polyurethane or polyimide. The cell culture system and/or portions thereof can also be made of non-flexible materials like glass, silicon, polysulfone, hard plastic, and the like, as well as combinations of these materials.

A biocompatible polymer refers to materials which do not have toxic or injurious effects on biological functions. Biocompatible polymers include natural or synthetic polymers. Examples of biocompatible polymers include, but are not limited to, collagen, poly(alpha esters) such as poly (lactate acid), poly(glycolic acid), polyorthoesters and polyanhydrides and their copolymers, polyglycolic acid and polyglactin, cellulose ether, cellulose, cellulosic ester, fluorinated polyethylene, phenolic, poly-4-methylpentene, polyacrylonitrile, polyamide, polyamideimide, polyacrylate, polybenzoxazole, polycarbonate, polycyanoarylether, polyester, polyestercarbonate, polyether, polyetheretherketone, polyetherimide, polyetherketone, polyethersulfone, polyethylene, polyfluoroolefin, polyimide, polyolefin, polyoxadiazole, polyphenylene oxide, polyphenylene sulfide, polypropylene, polystyrene, polysulfide, polysulfone, polytetrafluoroethylene, polythioether, polytriazole, polyurethane, polyvinyl, polyvinylidene fluoride, regenerated cellulose, silicone, urea-formaldehyde, polyglactin, or copolymers or physical blends of these materials.

A biocompatible material can also be, for example, ceramic coatings on a metallic substrate. But any type of coating material and the coating can be made of different types of materials: metals, ceramics, polymers, hydrogels or a combination of any of these materials. Biocompatible materials include, but are not limited to an oxide, a phosphate, a carbonate, a nitride or a carbonitride. Among the oxide the following ones are preferred: tantalum oxide, aluminum oxide, iridium oxide, zirconium oxide or titanium oxide. Substrates are made of materials such as metals, ceramics, polymers or a combination of any of these. Metals such as stainless steel, Nitinol, titanium, titanium alloys, or aluminum and ceramics such as zirconia, alumina, or calcium phosphate are of particular interest.

The biocompatible polymer may be shaped using methods such as, for example, solvent casting, compression molding, filament drawing, meshing, leaching, weaving and coating. In solvent casting, a solution of one or more polymers in an appropriate solvent, such as methylene chloride, is cast as a branching pattern relief structure. After solvent evaporation, a thin film is obtained. In compression molding, a polymer is pressed at pressures up to 30,000 pounds per square inch into an appropriate pattern. Filament drawing involves drawing from the molten polymer and meshing involves forming a mesh by compressing fibers into a felt-like material. In leaching, a solution containing two materials is spread into a shape close to the final form of the RUG. Next a solvent is used to dissolve away one of the components, resulting in pore formation. (See Mikos, U.S. Pat. No. 5,514,378, hereby incorporated by reference). In nucleation, thin films in the shape of a RUG are exposed to radioactive fission products that create tracks of radiation damaged material. Next the polycarbonate sheets are etched with acid or base, turning the tracks of radiation-damaged material into pores. Finally, a laser may be used to shape and burn individual holes through many materials to form a RUG structure with uniform pore sizes. Coating refers to coating or permeating a polymeric structure with a material such as, for example liquefied copolymers (poly-DL-lactide co-glycolide 50:50 80 mg/ml methylene chloride) to alter its mechanical properties. Coating may be performed in one layer, or multiple layers until the desired mechanical properties are achieved. These shaping techniques may be employed in combination, for example, a polymeric matrix may be weaved, compression molded and glued together. Furthermore different polymeric materials shaped by different processes may be joined together to form a composite shape. The composite shape may be a laminar structure. For example, a polymeric matrix may be attached to one or more polymeric matrixes to form a multilayer polymeric matrix structure. The attachment may be performed by gluing with a liquid polymer or by suturing. In addition, the polymeric matrix may be formed as a solid block and shaped by laser or other standard machining techniques to its desired final form. Laser shaping refers to the process of removing materials using a laser.

The fluid which is caused to flow through the one or more fluid channels of the cell culture system described herein can be any fluid appropriate for maintaining or culturing intestinal cells. In some embodiments, the fluid channel is divided into a first cell culture channel and a second cell culture channel and the same fluid or different fluids can be caused to flow through each channel. If the first cell culture channel comprises intestinal epithelial cells, the fluid flowing through the first cell culture channel can be a fluid appropriate for maintaining or culturing intestinal epithelial cells. If the second cell culture channel comprises endothelial cells, immune cells, and/or connective tissue cells, the fluid flowing through the second cell culture channel can be a fluid appropriate for maintaining or culturing endothelial cells, immune cells, and/or connective tissue cells. If microbial cells are present in the cell culture system, the fluid should be appropriate for maintaining or culturing microbial cells, e.g. it should not contain antibiotics to which the microbial cells are susceptible. Fluids can comprise cell culture medium, solutions, buffers, nutrients, tracer compounds, dyes, antimicrobials, or other compounds not toxic to the cells being cultured in the cell culture system described herein. One of ordinary skill in the art is well aware of suitable fluids for culturing or maintaining intestinal cells, intestinal epithelial cells, endothelial cells, immune cells, and/or connective tissue cells, and microbial cells. By way of non-limiting example, fluids suitable for maintaining or culturing intestinal epithelial cells can include; Dulbecco's Modified Eagle Medium containing 4.5 g/L glucose (DMEM; Gibco, Grand Island, N.Y.) supplemented with 20% fetal bovine serum (FBS; Gibco), 100 units/mL penicillin, 100 µg/mL streptomycin (Gibco), 100 µg/mL Normocin (Invivogen, San Diego, Calif.), and 25 mM HEPES or Dulbecco's Modified Eagle Medium containing 4.5 g/L glucose (DMEM; Gibco, Grand Island, N.Y.) supplemented with 20% fetal bovine serum (FBS; Gibco), and 25 mM HEPES.

In some embodiments, the fluid flowing through the one or more chambers of the cell culture system is subject to shear stress. In some embodiments, the fluid flow and/or design of the system can be modulated to achieve a desired shear stress. In some embodiments, the shear stress experienced by the fluid in the one or more chambers of the cell culture system can be a shear stress equivalent to that encountered in the intestine of a mammal. In some embodiments, the shear stress experienced by the fluid in the one or more chambers of the cell culture system can be a shear stress equivalent to that encountered in the intestine of a mammal suffering from an intestinal disorder. By way of non-limiting example, an intestinal disorder could be a disease or a blockage. In some embodiments, the shear stress can be less than or equal to 0.3 dyne/cm$^2$. In some embodiments, the shear stress can be less than 0.1 dyne/cm$^2$. In some embodiments, the shear stress can be from 0.0008 to 0.08 dyne/cm$^2$. In some embodiments, the shear stress can be from 0.010 to 0.026 dyne/cm$^2$. In some embodiments, the shear stress can be approximately 0.018 dyne/cm$^2$. In some embodiments, the shear stress and/or the fluid flow rate can be modulated to create an abnormal state and/or condition of the intestinal epithelial cells, e.g. modeling "flush-out" of the luminal components of the intestine.

In some embodiments, the shear stress can be approximately the same for the duration of the time during which intestinal epithelial cells are cultured in the cell culture system. In some embodiments, the shear stress can be increased and/or decreased during the time in which intestinal epithelial cells are cultured in the cell culture system, e.g. the shear stress can be decreased for a time to allow newly added cells to attach to the membrane and/or pre-existing cells. In some embodiments, the shear stress can be varied in a regular, cyclic pattern. In some embodiments the shear stress can be varied in an irregular pattern. In some embodiments, the shear stress can vary over time from 0 to 1000 dyne/cm$^2$. In some embodiments, the shear stress can vary over time from 0.0008 to 0.08 dyne/cm$^2$.

In some embodiments, the fluid flow rate through the one or more channels of the cell culture system described herein can be a fluid flow rate equivalent to that encountered in the intestine of a mammal. In some embodiments, the fluid flow rate in the one or more chambers of the cell culture system can be a fluid flow rate equivalent to that encountered in the intestine of a mammal suffering from an intestinal disorder. By way of non-limiting example, an intestinal disorder could be a disease or a blockage. In some embodiments, the fluid flow rate can be less than or equal to 500 µL/hr, e.g. it can be 500 µL/hr, 400 µL/hr, 300 µL/hr, 200 µL/hr, 100 µL/hr, 50 µL/hr, 10 µL/hr or less. In some embodiments, the fluid flow rate can be less than or equal to 100 µL/hr. In some embodiments, the fluid flow rate can be less than or equal to 50 µL/hr. In some embodiments, the fluid flow rate can be from 0 to 50 µL/hr. In some embodiments, the fluid flow rate can be less than 40 µL/hr. In some embodiments, the fluid flow rate can be less than 35 µL/hr. In some embodiments, the fluid flow rate can be from 0 to 39 µL/hr. In some embodiments, the fluid flow rate can be from 0 to 35 µL/hr. In some embodiments, the fluid flow rate can be from 0 to 30 µL/hr. In some embodiments, the fluid flow rate can be approximately 30 µL/hr. In some embodiments, the fluid flow rate can be approximately the same for the duration of the time during which intestinal epithelial cells are cultured in the cell culture system. In some embodiments, the fluid flow rate can be increased and/or decreased during the time in which intestinal epithelial cells are cultured in the cell culture system, e.g. the fluid flow rate can be decreased for a time to allow newly added cells to attach to the membrane and/or pre-existing cells. In some embodiments, the fluid flow rate can be varied in a regular, cyclic pattern. In some embodiments the fluid flow rate can be varied in an irregular pattern.

In some embodiments, control of the fluid flow from the fluid source through the fluid channel 10 or the membrane strain mechanism 26 can be automated. In an embodiment in which control of the flow of solution from the fluid source or the membrane strain mechanism is automated, a syringe pump or solenoid can be used. In other embodiments, one or more computing devices or systems may be used to control fluid flow or a membrane strain mechanism 26. Alternatively or additionally, a computing device may be coupled to fluid source or port 60 in order to control the flow of fluid from the fluid source. Alternatively or additionally, a computing device may be coupled to a membrane strain mechanism to automate movement of a membrane support element 22, 24 and stretching of the membrane 20. For example, a computing device may be used to control the pressure in a vacuum operating channel.

Figure 20:
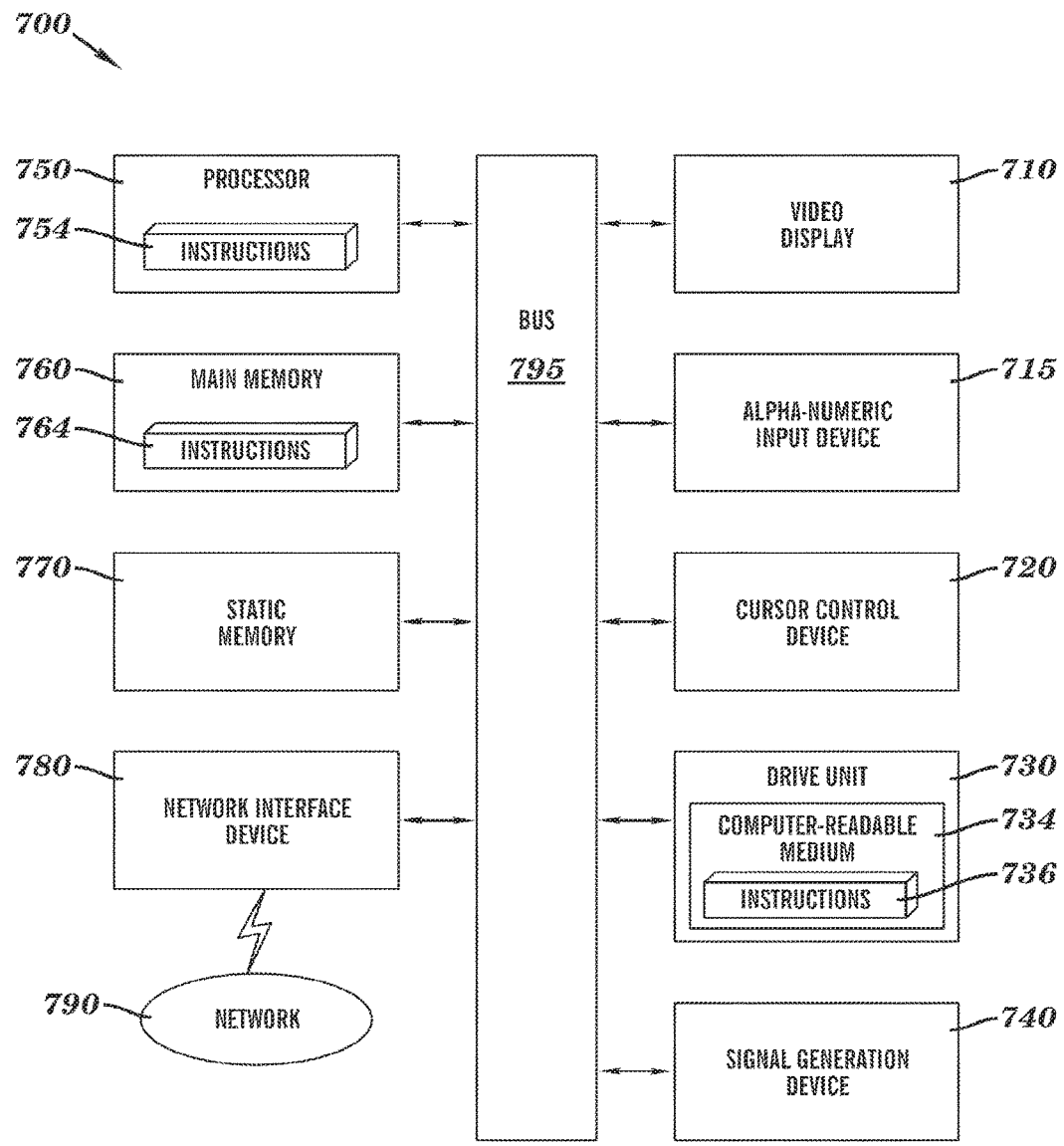
FIG. 20 depicts a schematic of computer systems suitable for automated control of the systems described herein.

FIG. 20 shows a diagrammatic representation of machine in the exemplary form of computer system 700 within which a set of instructions, for causing the machine to perform such control of fluid flow or membrane stretching as discussed herein, may be executed. In alternative embodiments, the machine operates as a standalone device or may be connected (e.g., networked) to other machines. The machine may comprise a personal computer (PC), a tablet, a Personal Digital Assistant (PDA), a cellular telephone, a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

According to some embodiments, computer system 700 comprises processor 750 (e.g., a central processing unit (CPU), a graphics processing unit (GPU) or both), main memory 760 (e.g., read only memory (ROM), flash memory, dynamic random access memory (DRAM) such as synchronous DRAM (SDRAM) or Rambus DRAM (RDRAM), etc.) and/or static memory 770 (e.g., flash memory, static random access memory (SRAM), etc.), which communicate with each other via bus 795.

According to some embodiments, computer system 700 may further comprise video display unit 710 (e.g., a liquid crystal display (LCD), a light-emitting diode display (LED), an electroluminescent display (ELD), plasma display panels (PDP), an organic light-emitting diode display (OLED), a surface-conduction electron-emitted display (SED), a nanocrystal display, a 3D display, or a cathode ray tube (CRT)). According to some embodiments, computer system 700 also may comprise alphanumeric input device 715 (e.g., a keyboard), cursor control device 720 (e.g., a mouse or controller), disk drive unit 730, signal generation device 740 (e.g., a speaker), and/or network interface device 780.

Disk drive unit 730 includes computer-readable medium 734 on which is stored one or more sets of instructions (e.g., software 736) embodying any one or more of the methodologies or functions described herein. Software 736 may also reside, completely or at least partially, within main memory 760 and/or within processor 750 during execution thereof by computer system 700, main memory 760 and processor 750. Processor 750 and main memory 760 can also constitute computer-readable media having instructions 754 and 764, respectively. Software 736 may further be transmitted or received over network 790 via network interface device 780.

While computer-readable medium 734 is shown in an exemplary embodiment to be a single medium, the term "computer-readable medium" should be taken to include a single medium or multiple media (e.g., a centralized or distributed database, and/or associated caches and servers) that store the one or more sets of instructions. The term "computer-readable medium" shall also be taken to include any medium that is capable of storing, encoding or carrying a set of instructions for execution by the machine and that cause the machine to perform any one or more of the methodologies of the disclosed embodiments. The term "computer-readable medium" shall accordingly be taken to include, but not be limited to, solid-state memories, and optical and magnetic media.

It should be understood that processes and techniques described herein with respect to automated control of fluid flow and membrane strain mechanisms are not inherently related to any particular apparatus and may be implemented by any suitable combination of components. Further, various types of general purpose devices may be used in accordance with the teachings described herein. It may also prove advantageous to construct a specialized apparatus to perform the functions described herein. Those skilled in the art will appreciate that many different combinations of hardware, software, and firmware will be suitable for practicing the disclosed embodiments.

In some embodiments, at least one side of the membrane is coated with at least one type of attachment molecule that supports the adhesion of a plurality of living cells. In some embodiments, one side of the membrane is coated with at least one type of attachment molecule that supports the adhesion of a plurality of living cells. In some embodiments, two sides of the membrane are coated with at least one type of attachment molecule that supports the adhesion of a plurality of living cells. In some embodiments, one or more types of attachment molecules are coating the membrane, e.g. one type of attachment molecule, two types of attachment molecules, three types of attachment molecules, four types of attachment molecules, or more types of attachment molecules. In some embodiments, the attachment molecule is applied to the membrane as a gel, solution, hydrogel, or other composition that will adhere to the membrane via without chemically binding the membrane. In some embodiments, the attachment molecule is chemically coupled to the membrane, e.g. covalently bond or cross-linked. In some embodiments, the membrane is created (e.g. polymerized) with attachment molecules embedded in the membrane. In some embodiments, the attachment molecule can be a component of the extracellular matrix. In some embodiments, the attachment molecule can be a molecule bound by a molecule on the surface of an intestinal epithelial cell. In some embodiments, the attachment molecule can be a molecule which binds a molecule on the surface of an intestinal epithelial cell. Non-limiting examples of types of attachment molecules include collagen; collagen Type I, collagen Type II; collagen Type III; collagen Type IV; collagen Type V; collagen Type VI; collagen Type VII; collagen Type VIII; collagen Type IX, collagen Type X; collagen Type XI; collagen Type XII; collagen Type XIII; collagen Type XIV; extracellular matrix, MATRIGEL™; laminin; proteoglycan; vitronectin; fibronectin; poly-D-lysine; elastin; hyaluronic acid; glycoasaminoglycans; integrin; polypeptides, oligonucleotides, DNA, and/or polysaccharide. In some embodiments, the attachment molecule is obtained from a mammal. In some embodiments, the attachment molecule is synthesized or obtained from a transgenic organism. In some embodiments, the attachment molecule is human in origin. In some embodiments, the attachment molecule is mammalian in origin e.g. murine or primate in origin. One of ordinary skill in the art is well aware of methods of synthesizing or producing the carbohydrates and peptide sequences of attachment molecules. Attachment molecules are also available commercially, e.g. MATRIGEL™ (Cat No 356234; BD Biosciences Franklin Lakes, N.J.) or laminin (Cat No. 354232; BD Biosciences Franklin Lakes, N.J.). In some embodiments, the concentration of an attachment molecule can be from 10 µg/mL to 1,000 µg/mL, e.g., 10 µg/mL, 50 µg/mL, 100 µg/mL, 200 µg/mL, 300 µg/mL, 500 µg/mL, 1,000 µg/mL or any value in between. In some embodiments, the membrane is coated with a mixture comprising collagen type I and MATRIGEL™. In some embodiments, the membrane is coated with a mixture comprising 50 µg/mL collagen type I and 300 µg/mL MATRIGEL™. In some embodiments, the membrane is coated with a 1:1 (v:v) mixture comprising 50 µg/mL collagen type I and 300 µg/mL MATRIGEL™. In some embodiments, the membrane is coated with a 1:1 (v:v) mixture comprising 50 µg/mL collagen type I and 300 µg/mL MATRIGEL™ dissolved in serum-free DMEM. In some embodiments, the membrane is coated with a 1:1 (v:v) mixture comprising 50 µg/mL collagen type I from rat and 300 µg/mL MATRIGEL™ dissolved in serum-free DMEM.

In some embodiments of the cell culture system described herein, at least one layer of intestinal epithelial cells is attached to at least one surface of the membrane. In some embodiments, one or more layers of intestinal epithelial cells are attached to the membrane, e.g. one layer, two layers, three layers, or more layers of intestinal epithelial cells. In some embodiments, intestinal epithelial cells are attached to one side of the membrane. In some embodiments, intestinal epithelial cells are attached to two sides of the membrane. In some embodiments, the intestinal epithelial cells are mammalian cells. In some embodiments, the intestinal epithelial cells are human cells. In some embodiments, the intestinal epithelial cells are primary cells, primary small intestine cells, primary large intestine cells, small intestine cells, large intestine cells, cultured cells, passaged cells, immortalized cells, transgenic cells, genetically modified cells, cancerous cells or cells from an animal with an intestinal cancer, cells from an animal with an intestinal disease or disorder, stem cells, embryonic stem cells (ESCs), induced pluripotent stem cells (IPSCs), paneth cells, crypt cells, mucus-secreting cells, Caco2 cells, or HT-29 cells. In some embodiments, the intestinal epithelial cells in the cell culture system described herein comprise villi structures.

In some embodiments, the cell culture system described herein comprises a first cell culture channel and a second cell culture channel, wherein the first cell culture channel comprises intestinal epithelial cells. In some embodiments, the cell culture system described herein comprises a first cell culture channel and a second cell culture channel, wherein the first cell culture channel comprises intestinal epithelial cells and the second cell culture channel comprises endothelial cells, immune cells, muscle cells and/or connective tissue cells. In some embodiments, the cells in a cell culture channel are attached to the surface of the membrane exposed to that cell culture channel.

In some embodiments, one or more layers of endothelial cells, immune cells, and/or connective tissue cells are attached to the membrane, e.g. one layer, two layers, three layers, or more layers of endothelial cells, immune cells, and/or connective tissue cells. In some embodiments, the endothelial cells are intestinal endothelial cells. In some embodiments, the endothelial cells are capillary endothelial cells. In some embodiments, the endothelial cells are lymphatic endothelial cells. In some embodiments, the endothelial cells, immune cells, and/or connective tissue cells are mammalian cells. In some embodiments, the endothelial cells, immune cells, and/or connective tissue cells are human cells. In some embodiments, the endothelial cells, immune cells, and/or connective tissue cells are primary cells, primary small intestine cells, primary large intestine cells, fibroblasts, small intestine cells, large intestine cells, cultured cells, passaged cells, immortalized cells, transgenic cells, genetically modified cells, cancerous cells or cells from an animal with an intestinal and/or endothelial cancer, cells from an animal with an intestinal disease or disorder, stem cells, embryonic stem cells (ESCs), or induced pluripotent stem cells (IPSCs).

As used herein, an "immune cell" is any cell of the immune system involved in adaptive or humoral immunity. Non-limiting examples of immune cells include peripheral blood mononuclear cells (PBMC), plasmacytoid dendritic cells (PDC), myeloid dendritic cells (MDC), B cells, macrophages, monocytes, natural killer cells, NKT cells, CD4+ T cells, CD8+ T cells, granulocytes or precursors thereof.

As used herein, a "connective cell" refers to those animal tissues that support organs, fill spaces between them, or perform mechanical functions such as connecting muscles to bone (tendons and ligaments) or providing low friction weighing surface as in articular cartilage. Connective tissues are characterized by their relatively avascular matrices and low cell densities. The most abundant connective tissues are the reticular stroma, muscle, adipose tissue, cartilage and bone. Further examples of connective tissue include, but are not limited to, mesenchyme, mucous connective, areolar (loose), elastic, or blood. Included within the definition of "connective tissue" are terminally differentiated cells as well as precursor cells that have the potential to differentiate into connective tissue cells and tissues.

In some embodiments, the cell culture system described herein comprises microbial cells and/or pathogens. In some embodiments, the microbial cells and/or pathogens can be present in the same cell culture channel as the intestinal epithelial cells. In some embodiments, the microbial cells and/or pathogens can be present in the first cell culture channel. In some embodiments, the microbial cells can be microbial cells found in the intestine or gut of a healthy animal. In some embodiments, the microbial cells and/or pathogens can be organisms found in the intestine or gut of an unhealthy animal, e.g. one with an intestinal disease or disorder. In some embodiments, the microbial cells and/or pathogens can be organisms that cause or contribute to a disease or disorder of the intestine.

In some embodiments, the microbial cells are aerobic. In some embodiments, the microbial cells are anaerobic. In some embodiments, the cell culture system described herein comprises both aerobic and anaerobic microbial cells. In some embodiments, the microbial cells are cultured in the cell culture system described herein for at least 1 day. The culture of microbial cells in the cell culture systems described herein can be used to model and/or recapitulate the microflora environment of the intestine. In some embodiments, the culture of microbial cells in the cell culture systems described herein does not reduce the viability of the intestinal epithelial cells, e.g. the viability of the intestinal epithelial cells is reduced by less than 10% after the introduction of microbial cells to the cell culture system.

Microbial cells can be bacterial cells, including both gram positive and gram negative bacteria. Non-limiting examples of bacterial cells useful in the cell culture system described herein include *Lactobacillus; Bacterioides; Ruminococcus; Peptococcus; Peptostreptococcus; Bifidobacterium; Escherichia; Achromobacter; Acidaminococcus fermentans; Acinetobacter cacoaceticus; Aeromonas; Alcaligenes faecalis; Bacillus; Butyriviberio fibrosolvens; Camplyobacter; Campylobacter coli, Clostridium difficile; Clostridium sordelli; Enterobacter cloacae; Enterococcus faecalis; Enterococcus faecium; Escherichia coli; Flavobacterium; Mycobacterium; Mycoplasma; Plesiomonas shigelloides; Propionibacterium acnes; Pseudomonas aeruginosa; Ruminococcus bromii; Sarcina; Staphylococcus aureus; Streptococcus anginosus; Veillonella; Vibrio; Yersinia enterocolitica; Lactobacillus rhamnosus, Lactobacillus rhamnosus GG; Bifidobacterium breve; Bifidobacterium longum; Bifidobacterium infantis; Lactobacillus acidophilus; Lactobacillus plantarum; Lactobacillus paracasei; Lactobacillus bulgaricus; and Streptococcus thermophilus.*

In some embodiments, the microbial cells are pathogenic. In some embodiments, the microbial cells are intestinal pathogens. Non-limiting examples of pathogenic microbial cells include, enterotoxigenic *Escherichia coli; Bilophila wadsworthia; Shigella; Yersinia; Pleisiomonas; Vibrio; Aeromonas; Campylobacter; Crytosporidia; Coccidosis; Salmonella; Helicobacter pylori; Clostridium difficile; Salmonella kedougou; Bacteroides; Clostridium; Firmicutes; Shigellia dysenteriae; Salmonella enterica; Salmonella typhi; Listeria; Listeria monocytogenes; Vibrio parahaemolyticus; Proteus; Vibrio cholerae; Enterococcus faecalis; Yersinia enterocolitica;* and *Campylobacter jejuni.* Intestinal pathogens have been well studied and described (see for example. Microbial Pathogenesis and the Intestinal Epithelial Cell—Gail A. Hecht—2003—ASM press). Intestinal pathogens described in this book are hereby incorporated by reference.

In some embodiments, the cell culture system comprises pathogens. As used herein, "pathogens" can include viruses, bacteria, fungi, and parasites which are known to cause or be associated with any disorder or disease of the intestine. Microbial pathogens are discussed above herein. Non-limiting examples of viral intestinal pathogens include rotavirus; norwalk-like viruses; adenoviruses; astroviruses; sapporo-like viruses; toroviruses; coronaviruses; picornaviruses; herpes viruses; and noroviruses. Non-limiting examples of fungal intestinal pathogens include *Candida, Aspergillus*, and *Candida albicans*. Non-limiting examples, of intestinal parasites include single-celled parasites, multi-celled parasites, ameobas, worms, tape worms, protozoans, flukes (flatworms), roundworms, pinworms, hookworms, Giradia *lamblia, cryptosporidium*, and *Entamoeba histolytica.*

In some embodiments of the cell culture system described herein, the system can comprise an anaerobic gas chamber in contact with at least part of the first cell culture channel. In some embodiments, the anaerobic gas chamber comprises a portion of the first cell culture which is not occupied by fluid. In some embodiment, the anaerobic gas chamber is a void or space in the cell culture system above the first cell culture channel and having at least one port, gap or other means of contacting the upper surface of the fluid in the first cell culture channel. In some embodiments, an oxygen gradient is established in the fluid flowing through the first cell culture channel. In some embodiments, anaerobic and/or hypoxic conditions can be created in the first cell culture channel by sealing first cell culture channel after intestinal epithelial and optionally, microbial cells, have been introduced, so that the only points of entry or exit to the first cell culture channel are the pores in the membrane. Fluid can then be provided to the second cell culture channel. The fluid provided to the second cell culture channel can be oxygenated or deoxygenated.

In some embodiments, the fluid provided to at least the first cell culture channel is deoxygenated prior to entering the first cell culture channel. Deoxygenation can be accomplished, by way of non-limiting example, by vacuum degasification, membrane degasification, substitution by inert gas, or contacting the solution with a reductant. In some embodiments, the first cell culture channel. In some embodiments, the level of oxygen in the fluid flowing through the first cell culture channel is $8\times10^{-2}$ mol/L or less; e.g. $4\times10^{-2}$ mol/L or less; $8\times10^{-3}$ mol/L or less; or $4\times10^{-3}$ mol/L or less. In some embodiments, the level of oxygen is the same in each cell culture channel. In some embodiments, an anaerobic, inert gas is caused to flow through one or more of the cell culture channels. In some embodiments, co-culture of aerobic and anaerobic microbes can reduce the local concentration of oxygen in a cell culture channel.

The cell culture systems described herein can be used to study the effect of non-intestinal cells, tissues, and/or factors on the cells comprised by a cell culture system as described herein. In some embodiments, a first cell culture system, comprising a cell culture system as described herein, is connected to or coupled to a second cell culture system of any design, comprising cells or tissues which are not intestinal epithelial cells. In some embodiments, the cells or tissues comprised by the second cell culture system are liver cells and/or tissue. In some embodiments, some fraction of an effluent of the second cell culture system and/or factors derived from cells which are not intestinal epithelial cells (e.g. signaling molecules, growth factors, or hormones) is introduced into the fluid flowing through the fluid channel of the cell culture system as described herein comprising intestinal epithelial cells. The response of the intestinal epithelial cells, endothelial cells, immune cells, and/or connective tissue cells, and/or microbial cells in the first cell culture system as described herein can then be determined. Responses of intestinal epithelial cells, endothelial cells, immune cells, and/or connective tissue cells, and/or microbial cells, and methods of determining and/or measuring them are described below herein.

In some embodiments, cells are introduced to the cell culture system described herein by adding cells to a fluid and causing the fluid to flow through the fluid channel and/or cell culture channel to which the cells are to be introduced. In some embodiments, in order to enhance attachment of the cells, the cells are caused to flow into the channel and the flow of the fluid is then temporarily halted to allow the cells to attach to the membrane, attachment molecules, and/or other cells already present in the channel. In some embodiments, in order to enhance attachment of the cells, the cell culture system can be temporarily rotated or reoriented so that the surface to which it is desired that the cells attach is the bottom surface of the channel. In some embodiments, alterations of the fluid flow or the orientation of the cell culture system last for 2 or more minutes, e.g. 2 minutes, 5 minutes, 15 minutes, 30 minutes, 60 minutes, 120 minutes or more. In some embodiments, alterations of the fluid flow or the orientation of the cell culture system last for approximately 1 hour. In some embodiments, alterations of the fluid flow or the orientation of the cell culture system last for approximately 90 minutes.

In some embodiments, described herein is a method of producing an intestinal organoid, the method comprising providing a fluid suitable for culturing and/or maintaining intestinal epithelial cells to the cell culture system described herein such that the fluid contacts the intestinal epithelial cells and culturing the intestinal cells in vitro. Examples of fluids suitable for culturing and/or maintaining intestinal epithelial cells are described above herein. In some embodiments, the method of producing an intestinal organoid further comprises culturing intestinal epithelial cells in a first cell culture channel and endothelial cells, immune cells, and/or connective tissue cells in a second cell culture channel. In some embodiments, the membrane separating the two cell culture channels is caused to stretch. In some embodiments, the fluid flow through the at cell culture channels is approximately 30 µL/hr. In some embodiments, the shear stress is approximately 0.02 dyne/cm$^2$. In some embodiments, the membrane is stretched approximately 10% along a plane at approximately 0.15 Hz. In some embodiments, the intestinal epithelial cells are Caco-2 cells. In some embodiments, the microbial cells are *Lactobacillus rhamnosus* GG (LGG) cells. In some embodiments, the intestinal epithelial cells are cultured at least until villi structures are present.

In some embodiments, the cell culture systems described herein can be used to study the differentiation of stem cells into mature intestinal cells by introducing stem cells, e.g. iPSCs, adult stem cells, or ESCs into the cell culture system as described herein. Differentiation factors and/or candidate differentiation factors can optionally be added to the cell culture system and their effect on the differentiation of the stem cells determined.

In some embodiments, the cell culture systems described herein comprise a system for evaluating intestinal treatments, function, and/or pathologies. In some embodiments, the cells in the cell culture system can be obtained from a subject suffering from an intestinal disorder, e.g. celiac, Crohn's disease, ulcerative colitis, or irritable bowel syndrome. In some embodiments, the conditions in the cell culture system can be modified to simulate an intestinal disorder. By way of non-limiting example, intestinal disorders can be simulated and/or modeled by introducing pathogenic microbial cells to the cell culture system; introducing high levels of microbial cells to the cell culture system; or increasing fluid flow rates to simulate diarrhea.

In some embodiments, the cell culture systems described herein comprise a system for evaluating intestinal effector agents. In some embodiments, described herein is a method of evaluating intestinal effector agents comprising contacting the intestinal epithelial cells of a cell culture system as described herein with at least one candidate intestinal effector agent and measuring the response of the cells in the cell culture system to determine the effect of the at least one candidate intestinal effector agent.

In some embodiments, an intestinal effector agent can be a compound, mixture, or organism. A candidate effector agent can be an agent known to modulate the behavior of intestinal epithelial cells and/or microbes that can be found in the intestine or it can be an agent that is to be tested to see if it can modulate the behavior of intestinal epithelial cells and/or microbes that can be found in the intestine. In some embodiments, an intestinal effector agent is a treatment or drug. In some embodiments, an intestinal effector agent is a pathogen and/or toxin. Non-limiting examples of intestinal effector agents are therapeutics, small molecules, nutriceuticals, antidiarrheals, probiotics, natural intestinal microflora and/or microbes, foods, vitamins, pathogens, and toxins. In some embodiments, the intestinal effector agent is an agent which can be administered to a subject or a patient orally.

In some embodiments, the cells of a cell culture system as described herein can be contacted with one or more intestinal effector agents, e.g. one effector agent, two effector agents, three effector agents, or more effector agents. In some embodiments, the intestinal epithelial cells of a cell culture system as described herein are contacted with one or more intestinal effector agents. In some embodiments, the microbial or pathogen cells of a cell culture system as described herein are contacted with one or more intestinal effector agents. In some embodiments, the endothelial, immune, or connective cells of a cell culture system as described herein are contacted with one or more intestinal effector agents. By way of non-limiting example, the intestinal epithelial cells of a cell culture system as described herein can be contacted with two or more intestinal effector agents to determine if two drugs interact, or if a drug modulates the natural gut microflora.

In some embodiments, the response of the cells in a cell culture system as described herein can be measured to determine the effect of at least one candidate intestinal effector agent. In some embodiments, the response of the intestinal epithelial cells is measured. In some embodiments, the response of the microbial cells is measured. In some embodiments, the response of the endothelial cells, immune cells, and/or connective tissue cells are measured. Measuring the response of the cells can include, but is not limited to, determining changes in morphology, viability, cell number, metabolic rate, transcription, translation, marker gene expression, levels of a reporter gene, transport, barrier function, morphology of tight junctions, and/or permeability of the cell layer. Measuring the response of the cells can include, but is not limited to, determining the rate at which an intestinal effector agent is taken up by cells, metabolized by cells, secreted by cells, or crosses one or more layers of cells. Measuring the response of the cells can include, but is not limited to, determining how cells metabolize an intestinal effector agent. The drug metabolizing functions of cells also can be assayed before or after villi formation by measuring CYP3A4 enzyme activities using a chemical or luminogenic substrate which is converted to a luminescent form by active CYP3A4 enzyme. Assays for CYP3A4 activity are well known in the art and substrates for detecting CYP3A4 activity are commercially available, e.g. Luciferin-IPA (Cat No V9001; Promega Madison, Wis.). Non-limiting examples of measuring the response of the cells can include determining cellular morphology using confocal microscopy; determining levels of proteins using immunofluorescence microscopy; and/or determining the integrity of the intestinal epithelial cell monolayer resulting from establishment of apical tight junctions by measuring trans-epithelial electrical resistance (TEER) using a voltage-ohm meter (87V Industrial Multimeter, Fluke Corporation, Everett, Wash.) coupled to Ag/AgCl electrode wires (0.008" in diameter; A-M systems, Inc., Sequim, Wash.).

The methods and cell culture systems described herein can be used to examine or test intestinal effector agents for the purposes of pharmacology, toxicology, drug development, drug delivery, protein or peptide delivery, drug metabolism, antibiotic effect, suitability and degradability of drug coatings, IgA transport, screening of genetically modified organisms for allergenicity and toxicity, drug-drug interaction drug bioavailability, drug clearance, multi-organ interactions, nanotoxicology, diagnostics, therapeutics, nutritional applications, physiology of intestinal barrier, gastrointestinal (GI) disease models and their mechanism, etiology of disease in the GI tract, wound healing, tissue regeneration, tissue engineering, intestinal homeostasis, intestinal stem cell researches, host-microbes interactions, microbial communities in the GI tract, microbial biofilm in the mucus layer, and probiotics therapies.

In some embodiments, the methods and cell culture systems herein can be used with cells comprising drug transporter polymorphisms for the purposes of drug development, drug delivery, drug metabolism, and drug clearance studies.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. These and other changes can be made to the disclosure in light of the detailed description.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

This invention is further illustrated by the following examples which should not be construed as limiting.

Some embodiments of the present invention can be defined as any of the following numbered paragraphs.

1. A cell culture system comprising
    a fluidic device having a fluid channel connected to a fluid source, the fluid source supplying fluid to the fluid channel;
    a membrane positioned within the channel between membrane support elements, at least portion of the membrane being flexible;
    a membrane strain mechanism coupled to the membrane support elements capable of moving the membrane support elements and causing the membrane to stretch along at least one dimension of the membrane; and
    at least one layer of intestinal epithelial cells attached to at least one surface of the membrane.
    wherein the shear stress on the fluid flowing through the fluid channel is less than 1.0 dyne/cm$^2$.
2. The system of paragraph 1, wherein the shear stress on the fluid flowing through the fluid channel is from 0.008 to 0.08 dyne/cm$^2$.
3. The system of any of paragraphs 1-2, wherein the shear stress on the fluid flowing through the fluid channel is approximately 0.018 dyne/cm$^2$.
4. The system of any of paragraphs 1-3, wherein the shear stress on the fluid flowing through the fluid channel can vary over time.
5. The system of paragraph 4, wherein the shear stress on the fluid flowing through the fluid channel can vary over time from 0 to 1000 dyne/cm$^2$.
6. The system of any of paragraphs 4-5, wherein the shear stress on the fluid flowing through the fluid channel can vary over time from 0.008 to 0.08 dyne/cm$^2$.
7. The system of any of paragraphs 1-6, wherein the membrane is caused to stretch from 0% to 50%.

8. The system of any of paragraphs 1-6, wherein the membrane is caused to stretch from 5% to 15%.
9. The system of any of paragraphs 1-8, wherein the membrane is caused to stretch approximately 10%.
10. The system of any of paragraphs 1-9, wherein the membrane is caused to stretch more than 15% to create an abnormal condition/state of the intestinal epithelial cells.
11. The system of any of paragraphs 1-10, wherein the membrane is caused to stretch in a cyclic manner at a rate in the range of 0.01 Hz to 2 Hz.
12. The system of any of paragraphs 1-11, wherein the membrane is caused to stretch in a cyclic manner at a rate in the range of 0.05 Hz to 0.25 Hz.
13. The system of any of paragraphs 1-12, wherein the membrane is caused to stretch in a cyclic manner at a rate of 0.15 Hz.
14. The system of any of paragraphs 1-12, wherein the membrane is caused to stretch in a cyclic manner at a rate greater than 0.2 Hz to create an abnormal condition/state of the intestinal epithelial cells.
15. The system of any of paragraphs 1-14, wherein the membrane is caused to stretch in an irregular or intermittent manner.
16. The system of any of paragraphs 1-15, wherein the fluid flows through the fluid channel at a flow rate less than 500 µL/hr.
17. The system of any of paragraphs 1-16, wherein the fluid flows through the fluid channel at a flow rate less than 100 µL/hr.
18. The system of any of paragraphs 1-17, wherein the fluid flows through the fluid channel at a flow rate from 0 to 50 µL/hr.
19. The system of any of paragraphs 1-18, wherein the fluid flows through the fluid channel at a flow rate of approximately 30 µL/hr.
20. The system of any of paragraphs 1-19, further comprising at least one type of attachment molecule that supports adhesion of a plurality of living cells coating at least one side of the membrane.
21. The system of paragraph 20, wherein the at least one attachment molecule is selected from the group consisting of:
collagen; collagen type I; MATRIGEL™; extracellular matrix; laminin; proteoglycan;
vitronectin; fibronectin; poly-D-lysine; polypeptides; oligonucleotides; DNA; and polysaccharide.
22. The system of any of paragraphs 1-21, wherein the intestinal epithelial cells are mammalian or human cells.
23. The system of any of paragraphs 1-22, wherein the intestinal epithelial cells are selected from the group consisting of:
Caco2 cells; HT-29 cells; primary small intestine epithelial cells; primary large intestine epithelial cells; iPS cells; ESC cells; stem cells; paneth cells; crypt cells; and mucus-secreting cells.
24. The system of any of paragraphs 1-23, wherein the intestinal epithelial cells of the system further comprise villi structures.
25. The system of any of paragraphs 1-24, wherein the system further comprises at least one layer of endothelial cells on at least the second surface of the membrane.
26. The system of any of paragraphs 1-25, wherein the membrane is positioned such that it divides the fluid channel into a first cell culture channel and a second cell culture channel.
27. The system of paragraph 26, wherein the first cell culture channel comprises intestinal epithelial cells.
28. The system of any of Paragraphs 26-27, wherein the second cell culture channel comprises cells selected from the group consisting of:
endothelial cells, immune cells, and connective tissue cells.
29. The system of any of paragraphs 1-27, wherein the system further comprises microbial cells or pathogens.
30. The system of paragraph 29, wherein the microbial cells are maintained in the system for at least 1 day.
31. The system of any of paragraphs 29-30, wherein the microbial cells are selected from the group consisting of:
*Lactobacillus; Bacterioides; Ruminococcus; Peptococcus; Peptostreptococcus; Bifidobacterium; Escherichia; Achromobacter; Acidaminococcus fermentans; Acinetobacter cacoaceticus; Aeromonas; Alcaligenes faecalis; Bacillus; Butyriviberio fibrosolvens; Camplyobacter; Campylobacter coli; Clostridium difficile; Clostridium sordelli; Enterobacter cloacae, Enterococcus faecalis; Enterococcus faecium; Escherichia coli; Flavobacterium; Mycobacterium; Mycoplasma; Plesiomonas shigelloides; Propionibacterium acnes; Pseudomonas aeruginosa; Ruminococcus bromii; Sarcina; Staphylococcus aureus; Streptococcus anginosus; Veillonella; Vibrio; Yersinia enterocolitica; Lactobacillus rhamnosus; Lactobacillus rhamnosus GG; Bifidobacterium breve; Bifidobacterium longum; Bifidobacterium infantis; Lactobacillus acidophilus; Lactobacillus plantarum; Lactobacillus paracasei; Lactobacillus bulgaricus*; and *Streptococcus thermophilus*.
32. The system of any of paragraphs 29-30, wherein the microbial cells are pathogenic.
33. The system of paragraphs 29 or 32, wherein the pathogens are selected from the group consisting of: enterotoxigenic *Escherichia coli; Bilophila wadsworthia; Shigella; Yersinia; Pleisiomonas; Vibrio; Aeromonas; Campylobacter; Crytosporidia; Coccidosis; Salmonella; Helicobacter pylori; Clostridium difficile; Salmonella kedougou; Bacteroides; Clostridium; Firmicutes; Shigella dysenteriae; Salmonella enterica; Salmonella typhi; Listeria; Listeria monocytogenes; Vibrio parahaemolyticus; Proteus; Vibrio cholerae; Enterococcus faecalis; Yersinia enterocolitica*; and *Campylobacter jejuni*; rotavirus; norwalk-like viruses; adenoviruses; astroviruses; sapporo-like viruses; toroviruses; coronaviruses; picornaviruses; herpes viruses; noroviruses; *Candida; Aspergillus; Candida albicans*; single-celled parasites; multi-celled parasites; ameobas; worms; tape worms; protozoans; flukes; roundworms; pinworms; hookworms; *Giradia lamblia; cryptosporidium*; and *Entamoeba histolytica*.
34. The system of any of paragraphs 29-33, wherein the microbial cells are aerobic.
35. The system of any of paragraphs 29-33, wherein the microbial cells are anaerobic.
36. The system of any of paragraphs 29-35, wherein the system comprises both aerobic and anaerobic microbial cells.
37. The system of any of paragraphs 29-36, wherein the microbial cells are present in the first cell culture channel.
38. The system of any of paragraphs 29-37, wherein the system further comprises an anaerobic gas chamber in contact with at least part of the first cell culture channel.
39. The system of paragraph 38, wherein an oxygen gradient is established in the fluid flowing through the first cell culture channel.
40. The system of any of paragraphs 1-39, wherein the membrane is at least partially porous.

41. The system of paragraph 40, wherein at least one pore aperture in the membrane is between 0.5 μm and 10 μm along a width dimension.
42. The system of any of paragraphs 1-41, wherein the membrane comprises PDMS.
43. The system of any of paragraphs 1-42, wherein the membrane is caused to stretch due to vacuum pressure.
44. The system of paragraph 43, wherein the system further comprises:
   a first chamber wall of the device positioned adjacent to the at least one fluid channel, wherein the membrane is mounted to the first chamber wall;
   a first operating channel adjacent to the at least one fluid channel on an opposing side of the first chamber wall, wherein a pressure differential applied between the first operating channel and the at least one fluid channel causes the first chamber wall to flex in a first desired direction to expand or contract along the plane defined by the membrane; and
   a vacuum system providing a pressure differential between the at least one fluid channel the at least one operating channels, wherein the membrane stretches along the plane in response to the pressure differential.
45. The system of paragraph 44, further comprising;
   a second chamber wall of the device positioned adjacent to the at least one fluid channel, wherein an opposing end of the membrane is mounted to the second chamber wall; and
   a second operating channel positioned adjacent to the at least one fluid channel on an opposing side of the second chamber wall, wherein the pressure differential between to the second operating channel and the at least one fluid channel causes the second chamber wall to flex in a second desired direction to expand or contract along the plane defined by the membrane.
46. The system of any of paragraphs 1-45, wherein the fluidics device comprises a microfluidic chip.
47. The system of any of paragraphs 1-46, wherein the system is connected or coupled to a second cell culture system comprising cells or tissue which are not intestinal in origin.
48. The system of paragraph 47, wherein the second cell culture system comprises liver cells or tissue.
49. A method of producing an intestinal organoid comprising;
   providing a fluid suitable for maintaining intestinal epithelial cells to the cell culture system of any of paragraphs 1-48 such that the fluid contacts the intestinal epithelial cells; and culturing the intestinal epithelial cells in vitro.
50. The method of paragraph 49, further comprising culturing the cells at least until villi structures are evident.
51. A system for evaluating intestinal effector agents comprising the cell culture system of any of paragraphs 1-48.

EXAMPLES

Example 1

The 'gut-on-a-chip' can be a microfluidic system containing monolayers of cultured human intestinal epithelial cells and human endothelial cells from capillary blood vessels and/or lymphatic lacteal separated by a porous flexible extracellular matrix (ECM) coated membrane that can experience rhythmic mechanical distortion similar to intestinal motility (e.g. peristalsis and segmental), which is designed to recapitulate the tissue-tissue interfaces and microstructure of the human intestine (FIG. 1). The goal of 'gut-on-a-chip' project is to provide a robust, reproducible, and predictive in vitro platform for human responses to orally delivered compounds, therapeutics, nutriceuticals, functional foods, pathogens, and toxins. The gut-on-a-chip should be useful for a wide range of applications in fields of pharmacology, toxicology, drug development, drug delivery, drug metabolism, drug-drug interactions, drug bioavailability, drug clearance, multi-organ interactions (e.g. intestine vs. liver), diagnostics, therapeutics, nutritional application, physiology of intestinal barrier, gastrointestinal (GI) disease models and their mechanism, etiology of disease in the GI tract, wound healing, tissue regeneration, tissue engineering, intestinal homeostasis, intestinal stem cell researches, host-microbes interactions, microbial communities in the GI tract, microbial biofilm in the mucus layer, probiotics therapies, and potentially covering all other GI tract-related researches.

Figure 2:
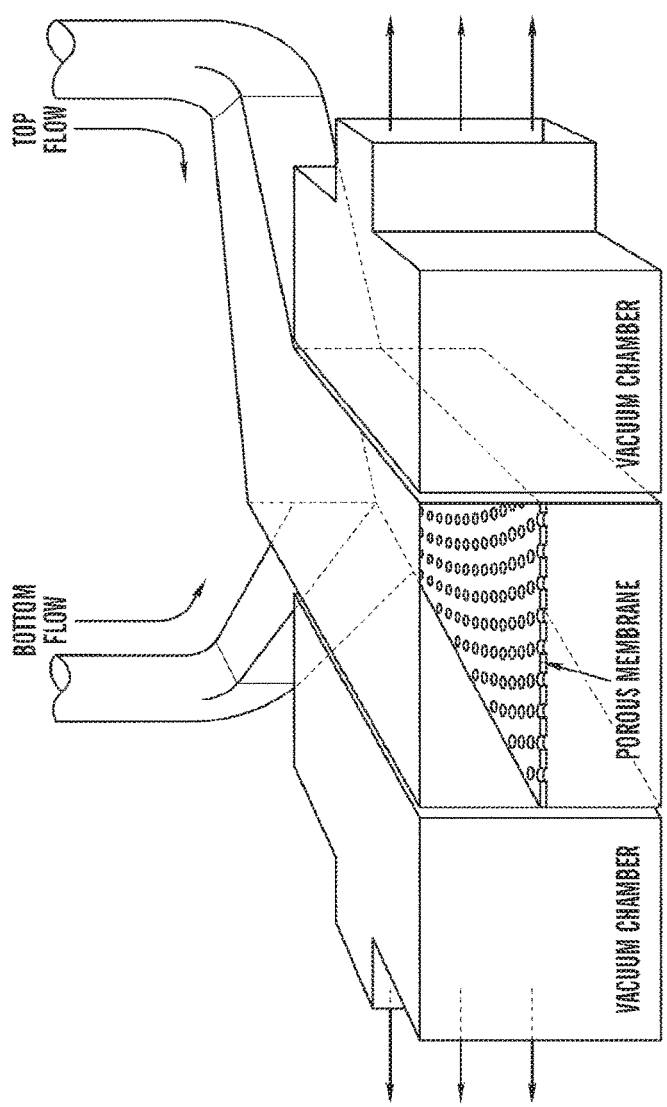
FIG. 2 depicts a schematic of the structure of one embodiment of gut-on-a-chip highlighting a double-layered cell culture microchannel in the top (violet) and the bottom (pink) separated by the porous PDMS membrane and two vacuum chambers (sky blue) beside the double-layered cell culture channel.
Figure 3A:
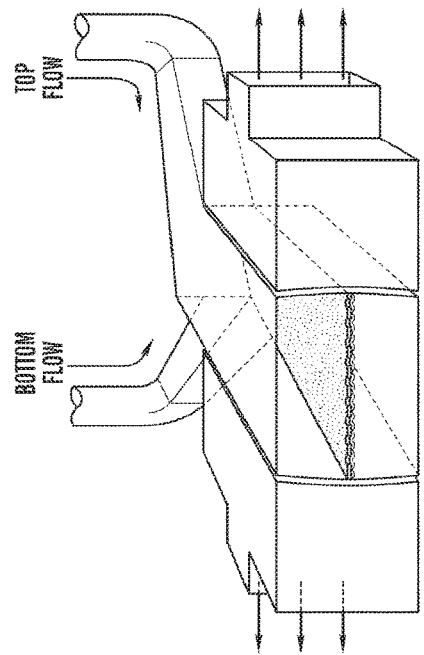
FIGS. 3A-3D depict a series of schematics demonstrating the mechanical stretching in one embodiment of gut-on-a-chip by repeating from FIG. 3A to FIG. 3D over time. The cyclic stretching was applied in gut-on-a-chip to impose defined mechanical strain on a cell monolayer by the vacuum-driven negative pressure on vacuum channels.
Figure 3B:
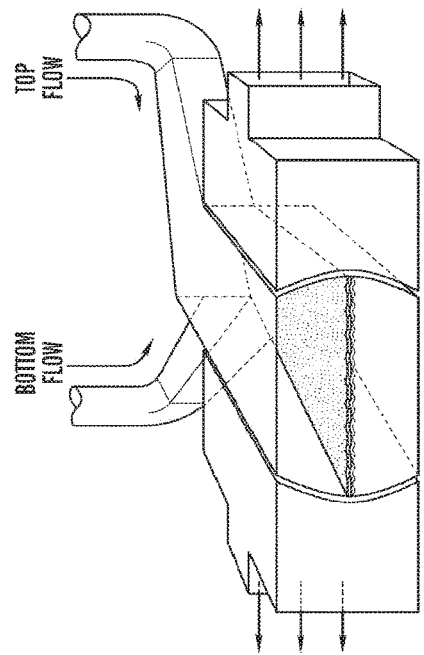
Figure 3C:
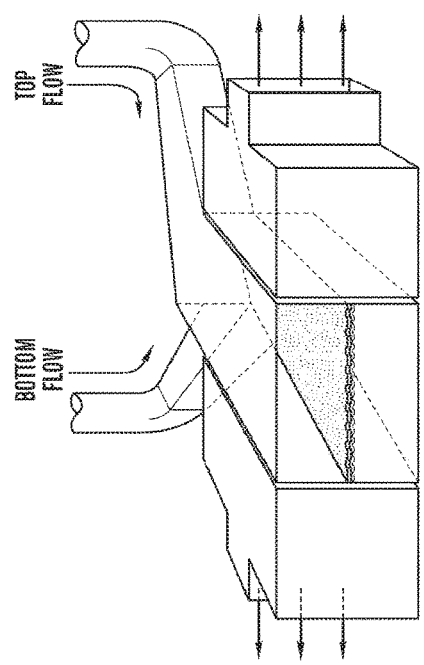
Figure 3D:
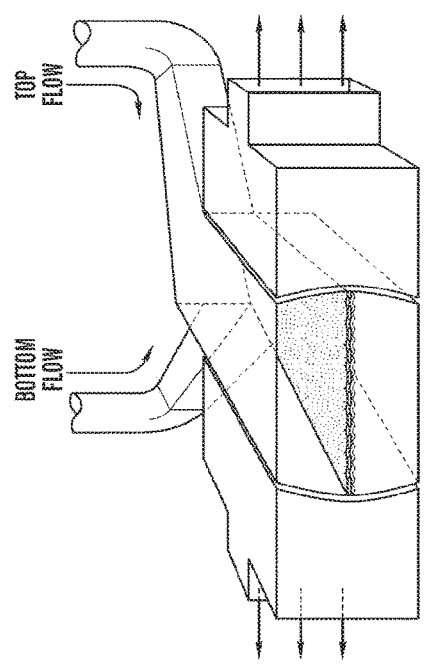

Described herein is the fabrication of a gut-on-a-chip prototype microfluidic device using a silicone elastomeric polymer (polydimethylsiloxane; PDMS) with a 3D structure containing a double layer of closely apposed parallel microchannels (1,000×10,000×150 μm=W×L×H). One microchannel represents the intestinal lumen and the other microchannel mimics the capillary microvasculature. These microchannels are separated by a flexible, porous PDMS membrane that is 30 μm in thickness possessing holes that are 10 μm in diameter (FIG. 2). Beside the microchannel, two vacuum chambers are placed to apply vacuum-driven mechanical strain on the microchannel (FIGS. 3A-3D). The gut-on-a-chip was optimized in geometry to minimize shear stresses on gut epithelial cells and problems discovered with peeling-off of the epithelial monolayer due to differences the strength of cell-substrate adhesion. The construction process, as compared to previously used processes, also was successfully improved by developing an etching-free process to make hollow vacuum chambers because the PDMS etching process is problematic in terms of the inconsistent etching efficiency from device to device, usage of toxic chemicals, and time/labor issues.

The experiments described herein were conducted with human colon adenocarcinoma Caco-2 cells, which are commonly used to model the human absorptive intestinal epithelium in existing commercial drug-testing products. Although Caco-2 cells have been reported to lack some molecular transporters and drug metabolizing enzymes [2] and to not secrete a mucus layer [3], it is a well characterized cell line that can reestablish high barrier function, tight junction protein expression, selective permeability, and activity of brush border enzymes that correlate well with human small intestinal functions [4]. Human microvascular endothelial cells (HMVEC) were used to form the capillary endothelium on the opposite site of the porous ECM-coated membrane from the co-cultured Caco-2 cells, as demonstrated in FIG. 1.

Figure 4B:
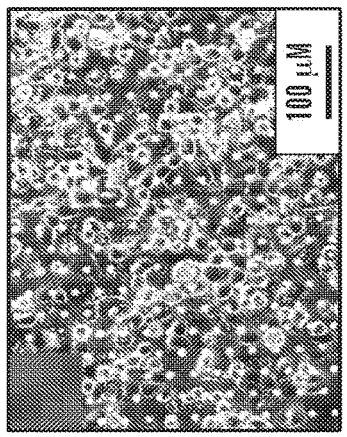
FIGS. 4A-4D depict magnified images of the establishment of a Caco-2 monolayer in a microchannel After Caco-2 cells are inoculated into a microchannel (FIG. 4A), cells were allowed to be attached on the surface of a porous membrane in a microchannel for 1.5 hours (FIG. 4B), then culture medium was perfused at a constant flow rate of 30 μL/hr for 48 hours. A confluent monolayer is made after approximately 48 hours (FIG. 4C) in a microchannel A zoom-in image of a Caco-2 monolayer on the porous membrane is depicted in FIG. 4D. Repetitive pores have 10 μm in diameter with 30 μm spacing.
Figure 4D:
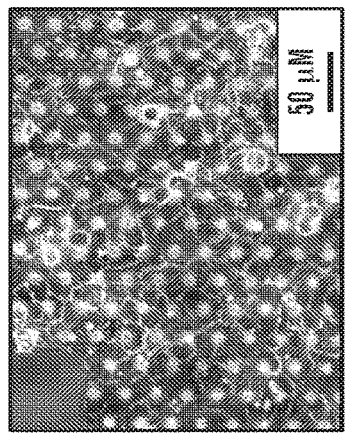
Figure 4A:
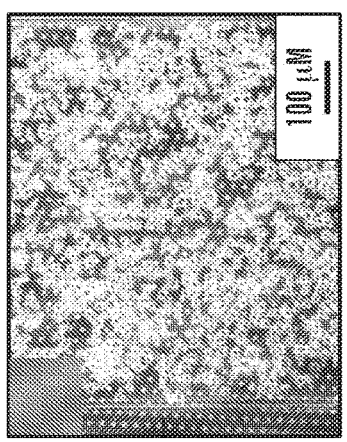

To develop this model for in vitro analysis of human intestinal function, porous PDMS membranes were fabricated inside a microfluidic device, then coated with ECM by infusing a mixture of collagen I and Matrigel dissolved in DMEM (containing 4.5 g/L glucose, antibiotics, but no serum) into the microchannels, and incubating the device in a humidified incubator with 5% $CO_2$ at 37° C. for overnight. The next day DMEM (containing 4.5 g/L glucose, antibiotics with 20% serum, FBS) was perfused through the channels (30 μL/h), and then Caco-2 cells (~5×10$^6$ cells/mL) were flowed into one channel in medium over a 6 h period (FIG. 4A). After Caco-2 cells were introduced into the top microchannel, all the tubing connected to the device was clamped, and the cells were incubated in a humidified incubator with 5% $CO_2$ at 37° C. for 1.5 hour to promote cell attachment (FIG. 4B).

Figure 4C:
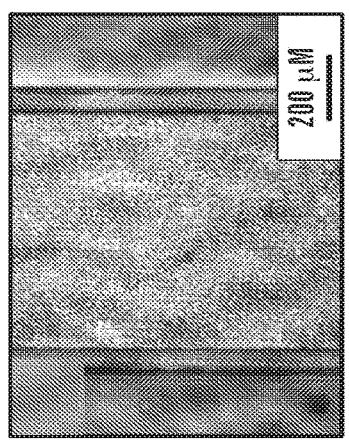

After the Caco-2 cells attached to the surface of a porous PDMS membrane, culture medium (DMEM containing 4.5 g/L glucose, antibiotics, and 20% FBS) was perfused into the top microchannel at 30 µL/h for 48 hours to establish the confluent and differentiated Caco-2 monolayer (FIGS. 4C and 4D), while the bottom microchannel was clamped (i.e. no perfusion flow). Once the Caco-2 monolayer was well established (FIGS. 4C and 4D), both top and bottom microchannels were simultaneously perfused with culture medium (DMEM containing 4.5 g/L glucose, antibiotics, and 20% FBS) at 30 µL/h. Before inoculating the HMVE cells on the other side of the porous PDMS membrane, DMEM (containing 4.5 g/L glucose, antibiotics, and 5% serum):EGM2-MV, 1:4, v/v) was perfused through the $2^{nd}$ channel for 24 hours. HM VE cells (~$5 \times 10^6$ cells/mL) were then seeded into the bottom microchannel, and the device was flipped upside down to promote attachment of the HMVE cells on the opposite side of a Caco-2 monolayer for 1.5 hours. After HMVECs were well attached, medium was perfused at 30 µL/h through both the top and bottom microchannels to maintain the co-culture of Caco-2 and HM VE cells (FIG. 5). Culture medium was perfused through tubing controlled by a syringe pump that had a range of constant flow rate at 20-40 µL/h; this corresponds to a range of shear stress from 0.012-0.024 dyne/$cm^2$. Shear stresses observed in vivo in the small intestine have been reported to be in the range of 0.008-0.08 dyne/$cm^2$, which is in good agreement with the range of shear stress in this embodiment of the gut-on-a-chip device [5-6].

After the cell monolayers were fully confluent and stabilized under defined fluidic conditions, transport experiments were conducted. Mechanical strains were applied with cyclic stretching driven by applying negative pressure to vacuum chambers at constant frequency of 0.15 Hz with various elongation percentages up to ~26% (~85 kPa) (FIGS. 3A-3D). The co-cultured monolayers of Caco-2 and HMVE cells experienced with cyclic deformations for 12 hours or more prior to initiating the transport or barrier functional analysis experiments. Cyclic mechanical strain applied to this gut-on-a-chip device was found to mimic physiological peristalsis of the intestine enhanced intestinal epithelial barrier function significantly, as measured by large increases in transepithelial electrical resistance (TEER) (data not shown). Electrical resistances between the top and the bottom microchannels were monitored using an Ag/AgCl electrode equipped with an Ohm meter, and the resistance was converted into TEER value by multiplying values by the surface area of the cell monolayer. When mechanical strain was applied to the cell monolayers from 0% to 25% elongation using increments of 5% increases in strain over time over 24 hours, TEER values were observed to immediately increase, then reach higher plateau values, with a progressive increase over time as % elongation of the tissue-tissue interface increased.

Figure 6A:
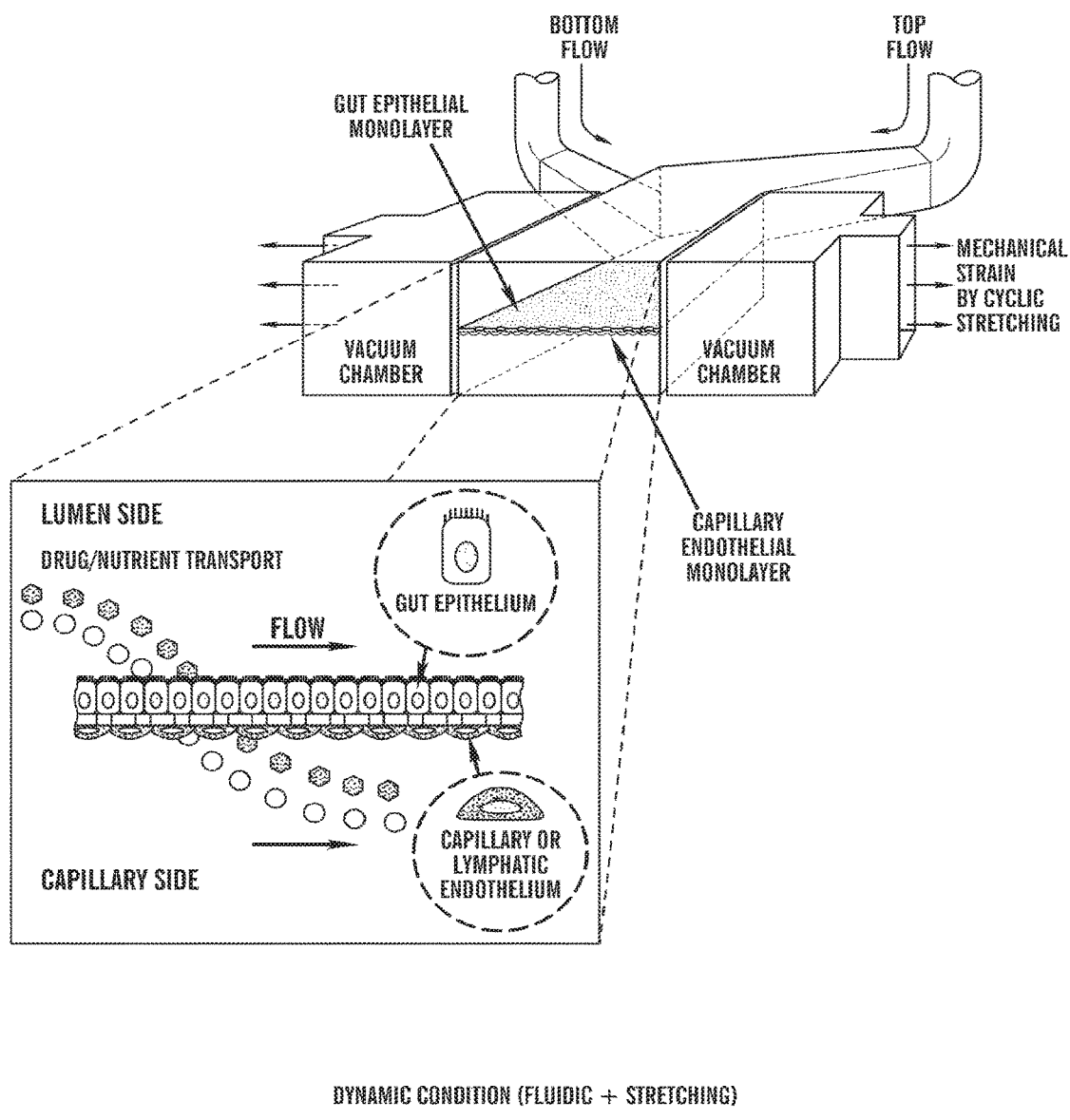
FIGS. 6A-6C depict schematics for the transport experiment in gut-on-a-chip.
Figure 6B:
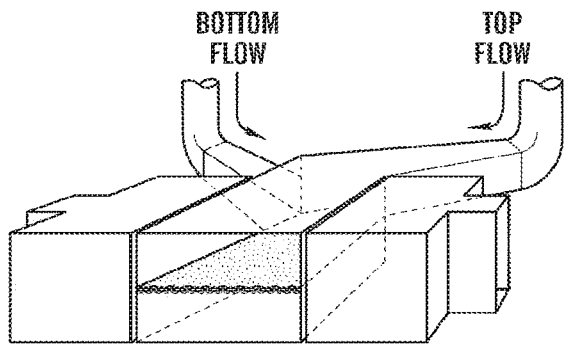
Figure 6C:
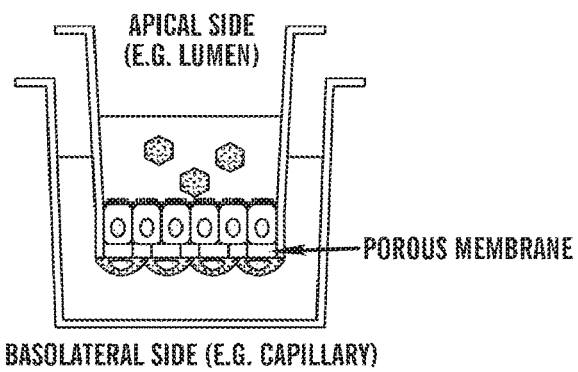

To measure the molecular permeability through the cell monolayer, a target molecule dissolved in a culture medium was introduced in the top microchannel (i.e. lumen side), while fresh culture medium was simultaneously flowed in the bottom channel (i.e. capillary side). Samples were intermittently taken from the bottom channel and analyzed to estimate cumulative molecular transported through the cell monolayer (FIGS. 6A-6C). These studies revealed that mechanical strain increased paracellular transport of fluorescent molecules, including FITC-dextran (FIGS. 7 and 9) and lucifer yellow (FIG. 8) whether the Caco-2 cell monolayer was tested alone or in combination with the HMVE cell monolayer. Apparent permeability obtained in this tissue-tissue barrier functional model$_{(Papp)}$ was calculated based on the equation as Papp=(dQ/dt)/(A·$C_o$), where Q is the cumulative amount transported of compound on the receiver side (vg), t is the time (sec), A is the exposed surface area of the cell monolayer across which transport is occurring ($cm^2$), and $C_o$ is the initial concentration of the compound on the donor side (14/mL) [7]. At this moment, it is not clearly understood why mechanical stretching enhances the paracellular transport of both a large molecule (FD20) and a small molecule (LY), given that TEER is increasing indicating a higher junctional barrier is present. However, this might result from a physiologically relevant transcytosis response as observed in quantum dot transport studies previously observed in the lung-on-a-chip [1].

Figure 10:
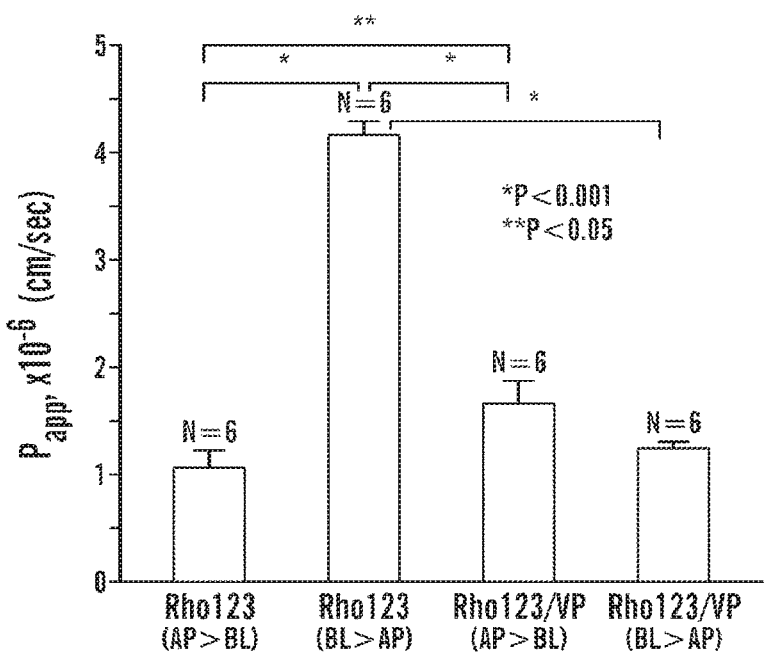
FIG. 10 depicts a graph of the apparent permeability coefficient$_{(Papp)}$ of Rhodamine 123 (Rho123), a substrate of permeability glycoproteins (P-gp) in Caco-2 cells, was obtained in the Transwell containing a 21-day-cultured Caco-2 monolayer on the surface of a porous membrane (0.4 μm in pore size). To inhibit efflux transport in Caco-2 cells, verapamil, an inhibitor of P-gp, was applied in some experimental setups. An experimental scheme for this static transport analysis was described in FIG. 6C. For the transport experiment of Rho123 from apical side (AP) to the basolateral side (BL) (N=6), Rho123 dissolved in a culture medium (100 μM, final concentration, 200 μL) was substituted in the AP side of a Transwell, whereas a fresh culture medium (700 μL) was added in the BL side of a Transwell. For the efflux experiment of Rho123 from BL side to AP side (N=6), Rho123 dissolved in a culture medium (100 μM, final concentration, 700 μL) was substituted in the BL side of a Transwell, and a fresh culture medium (200 μL) was replaced in the AP side of a Transwell. To test the effect of P-gp inhibition, verapamil dissolved in a culture medium (300 μM, final concentration) was applied in both AP and BL side of a Transwell, then transport experiments in either way from AP to BL (N=6) or from BL to AP (N=6) were performed. Error bars indicate standard errors.
Figure 11:
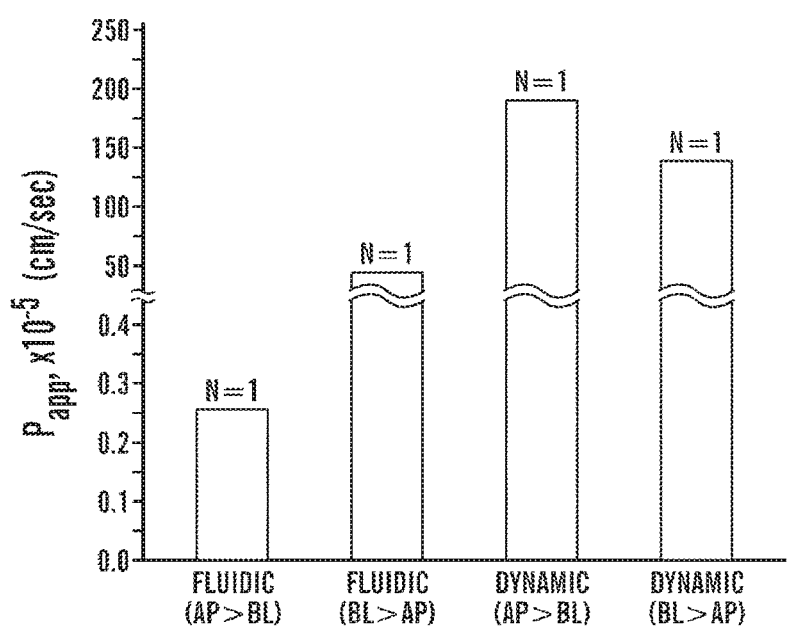
FIG. 11 depicts a graph of the apparent permeability coefficient$_{(Papp)}$ of Rho123, a substrate of P-gp in Caco-2 cells, in a microfluidic gut-on-a-chip device. Experimental schemes for the fluidic and dynamic conditions were demonstrated in FIGS. 6A and 6B. For the transport experiment of Rho123 from AP side to BL side in either fluidic (N=1) or dynamic (N=1, 15% elongation) condition, Rho123 dissolved in culture medium (100 μM, final concentration) was flowed at 30 μL/h in the top microchannel, whereas fresh culture medium was perfused at 30 µL/h in the bottom microchannel. For the transport experiment of Rho123 from BL side to AP side in either fluidic (N=1) or dynamic (N=1, 15% elongation), Rho123 dissolved in culture medium (100 µM, final concentration) was flowed at 30 µL/h in the bottom microchannel, whereas fresh culture medium was perfused at 30 µL/h in the top microchannel. In both dynamic and fluidic conditions, samples were gathered in the outlet of both top and bottom microchannels approximately for 1 hour, then an aliquot (10 µL) was diluted to measure fluorescence, which was in a linear regime of fluorescence intensity versus Rho123 concentration. For the dynamic conditioning, mechanical strain with 15% elongation was applied prior to experiments.

To measure the transporter-mediated permeability, Rhodamine 123 (Rho123) was used as a substrate for the well-known permeability glycoprotein (P-gp) efflux transport pathway that Caco-2 cells are known to express. Under static conditions using a commercial Transwell filter set-up, Rho123 transport was observed as shown by efflux of Rho123 via P-gp, which corresponds to the higher $P_{app}$ value in 'BL>AP' transport than that in 'AP>BL' transport (FIG. 10). Also, when the P-gp inhibitor Verapamil was added to both channels, efflux from BL side to AP side was dramatically decreased (FIG. 10). After it was confirmed that Rho123 works well in the Caco-2 monolayer by targeting P-gp, Rho123 was applied in the gut-on-a-chip device. In this preliminary experiment, Rho123 dissolved in culture medium was applied in either AP side or BL side in the presence or the absence of the mechanical strain. In the presence of mechanical strain, $P_{app}$ values resulted in enhanced permeability, which was higher than the $P_{app}$ values of Rho123 efflux.

Based on these results, this gut-on-a-chip microfluidic device has potential applications as a novel in vitro intestinal model for testing nutrient absorption, ion transport, and nanoparticle/nanoparticle conjugate transport in the presence or the absence of the mechanical strain for evaluating the physiological relevance. The gut-on-a-chip also can be used to study drug development including its drug transport (uptake and efflux), pharm acokinetics, pharmacodynamics, metabolism, drug-drug interactions, effects of formulation of absorption as well as efficacy, toxicity, and clearance in the presence or the absence of mechanical strain for maximizing in vivo relevance. It can be applied to investigate interactions between gut epithelium and other cell types (e.g. capillary or lymphatic endothelium, immune cells, connective tissues, etc.) on a topological similarity with the structure of intestinal villus (FIG. 1).

The 'Gut on a chip' also can be applied to evaluate toxicology of conventional drugs and nano-sized materials (i.e. nanotoxicology) in the presence or the absence of mechanical strain. In addition, whether it can be used to model diseases of the GI tract such as inflammatory bowel disease (e.g. Crohn's disease and ulcerative colitis), ileus, and irritable bowel syndrome by recapitulating critical components and etiological factors, including relevant microbes. The systems described herein also allow exploration of the initiation, propagation, termination, central mechanisms, vaccination, and developing potential drugs for the intestinal diseases, and demonstrate host-microbes interactions, co-culture of the host cells with microbes, interplay between pathogens and probiotic strains, biofilm formations in the GI tract, and positive/negative effects of probiotic strains on the gut epithelium and other cell types. Furthermore, the engineered human microbiome on 'Gut on a chip' platform can be exploited to display how genetically engineered microbiomes can play a role in the microbial communities and host tissues to potentially improve the gut health. The Gut on a chip also can be used for the study of intestinal stem cells. The niche of intestinal stem cells and their fate can be modulated with various spatial structures in the microengineered device.

Further, the systems described herein can be used with non-planar porous membranes that more closely mimic the villus microarchitecture of the human intestine which has the potential to provide even more realistic models of gut function. This could be particularly relevant for studies analyzing microbial flora-epithelial interactions and food absorption.

Figure 7:
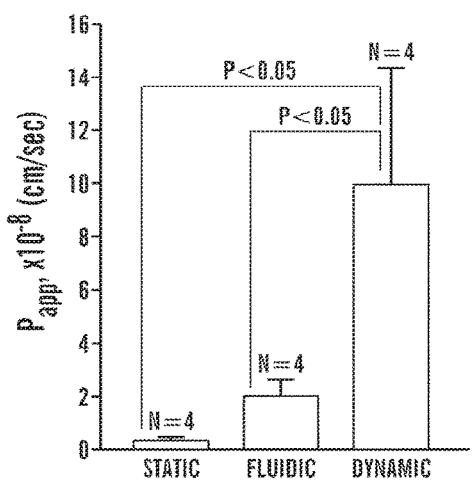
FIG. 7 depicts a graph of the apparent permeability coefficient$_{(Papp)}$ of a paracellular marker, FITC-dextran (FD20, 20 kDa), in a gut-on-a-chip device containing a Caco-2 monolayer on the surface of a porous membrane in the top microchannel Experimental schemes for static, fluidic and dynamic conditions were explained in FIGS. 6A-6C. In a dynamic condition (N=4), cyclic stretching was applied with 20% elongation under constant perfusion flow of 30 μL/h for 12 hours prior to FD20 transport experiments. In a fluidic condition (N=4), constant perfusion flow of 30 μL/h was conducted without any stretching motions (i.e. shear stresses only). In both dynamic and fluidic conditions, samples were gathered approximately for 1 hour from the outlet of a bottom microchannel, then an aliquot (10 μL) was diluted to measure fluorescence, which was in a linear regime of fluorescence intensity versus FD20 concentration. In a static condition (N=4), transport experiment was performed in a Transwell system. Error bars indicate standard errors.
Figure 8:
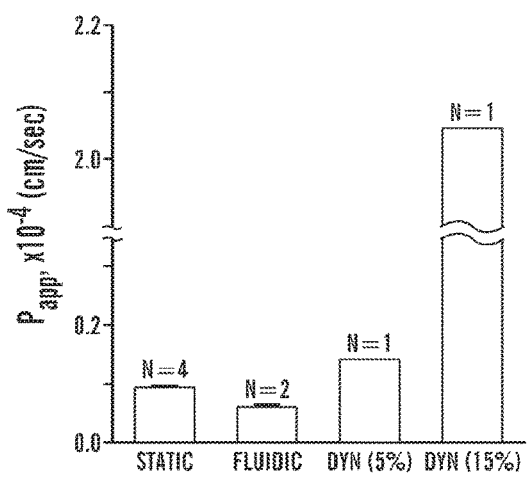
FIG. 8 depicts a graph of the apparent permeability coefficient (Papp) of a paracellular marker, Lucifer yellow (LY), in a gut-on-a-chip device containing a Caco-2 monolayer on the surface of a porous membrane in the top microchannel Experimental schemes for static, fluidic, and dynamic conditions were described in FIGS. 6A-6C. In a dynamic condition, cyclic stretching was applied with either 5% (N=1) or 15% (N=1) elongation in a constant perfusion at 30 μL/h for 12 hours prior to LY transport experiments. In a fluidic condition (N=2), constant perfusion flow at 30 μL/h was conducted without any stretching motions (i.e. shear stresses only). In both dynamic and fluidic conditions, samples were gathered approximately for 1 hour from the outlet of a bottom microchannel, then an aliquot (10 μL) was diluted to measure fluorescence, which was in a linear regime of fluorescence intensity versus LY concentration. In a static condition (N=4), transport experiments were performed in the Transwell system. Error bars indicate standard errors. The y-axis has a scale break to resume whole range of bar charts in the graph.
Figure 9:
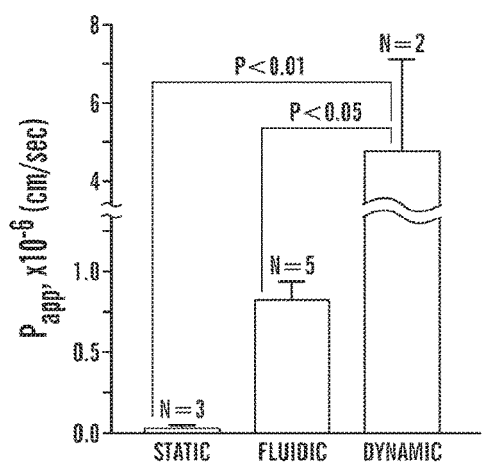
FIG. 9 depicts a graph of the apparent permeability coefficient$_{(PAPP)}$ of FD20 in a gut-on-a-chip device containing a Caco-2 monolayer on the surface of a porous membrane in the top microchannel and HMVEC monolayer on the opposite surface of a porous membrane in the bottom microchannel Experimental schemes for static, fluidic, and dynamic conditions were demonstrated in FIGS. 6A-6C. In a dynamic condition (N=2), cyclic stretching was applied with 15% elongation under the constant perfusion flow of 30 μL/h for 12 hours prior to FD20 transport experiments. In a fluidic condition (N=5), constant perfusion flow of 30 μL/h was conducted without any stretching motions (i.e. shear stresses only). In both dynamic and fluidic conditions, samples were gathered approximately for 1 hour from the outlet of a bottom microchannel, then an aliquot (10 μL) was diluted to measure fluorescence, which was in a linear regime of fluorescence intensity versus FD20 concentration. In a static condition (N=3), transport experiment was performed in a Transwell system. Error bars indicate standard errors. The Y-axis has a scale break to resume whole range of bar charts in the graph.

The mechanical strain applied on the gut-on-a-chip demonstrates the physiological relevance of the in vivo physical microenvironment in which peristalsis and segmental movement occurs in the living human intestine. For instance, the results described herein reveal that cyclic deformations (e.g. 0.15 Hz in frequency with 0-25% elongation) of the gut epithelial monolayer, induces a significant increase in junctional barrier function while increasing apparent permeability of specific molecules relative to either static Transwell cultures or use of a conventional microfluidic system without mechanical stretching (FIGS. 7, 8, and 9). This transport result with physiological mechanical strain can be a gold standard for evaluating drug candidates in vitro.

Effects produced by the mechanical strain provide a couple of critical advantages. First, gut-on-a-chip exhibits physiological responses that more closely mimic whole intestinal organ physiology in the human body by integrating cells originated from human (e.g. human intestinal cell lines, human primary intestinal cells, or human intestinal stem cells). This physiological relevance will be valuable in developing reliable drug screening process in mid-stage of drug development and reproducible pharm acokinetics as well. Second, gut-on-a-chip can provide an organ-level functionality to display how proximity of different cell types can contribute to make synergies in the absorption and transport of nutrients and drug compounds. Third, gut-on-a-chip may be able to dramatically reduce the informational gap between in vitro models, in situ animal models, and in vivo human body that has not yet been fully understood. By applying human intestinal microbes or potential pathogenic microbes, gut-on-a-chip can be used to reconstitute the situations in the human intestine with critical host cells. Since results in animal models often do not predict drug transport and metabolism responses observed in humans due to marked species differences, gut-on-a-chip can provide an alternative in vitro model with strong in vivo relevance by integrating multiple human organ-specific cell types in 3D structure under the mechanical strain mimicking physiological or pathological bowel peristaltic motions.

REFERENCES

1. Huh, D., et al., Reconstituting organ-level lung functions on a chip. Science, 2010. 328(5986): p. 1662-8.
2. Artursson, P. and R. T. Borchardt, Intestinal drug absorption and metabolism in cell cultures: Caco-2 and beyond. Pharm Res, 1997. 14(12): p. 1655-8.
3. Pontier, C., et al., HT29-M TX and Caco-2/TC7 monolayers as predictive models for human intestinal absorption: role of the mucus layer. J Pharm Sci, 2001. 90(10): p. 1608-19.
4. Le Ferrec, E., et al., In vitro models of the intestinal barrier. The report and recommendations of ECVAM Workshop 46. European Centre for the Validation of Alternative methods. Altern Lab Anim, 2001. 29(6): p. 649-68.
5. Lentle, R. G. and P. W. M. Janssen, Physical characteristics of digesta and their influence on flow and mixing in the mammalian intestine: a review. Journal of Comparative Physiology B-Biochem ical Systemic and Environmental Physiology, 2008. 178(6): p. 673-690.
6. Olesen, S. P., D. E. Clapham, and P. F. Davies, HEMODYNAM IC SHEAR-STRESS ACTIVATES A K+ CURRENT IN VASCULAR ENDOTHELIAL-CELLS. Nature, 1988. 331(6152): p. 168-170.
7. Artursson, P., K. Palm, and K. Luthm an, Caco-2 monolayers in experimental and theoretical predictions of drug transport. Advanced Drug Delivery Reviews, 2001. 46(1-3): p. 27-43.
8. Sung, J. H., et al., Microscale 3-D hydrogel scaffold for biomimetic gastrointestinal (GI) tract model. Lab Chip, 2011. 11(3): p. 389-92.

Example 2

Development of an in vitro living cell-based model of the intestine that mimics the mechanical, structural, absorptive, transport and pathophysiological properties of the human gut along with its crucial microbial symbionts could accelerate pharmaceutical development, and potentially replace animal testing. Described herein is one embodiment of a biomimetic 'Human Gut-on-a-Chip' microdevice composed of two microfluidic channels separated by a porous flexible membrane coated with extracellular matrix (ECM) and lined by human intestinal epithelial (Caco-2) cells that mimics the complex structure and physiology of living intestine. The gut microenvironment is recreated by flowing fluid at a low rate (30 µL/hr) producing low shear stress (0.02 dyne/cm$^2$) over the microchannels, and by exerting cyclic strain (10%; 0.15 Hz) that mimics physiological peristaltic motions. Under these conditions, a columnar epithelium develops that polarizes rapidly, spontaneously grows into folds that recapitulate the structure of intestinal villi, and forms a high integrity barrier to small molecules that better mimics whole intestine than cells in cultured in static Transwell models. In addition, a normal intestinal microbe (*Lactobacillus rhamnosus* GG) can be successfully co-cultured for extended periods (>1 week) on the luminal surface of the cultured epithelium without compromising epithelial cell viability, and this actually improves barrier function as previously observed in humans. Thus, this Gut-on-a-Chip recapitulates multiple dynamic physical and functional features of human intestine that are critical for its function within a controlled microfluidic environment that is amenable for transport, absorption, and toxicity studies, and hence it should have great value for drug testing as well as development of novel intestinal disease models.

The drug development process has been severely hampered by the need for animal models that are costly, labor-intensive, time-consuming and questionable ethically[1]. Of even greater concern is that animal models often do not predict results obtained in humans,[2-3] and this is a particular problem when addressing challenges relating to metabolism, transport, and oral absorption of drugs and nutrients.[4-5] For these reasons, there has been increasing interest in development of in vitro models of human intestinal function, including cell culture systems that utilize Transwell filter inserts[6-7] which enable trans-epithelial barrier and transport studies,[8-9] and miniaturized microfluidic models that also support long-term culture.[10-14] Others have attempted to recreate the normal three-dimensional (3D) architecture of the intestinal lining in vitro by culturing human intestinal epithelial (e.g. Caco-2) cells on hydrogel substrates that were microengineered to mimic the shape, size and density of human intestinal villi.[11] However, none of the existing in vitro intestinal models recapitulate the mechanically active microenvironment of living intestine (peristaltic motions and intralumenal fluid flow) that is critical for normal organ physiology,[15] as well as for development of Crohn's disease and other intestinal disorders.[16-17] Another limitation of existing in vitro gut models is that it has not been possible to grow living microbes on the luminal surface of cultured intestinal epithelium for extended periods as normally occurs in living intestine. This is a key problem because microbial symbionts normally contribute significantly to intestinal barrier function, metabolism and absorption of drugs and chemicals, and to many diseases.[18-22] Thus, described herein is a more physiologically relevant in vitro model of the human intestine in the form of a human 'Gut-on-a-Chip' that undergoes peristalsis, experiences fluid flow, and supports growth of microbial flora without compromising human cell viability.

Microdevice Design and Fabrication. The Gut-on-a-Chip device was fabricated from a flexible clear polydimethylsiloxane (PDMS; Sylgard, Dow Corning) polymer by adapting a soft lithography technique that was previously used to create a breathing lung-on-a-chip device.[23] The aligned upper and lower microchannels were of same size (150 μm high×1,000 μm wide) and separated by a 30 μm thick PDMS membrane containing 10 μm diameter circular pores with a 25 um spacing (center to center) (FIGS. 12A-12C). As shown in FIG. 13, the upper and lower microchannel layers were individually prepared by casting PDMS prepolymer (15:1 w/w ratio of PDMS to curing agent) on a microfabricated mold of the inverse channel design made of photoresist (SU-8 100, Microchem, Newton, Mass.). The porous membrane (FIG. 12C, right inset) was prepared by casting PDMS prepolymer on a microfabricated silicon wafer containing post arrays with circular pillars (10 μm diameter×30 μm high with 25 μm spacing; MEMS and Nanotechnology Exchange, Reson, Va.), overlaying the prepolymer with a cured, flat, silanized PDMS support layer, placing a 3 kg weight on the setup, and curing the polymer at 60° C. for 12 hours. After peeling the porous PDMS membrane and support layer from the wafer, the surface of the porous membrane was exposed to plasma generated by a laboratory corona treater (BD-20AC, Electro-Technic Products, Inc., Chicago, Ill.), as was the upper microchannel layer. The plasma-treated surfaces of the porous PDMS membrane and upper microchannel layer were then immediately placed in conformal contact. Incubation of the whole setup at 80° C. overnight resulted in irreversible bonding of the two PDMS layers. The PDMS support layer was then peeled off the bottom of the PDMS porous membrane and portions of this membrane located over the lateral vacuum chambers were torn off using forceps to make full-height hollow vacuum chambers. The exposed surface of the torn PDMS membrane and top surface of a lower PDMS microchannel layer with same shape to the upper layer were then exposed to plasma, aligned, pressed together under a stereoscope (Zeiss Discovery V20 Stereo Microscope, Carl Zeiss MicroImaging Gmb, Germany), and cured at 80° C. overnight to produce the entire bonded device containing hollow vacuum chambers on either side of the main microchannel (FIG. 12A and FIG. 13). Tubing (Tygon 3350 silicone tubing, ID 1/32", OD 3/32", Beaverton, Mich.) was connected from fluid medium and vacuum sources to the upper and lower microfluidic channels, respectively, using hub-free stainless steel blunt needles (18G; Kimble Chase, Vineland, N.J.). This allowed control of the flow of culture medium within the central microchannel, and to regulation of the application of vacuum to the side chambers under computer control to exert cyclic mechanical strain to mimic peristaltic motions (FIG. 12D).

Cell Culture. Human Caco-2 intestinal epithelial cells (Caco-2BBE human colorectal carcinoma line[24]) were obtained from the Harvard Digestive Disease Center and grown in Dulbecco's Modified Eagle Medium containing 4.5 g/L glucose (DMEM; Gibco, Grand Island, N.Y.) supplemented with 20% fetal bovine serum (FBS; Gibco), 100 units/mL penicillin, 100 μg/mL streptomycin (Gibco), 100 μg/mL Normocin (Invivogen, San Diego, Calif.), and 25 mM HEPES. Antibiotics were removed from the culture medium for co-culture of Caco-2 cells with living intestinal microbes.

After microdevice fabrication and assembly, the tubing and microfluidic channels were sterilized by flowing 70% (v/v) ethanol through the device and drying the entire system in a 60° C. oven. The dried devices were then exposed to ultraviolet light and ozone (UVO Cleaner 342, Jelight Company Inc., Irvine, Calif.) simultaneously for 30 min. An ECM solution[25-27] containing rat type I collagen (50 μg/mL; Gibco) and Matrigel (300 μg/mL; BD Biosciences, Bedford, Mass.) in serum-free DMEM was injected into the microchannels and incubated at 37° C. for 2 hours, after which the microchannels were perfused with culture medium. Caco-2 cells harvested with trypsin/EDTA solution (0.05%; Gibco) were plated on the top surface of the ECM-coated porous membrane ($1.5 \times 10^5$ cells/cm$^2$) by gently pulling the cell solution into upper microchannel using a sterile syringe (1 mL Tuberculin slip tip; BD, Franklin Lakes, N.J.) and needle (25G 5/8; BD). At this cell density, neither aggregation nor superposition of cells was observed in the microchannel after seeding into the Gut-on-a-Chip device. Caco-2 cells attached to the ECM-coated PDMS surface within ~30 min and generated cell-cell adhesions within 1 hour (not shown). After 1 hour, a syringe pump (BS-8000; Braintree Scientific Inc., Braintree, Mass.) was used to perfuse culture medium continuously through the upper channel at a constant flow rate (30 μL/hr, which produces 0.02 dyne/cm$^2$ shear stress) for the first day of culture to make sure that the Caco-2 cells established an intact monolayer, and then medium was flowed at a same rate through both the upper and lower channels thereafter.

To mechanically deform the Caco-2 monolayer in a cyclic manner that mimics peristaltic motions of the intestine, cyclic suction was applied to tubing connected to the vacuum chambers (FIGS. 12A, 12B) using a computer-controlled FX5K Tension instrument (Flexcell International Corporation, Hillsborough, N.C.). This device is capable of unidirectional elongation of the porous membrane in Gut-on-a-Chip by up to ~50%; however, a cyclic stretching regimen (10% mean cell strain, 0.15 Hz frequency) that more closely mimics the mechanical microenvironment that epithelial cells experience in the living human intestine in vivo[16,28] was applied in these studies. The relation between applied pressure, distortion of the porous membrane substrate and cell deformation was first quantified over a broad range (0 to ~30% strain) to characterize the control parameters of the device (FIG. 12E).

Control studies were carried out using static cultures of Caco-2 cells in Transwell plates (Corning Inc., Lowell, Mass.) containing porous polyester membrane inserts (0.33 cm$^2$, 0.4 µm pores) that were pre-coated with the same ECM mixture of type I collagen and Matrigel used in the Gut-on-a-Chip device. Caco-2 cells also were plated at the same density (1.5×10$^5$ cells/cm$^2$) with medium being refreshed every other day to both the apical and basolateral side of the Transwell chamber.

Epithelial Barrier Measurements. The integrity of the human intestinal epithelial cell monolayer resulting from establishment of apical tight junctions was evaluated by staining for the tight junctional protein, occluidin,[29] using confocal immunofluorescence microscopy and by measuring trans-epithelial electrical resistance (TEER). In Transwell cultures, TEER was measured using a Millicell ERS meter (Millipore, Bedford, Mass.) coupled to a chopstick-like electrode, and TEER values (Ω cm$^2$) were determined by subtracting the baseline resistance value measured in the absence of cells and then multiplying the remaining 'specific' resistance value (Ω) times the cell culture surface area (cm$^2$). The TEER of the Caco-2 monolayer cultured in the Gut-on-a-Chip was measured using a voltage-ohm meter (87V Industrial Multimeter, Fluke Corporation, Everett, Wash.) coupled to Ag/AgCl electrode wires (0.008" in diameter; A-M systems, Inc., Sequim, Wash.); control studies confirmed that similar TEER results were obtained with both methods. Again, the baseline resistance value measured in the absence of cells was subtracted from results obtained with the Caco-2 monolayer, and specific TEER values were determined by multiplying the specific resistance times the total cell culture surface area on the PDMS membrane (Table 1).

Measurement of Aminopeptidase Activity. Human intestinal epithelial cell functionality was measured by quantitating the specific activity of an apical brush border aminopeptidase enzyme that is expressed by differentiated human intestinal Caco-2 cell monolayers[30] using L-alanine-4-nitroanilide hydrochloride (A4N; Sigma, St. Louis, Mo.) as a substrate. In Transwell studies, A4N substrate solution (1.5 mM in medium) was applied to the top chamber of cells cultured for 5 or 21 days and after incubation at 37° C. for 2 hours, the solution (70 µL) in the top chamber was transferred to a 96 well plate (Black/clear flat bottom, BD Falcon, Franklin Lakes, N.J.) where the cleavage product (i.e. 4-nitroaniline) was quantified in a microplate reader (SpectraMax M5, Molecular Devices, Sunnyvale, Calif.) at 405 nm using culture medium as a reference. The specific activity of aminopeptidase was obtained by dividing the total activity by the total cell number. The actual amount of cleaved product was estimated based on the calibration curve of 4-nitroaniline.

To measure the specific activity of aminopeptidases in the Gut-on-a-Chip, the A4N solution was flowed at 30 µL/hr through the upper microchannel of the device containing a Caco-2 monolayer cultured in the presence or absence of cyclic mechanical strain (10% strain, 0.15 Hz in frequency) for 5 days. Samples (30 µL) collected every hour from the outlet of the upper microchannel were diluted to the same volume (70 µL) that was used to analyze the Transwell samples and transferred to a 96 well plate (Black/clear flat bottom, BD Falcon) where optical densities were measured as described above.

Paracellular Permeability Measurements. The apparent permeability coefficient ($P_{app}$, cm/sec) of the intestinal cell monolayer was determined after tight junctional integrity was established (TEER≥600 Ω·cm$^2$) by measuring the transport of fluorescein isothiocyanate-labeled dextran (FD20; 20 KDa; Sigma, St. Louis, Mo.) over time. In Transwell studies, the FD20 was applied (200 µL; 1 mg/mL) to the apical surface of the epithelium in the top chamber, and aliquots (70 µL) were removed from the lower chamber every 15 min (700 µL total volume) while simultaneously replenishing with the same volume of fresh culture medium. Fluorescence intensity (490 nm excitation/520 nm emission) of the samples collected from the lower chamber were measured immediately to quantify the amount of FD20 transported from the apex to the basolateral surface of the cell. After subtracting the baseline fluorescence value measured in culture medium alone, the apparent permeability coefficient ($P_{app}$) was calculated according to $P_{app}$ (cm/sec)=(dQ/dt)(1/$AC_o$) where dQ/dt is the steady-state flux (g/sec), A is the culture surface area (cm$^2$) and $C_o$ is the initial concentration (g/L) of the FD20 solution applied to the apical cell surface.[31]

In studies carried out using the Gut-on-a-Chip, the FD20 solution was perfused through the upper channel, and sample aliquots (30 µL) collected every hour from the outlet of a lower channel were analyzed to quantitate the amount of FD20 that was transported across the Caco-2 paracellular barrier. The Caco-2 monolayer in the microchannel was cultured in the presence of medium flow (30 µL/hr), with or without exposure to cyclic mechanical strain (10% strain, 0.15 Hz in frequency) for 5 days.

Microbial Studies. To study physiologically relevant human intestinal epithelial cell-microbe interactions, a strain of *Lactobacillus rhamnosus* GG (LGG) was obtained from American Type Culture Collection (ATCC 53103; Manassas, Va.) that was originally isolated from human gut.[32] LGG cells were grown in autoclaved Lactobacilli MRS broth (BD Diagnostic, Sparks, Md.) in a humidified incubator (37° C., 5% $CO_2$) without shaking overnight prior to transfer to the apical surface of Caco-2 cell monolayers that were pre-cultured for ~4-5 days to developed relevant intestinal barrier integrity (TEER≥600 Ω·cm$^2$). The cell culture medium was switched to antibiotic-free medium for 12 hours prior to seeding of the LGG cells (~1.0×10$^7$ CFU/mL, final cell density). LGG cells placed on the apical surface of Caco-2 cells in Transwell cultures were incubated for 1.5 hr, carefully washed free of non-adherent cells with two changes of antiobiotic-free culture medium, and incubated in similar medium for extended culture as indicated. The same method was used for studies in the Gut-on-a-Chip, except that after the attachment period, antibiotic-free medium was perfused through both upper and lower microchannels at 40 µL/hr with the cyclic stretching (10% strain, 0.15 Hz in frequency).

Microbial β-Galactosidase Activity Measurements. To analyze the viability and function of LGG cells in co-culture studies, the catalytic activity of LGG β-galactosidases was determined by measuring the ability of the cultured microbes to cleave the enzyme substrate, O-nitrophenyl β-D-galactopyranoside (ONPG; Sigma, St. Louis, Mo.). For these studies, LGG and Caco-2 cells were co-cultured in the gut-on-chip and perfused with antibiotic-free medium (40 µL/hr) for 48 hr before ONPG was added to the medium (30 µg/mL). Samples (30 µL) collected every hour from the outlet of the upper microchannel were analyzed by measuring optical density (420 nm) using a SpectraMax M5 instrument (Molecular Devices, Sunnyvale, Calif.) to quantify the amount of product (i.e. O-nitrophenol) released by β-galactosidases in the LGG cells. The amount of cleaved product was estimated based on the calibration curve of O-nitrophenol.

Morphological Studies. Cell images were recorded during culture using a Moticam 2500 camera (Motic China Group Co., Ltd.) with imaging software (Motic images plus 2.0; Motic China Group Co., Ltd.) on a Zeiss Axiovert 40CFL phase contrast microscope. To visualize cell shape and polarity, F-actin, nuclei, and mucin were stained in Caco-2 cell monolayers that were fixed in 4% paraformaldehyde and permeabilized in 0.3% Triton-X-100 (Sigma, St. Louis, Mo.) using fluorescein isothiocyanate (FITC)-phalloidin (Sigma, St. Louis, Mo.), 4',6-diamidino-2-phenylindole, dihydrochloride (DAPI; Molecular Probe, Eugene, Oreg.), and Mucin 2 antibodies[33] (mouse monoclonal antibody; abcam, Cambridge, Mass.), respectively. Following fluorescence staining, the cells were scanned using an inverted laser scanning confocal microscope (Leica SP5 X MP, Germany) equipped with a photomultiplier tube and coupled to a 405 nm laser and a white light laser (489-670 nm). To visualize epithelial tight junctions, immunofluorescence staining was performed using anti-occludin antibodies (mouse monoclonal antibody-Alexa Fluor 594; Molecular Probe, Eugene, Oreg.), and samples were visualized on a Zeiss Axio Observer Z1 epi-fluorescence microscope coupled to a CCD camera (CoolSNAP HQ$^2$, 1392×1040 resolution; Photometrics, Tucson, Ariz.); computerized image analysis of recorded images was carried out using MetaMorph image software (Molecular Devices).

Statistical Analysis. All results are expressed as mean±standard error (SEM). For the statistical evaluation of quantified data, a one-way analysis of variance (ANOVA) with Tukey-Kramer multiple comparisons test was performed using GraphPad InStat version 3.10 (GraphPad Software Inc., San Diego Calif.). Differences were considered statistically significant when $p<0.05$.

Calculation of Shear Stress. Shear stress ($\tau$, dyne/cm$^2$) was calculated based on the following equation,[63] $\tau=6 \mu Q/h^2 w$, where t is viscosity of the culture medium (g/cm·s), Q is volumetric flow rate (cm$^3$/s), and w (cm) and h (cm) are width and height of the microchannel, respectively.

Measurement of β-Galactosidase Activity. For measuring the catalytic activity of β-galactosidases, O-nitrophenyl-β-D-galactopyranoside (ONPG; Sigma, St. Louis, Mo.) was used as described. LGG cell culture was carried out in MRS medium, then LGG cells were harvested at exponential phase. After LGG cells were washed twice in antibiotic-free cell culture medium, cell density was adjusted to ~1.0×10$^8$ CFU/mL in ONPG-containing antibiotic-free cell culture medium (30 μg/mL, final ONPG concentration), then samples were immediately incubated at 37° C. under 5% CO$_2$ in a humidified atmosphere. Samples intermittently taken for 12 hours were centrifuged, and optical density of supernatant was measured at 420 nm (SpectraMax M5, Molecular Devices); fresh culture medium was used as a reference. Caco-2 cells were cultured in an ECM-coated 24-well plates (Falcon, BD) for 2 weeks, and culture medium was then switched to antibiotic-free medium for 12 hours prior to performing ONPG assay. After ONPG solution (30 μg/mL) was applied to the Caco-2 culture plate, sample aliquots was intermittently taken from the culture medium, and optical density was measured at 420 nm.

Results and Discussion

Gut-on-a-Chip Microsystem Design. The embodiment of the Gut-on-a-Chip microdevice was designed to mimic the dynamic mechanical microenvironment of the gut, support perfusion-based long-term cell culture with microbial symbionts, and enable analysis of intestinal epithelial barrier functions in vitro. To accomplish these goals, the microsystem design incorporated two layers of closely apposed microfluidic channels separated by a thin porous membrane coated with ECM and lined by human Caco-2 intestinal epithelial cells (FIG. 12A). Culture medium was perfused through both microchannels (10-100 μL/min) to mimic fluid flow and shear stresses normally experienced in the human intestine.[34-36] To create rhythmic mechanical deformations of the epithelial cell monolayer similar to those caused by peristaltic motions of the human intestine, cyclic suction regulated by a computer-controlled vacuum manifold was applied to the full-height, hollow, vacuum chambers positioned on either side of the microchannels to repeatedly stretch and relax the elastic, ECM-coated porous membrane (FIG. 12D). Phase contrast microscopic analysis of cell shape in human intestinal epithelial monolayers grown under these conditions confirmed that both substrate distortion and cell deformation increased linearly from 0 to ~30% as the level of suction pressure was raised from 0 to 45 kPa (FIGS. 12A-12E).

Impact of Mimicking the Gut Microenvironment on Epithelial Organization. To explore the physiological relevance of mimicking the physical microenvironment of the intestine, Caco-2 cells were grown either in a static Transwell chamber without fluid flow and mechanical strain (FIG. 14A) or in the Gut-on-a-Chip microfluidic device with either flow alone (FIG. 14B) or flow plus cyclic mechanical strain (FIG. 14C). Caco-2 cells commonly must be grown in the Transwell system for at least 3 weeks to exhibit differentiated intestinal barrier functions, and thus we analyzed cells at 21 days in these static cultures. In preliminary studies, it was noticed that well-defined epithelial monolayers formed much more quickly in the microfluidic device, and hence, these studies comparing epithelial monolayer functions with the Transwell cultures were able to be carried out after only 3 days of culture in the microfluidic system.

Figure 14A:
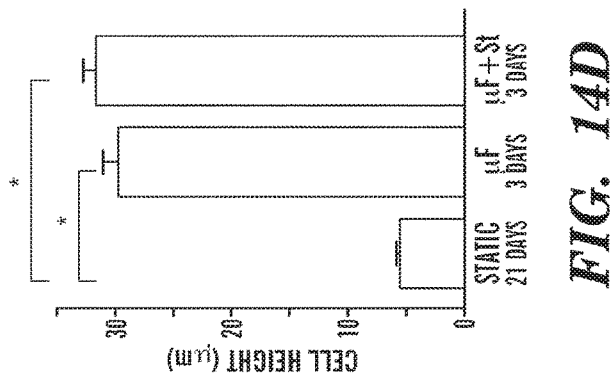
Figure 14A:
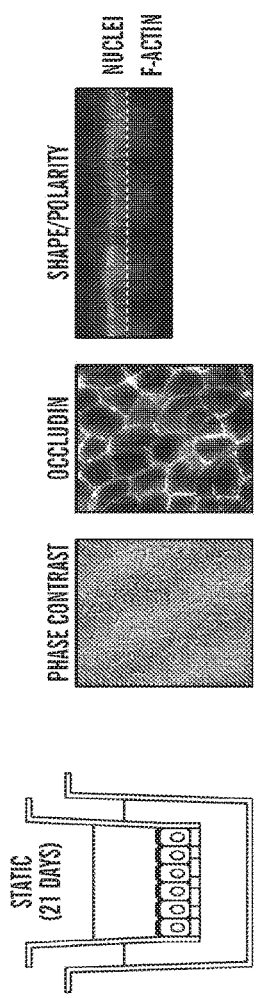
Figure 14B:
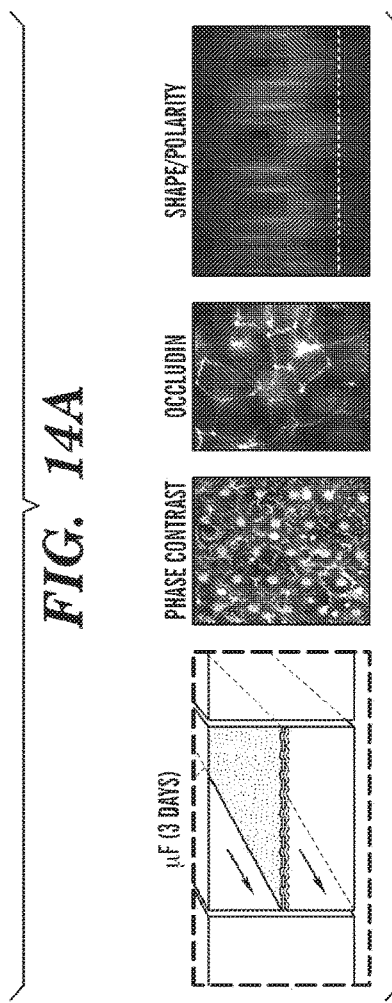
Figure 14C:
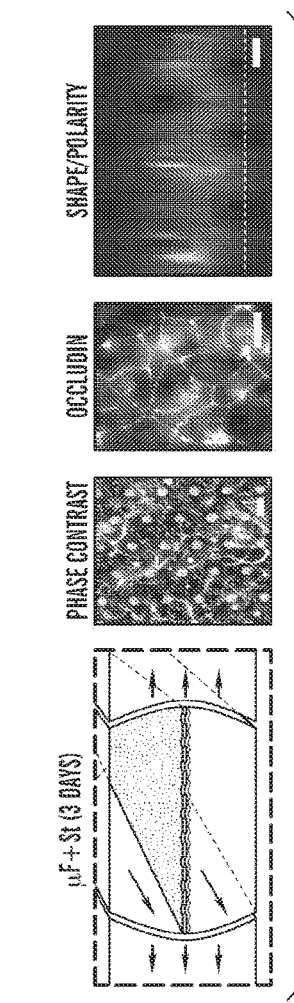

Phase contrast and immunofluorescence microscopic studies using antibodies directed against the tight junction protein, occludin, confirmed that Caco-2 cells formed confluent polygonal epithelial monolayers with well developed tight junctions under all three culture conditions, even though cells in the microdevice were cultured for a much shorter time (FIGS. 14A-14C). However, confocal fluorescence microscopic analysis of F-actin distribution and nuclear position revealed that epithelial cells grown under static conditions in the Transwell were highly flattened and almost squamous in form (FIG. 14A). In contrast, cells grown in the presence of fluid flow at a rate (30 uL/hr; 0.02 dyne/cm$^2$ shear stress) similar to that experienced by human intestine[34,36], with or without concomitant cyclic strain, were almost 6-fold taller in size (FIG. 14D) and hence, exhibited polarized epithelial cell forms with basal nuclei (FIGS. 14B-14C). In fact, cells under fluid flow were about the same columnar shape and size (30-40 μm high) that has been reported for cells within healthy intact human intestinal epithelium in vivo.[37]

One possibility is that this effect on cell morphology could be an artifact of placement within a microchannel device compared with a Transwell chamber. However, when the fluid flow rate was lowered in the microfluidic channel to a minimal level (10 μL/hr), the cells failed to increase in height and looked much like they did in the static Transwell system[38] (FIG. 14A), whereas increasing the rate to 100 μL/hr had no additive effect beyond what we observed at 30 μL/hr (FIGS. 18A-18C). Thus, application of physiological fluid flow and shear stress across the apical surface of the intestinal epithelium accelerates cell differentiation as measured by an increase in height and polarization of these cells within 3 days of culture under conditions where cells in the Transwell systems remained flat even after 3 weeks. Moreover, flow or shear stress was the critical determinant of this response as cyclic strain did not produce any significant additive effect (FIG. 14D).

Figure 15A:
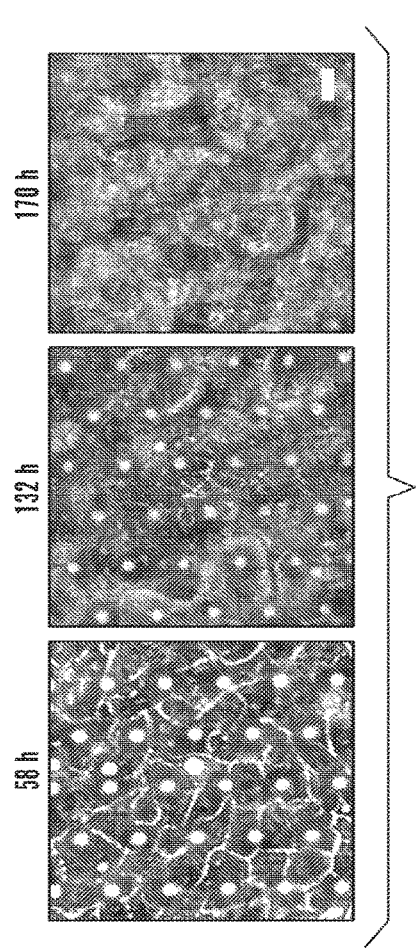
FIGS. 15A-15B demonstrate the spontaneous formation of intestinal villi by Caco-2 cells cultured in the Gut-on-a-Chip.
Figure 15B:
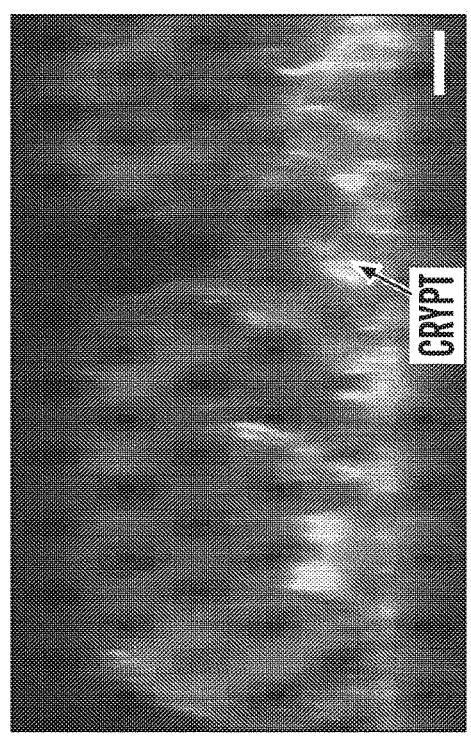

Interestingly, when Caco-2 cells were cultured in the Gut-on-a-Chip microdevice with flow and cyclic strain for longer times, it was found that the originally planar columnar epithelium spontaneously grew to form undulations and folds (FIG. 15A). When the vertical section was analyzed by immunofluorescence confocal microscopy, these folds were found to exhibit the morphology of normal intestinal villi lined by polarized columnar epithelial cells with basal nuclei and separated by crypts (FIG. 15B). The apical surfaces of epithelial cells within these villous structures stained positively for mucin 2, which is where this mucoprotein is deposited in vivo.[39] The timing of villi formation observed in this in vitro model (on the order of weeks) is also consistent with the rate of villous renewal observed in vivo.[40-41] It is believed that spontaneous formation of intestinal villi by Caco-2 cells has never been reported previously, and this response which occurs after plating on planar ECM substrates appears to depend directly upon recapitulation of the mechanical microenvironment of the normal intestine that experiences low levels of fluid flow (and shear stress), as well as cyclic peristaltic motions.

Reconstitution of Intestinal Barrier Functions In Vitro. The Transwell model of intestinal epithelial barrier function that is often used as a tool for drug screening applications as well as cell biological studies,[8, 42] involves culture of Caco-2 cells on a porous Transwell membrane and tight junctional integrity is measured by quantifying TEER. Therefore, TEER of Caco-2 monolayers grown under static Transwell conditions versus those that form in the Gut-on-a-Chip device with flow (30 µL/hr) in the presence or absence of physiological cyclic strain (10%; 0.15 Hz) were compared. These studies revealed that cells grown under all three culture conditions increased their TEER over the first 6 days after plating and then maintained similar high levels for at least another 4 to 5 days of culture. However, cells in the microfluidic device with or without strain displayed peak TEER levels that were 3- to 4-fold higher than those of cells in static Transwell culture (FIG. 16A).

Figures 16A, 16B, 16C:
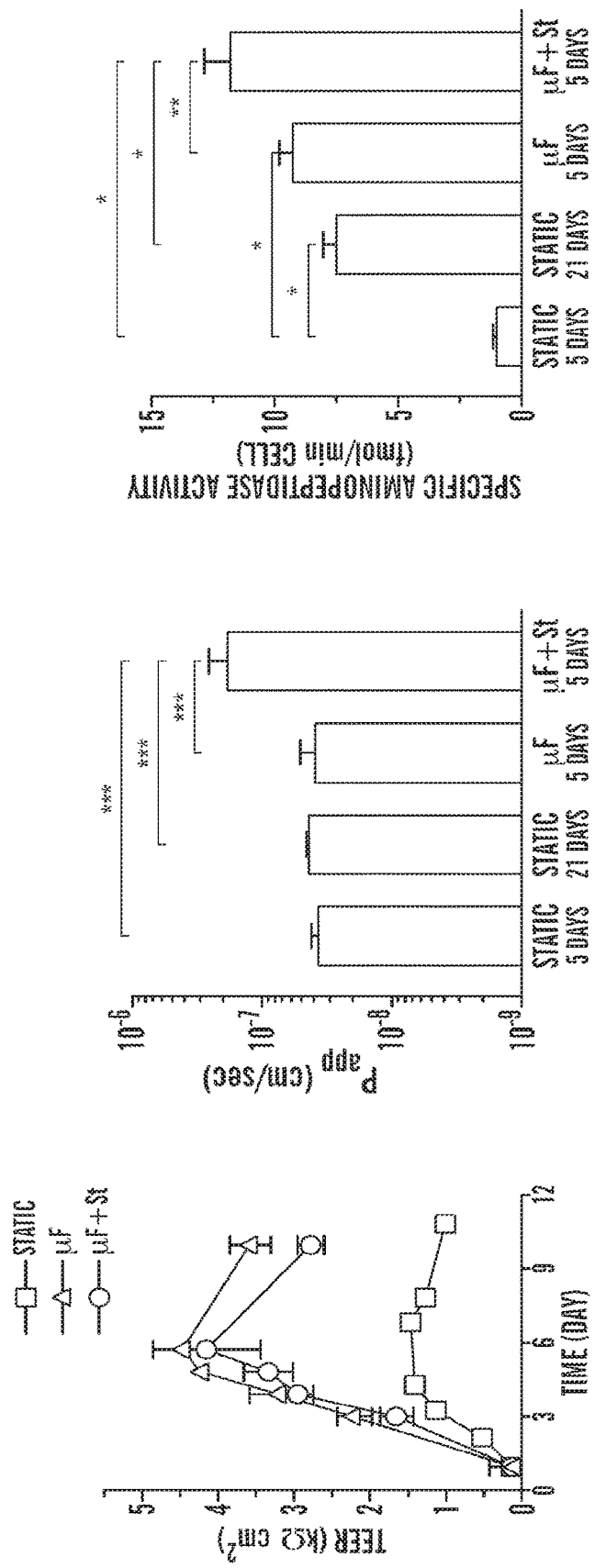
FIGS. 16A-16C depict the evaluation of intestinal barrier functions and differentiation of a Caco-2 monolayer cultured in either the Transwell (Static) or microfluidic Gut-on-a-Chip in the absence (µF) or presence (µF+St) of cyclic strain.

The apparent permeability coefficient ($P_{app}$) of the intestinal epithelium was measured using fluorescent dextran (FD20), which characterizes the paracellular barrier function of intestinal epithelium due to pores associated with tight junctions.[31] It was found that the $P_{app}$ of cells was the same ($\sim 4 \times 10^{-8}$ cm/sec) whether Caco-2 cells were cultured for 5 or 21 days in Transwell chambers (FIG. 16B). Cells cultured for 5 days in the microfluidic device with fluid flow alone (30 µL/hr) also exhibited a similar $P_{app}$; however, additional application of cyclic mechanical strain (10% strain, 0.15 Hz+30 µL/hr flow) induced more than a 4-fold increase in paracellular permeability (FIG. 16B).

These results are consistent with published studies showing that Caco-2 cell monolayers in Transwell cultures display lower paracellular permeability values than those observed in human or animal intestine in vivo.[43-45] It has been proposed that this low level of permeability could result from the presence of a thick unstirred fluid layer in the static Transwell culture, which might limit diffusion.[46] One might then expect that fluid flow would increase paracellular permeability by producing fluid shear stress that decreases the thickness of the unstirred diffusion layer[43-44, 47], but fluid flow alone did not alter paracellular permeability in the system described herein. Instead, as described herein, cyclic strain increased paracellular permeability, and this occurred under conditions that did not change TEER in these cell monolayers (FIG. 16B versus FIG. 16A), suggesting that mechanical distortion might alter paracellular mechanisms of transport directly. Cyclic mechanical strain can increase transport of nanoparticles across lung epithelial and endothelial cell monolayers as a result of increased transcytosis,[23] and hence, it is possible that a similar mechanism could come into play here as well.

Next, the catalytic activity of epithelial cell aminopeptidases was analyzed to determine whether fluid flow and mechanical strain alter cytodifferentiation in human intestinal epithelial cells. Caco-2 cell differentiation measured by expression of aminopeptidase activity increased >7-fold over within cells cultured for 21 days compared to 5 days in the static Transwell system (FIG. 16C), which is consistent with previously published findings.[48] Importantly, culture of cells under fluid flow (30 µL/hr) in the microfluidic device greatly accelerated this response, producing almost a 9-fold increase in aminopeptidase activity after only 5 days in culture, and an even greater increase was produced when cells were grown in the Gut-on-a-Chip that applies the same fluid flow and cyclic mechanical strain (10% strain, 0.15 Hz) simultaneously. These results are consistent with a past study which showed that cyclic strain can similarly increase expression of expression of intestinal differentiation-specific enzyme activities in Caco-2 cells.[25]

Host-Microflora Co-Culture. One of the most crucial components of human gut physiology that has never been modeled effectively in vitro is the normal presence of microbial communities in the lumen of the gut.[49] To explore whether the highly differentiated intestinal epithelium produced in the Gut-on-a-Chip could support co-culture of microbial flora, the normal intestinal microbe, *Lactobacillus rhamnosus* GG (LGG) was cultured on the apical surface of Caco-2 cell monolayer, and cells cultured in Transwell chambers under static conditions were used as controls. After microfluidic co-culture with continuous flow (40 µL/hr) and cyclic strain (10%, 0.15 Hz) for 96 hours, microcolonies of LGG cells still remained tightly adherent to the surface of a Caco-2 monolayer (FIG. 17A). Live/dead staining of the culture with calcein-AM and ethidium homodimer-1, respectively, confirmed that the Caco-2 epithelial cells remained fully (>95%) viable after co-culture with LGG under these conditions (FIG. 17B). LGG express a bacterial-specific β-galactosidase activity when grown alone in culture whereas this is not expressed by intestinal epithelial cells (FIG. 19). When we measured β-galactosidase activity in the top chamber of the co-cultures, it too remained high, thus confirming that the LGG cells also remained viable under these culture conditions (FIG. 17D).

Importantly, not only was the intestinal cell monolayer able to maintain normal barrier functions under these co-culture conditions with living microbes growing on its apical surface, barrier integrity measured by quantitating TEER actually improved over time (FIG. 17C). This result is consistent with the finding that probiotic strains of bacteria, including LGG, have been reported to increase intestinal epithelial integrity in vitro[50] and enhance intestinal barrier function in humans.[51] In contrast, TEER dissipated over the first day of co-culture in the static Transwell system and could not be measured at all after 48 hours (FIG. 17C) due to death and complete detachment of the epithelial monolayer.

The human microbiome plays a central role in intestinal health and disease,[18, 52-53] and so development of an in vitro platform to study host-microbe interplay should be of great interest to cell biologists and physiologists, as well as pharmaceutical scientists.[54-55] Past studies have carried out short-term co-culture of intestinal epithelial cells with living bacteria to study microbial adherence,[56] invasion,[57] translocation,[58] and biofilm formation.[59] But long-term co-culture of microbes with host cells has not been possible due to microbial overgrowth and loss of epithelial viability. This is likely due to difficulties in matching growth conditions between the host cell and microbe,[59] controlling the population density of microbes in antibiotic-free culture condition,[60] or restricting production of metabolites (e.g. organic acids) by microbial cells.[61-62] In the experiments described herein, LGG cells grew without constraint in the stagnant apical chamber of the Transwell system, causing drastic decrease of medium pH (pH 2.5-3.0) that is not consistent with intestinal epithelial cell survival (not shown). Importantly, however, the microfluidic nature of the Gut-on-a-Chip provides a way to overcome this challenge because it effectively functions as a continuous flow bioreactor. Specifically, the dilution rate of the culture medium in Gut-on-a-Chip ($\sim$8.0 h$^{-1}$) is much higher than the specific growth rate of LGG in the culture medium ($\sim$0.2 h$^{-1}$), which permits clearance of organic acids and unbound LGG cells. LGG cells that were tightly adherent on the surface of a Caco-2 monolayer remained in the Gut-on-a-Chip device while all non-adherent LGG cells were washed out, which prevented unrestrained overgrowth of the cultures. Given that intestinal epithelial integrity significantly increased in the presence of LGG co-cultures, the presence of microbes apparently provides normal microenvironmental cues that enhance epithelial cell functions (e.g. mucin secretion) that are necessary to maintain this dynamic interface, which is consistent with human clinical studies.[51]

The embodiment of the human Gut-on-a-Chip microdevice described in this Example provides a controlled microplatform to study and perturb critical gut functions in the presence of relevant physiological cues, including cyclic mechanical strain, fluid flow and coexistence of microbial flora. Characterization of this device revealed that recapitulating the low level of fluid flow and shear stress experienced in the living intestine is sufficient to promote accelerated intestinal epithelial cell differentiation, formation of 3D villi-like structures, and increased intestinal barrier function, and that addition of cyclic mechanical strain that mimics normal peristaltic motions further enhances these responses. Moreover, once differentiated within the Gut-on-a-Chip device, the intestinal epithelium can support growth of microbial flora that normally lives within the human intestine. The human peristaltic Gut-on-a-Chip may therefore facilitate study of mechanoregulation of intestinal function, as well as host-microbe symbiosis and evolution. Given that it effectively recapitulates many complex functions of the normal human intestine, it also may become an essential platform for drug screening and toxicology testing.

REFERENCES FOR EXAMPLE 2 AND BACKGROUND OF THE INVENTION SECTIONS

1. J. C. Davila, R. J. Rodriguez, R. B. Melchert and D. Acosta, Jr., Annu Rev Pharmacol Toxicol, 1998, 38, 63-96.
2. J. A. Kramer, J. E. Sagartz and D. L. Morris, Nature Reviews Drug Discovery, 2007, 6, 636-649.
3. H. Olson, G. Betton, D. Robinson, K. Thomas, A. Monro, G. Kolaja, P. Lilly, J. Sanders, G. Sipes, W. Bracken, M. Dorato, K. Van Deun, P. Smith, B. Berger and A. Heller, Regulatory Toxicology and Pharmacology, 2000, 32, 56-67.
4. K. M. Giacomini, S. M. Huang, D. J. Tweedie, L. Z. Benet, K. L. R. Brouwer, X. Y. Chu, A. Dahlin, R. Evers, V. Fischer, K. M. Hillgren, K. A. Hoffmaster, T. Ishikawa, D. Keppler, R. B. Kim, C. A. Lee, M. Niemi, J. W. Polli, Y. Sugiyama, P. W. Swaan, J. A. Ware, S. H. Wright, S. W. Yee, M. J. Zamek-Gliszczynski, L. Zhang and T. International, Nature Reviews Drug Discovery, 2010, 9, 215-236.
5. J. Hodgson, Nat Biotechnol, 2001, 19, 722-726.
6. E. Le Ferrec, C. Chesne, P. Artusson, D. Brayden, G. Fabre, P. Gires, F. Guillou, M. Rousset, W. Rubas and M. L. Scarino, Atla-Alternatives to Laboratory Animals, 2001, 29, 649-668.
7. I. D. Angelis and L. Turco, Current protocols in toxicology/editorial board, Mahin D. Maines (editor-in-chief) . . . [et al.], 2011, Chapter 20.
8. K.-J. Kim, in Cell Culture Models of Biological Barriers, ed. C.-M. Lehr, Taylor & Francis, New York, 1st edn., 2002, ch. 3, pp. 41-51.
9. I. J. Hidalgo, T. J. Raub and R. T. Borchardt, Gastroenterology, 1989, 96, 736-749.
10. G. J. Mahler, M. B. Esch, R. P. Glahn and M. L. Shuler, Biotechnology and Bioengineering, 2009, 104, 193-205.
11. J. H. Sung, J. J. Yu, D. Luo, M. L. Shuler and J. C. March, Lab on a Chip, 2011, 11, 389-392.
12. J. H. Sung, C. Kam and M. L. Shuler, Lab on a Chip, 2010, 10, 446-455.
13. H. Kimura, T. Yamamoto, H. Sakai, Y. Sakai and T. Fujii, Lab on a Chip, 2008, 8, 741-746.
14. Y. Imura, Y. Asano, K. Sato and E. Yoshimura, Analytical Sciences, 2009, 25, 1403-1407.
15. I. R. Sanderson, American Journal of Clinical Nutrition, 1999, 69, 1028S-1034S.
16. C. P. Gayer and M. D. Basson, Cell Signal, 2009, 21, 1237-1244.
17. M. D. Basson and C. P. Coppola, Metabolism-Clinical and Experimental, 2002, 51, 1525-1527.
18. L. V. Hooper, Trends in Microbiology, 2004, 12, 129-134.
19. J. C. Arthur and C. Jobin, Inflammatory Bowel Diseases, 2011, 17, 396-409.
20. H. Sokol and P. Seksik, Current Opinion in Gastroenterology, 2010, 26, 327-331.
21. J. L. Round and S. K. Mazmanian, Nature Reviews Immunology, 2009, 9, 313-323.
22. J. R. Turner, Nature Reviews Immunology, 2009, 9, 799-809.
23. D. Huh, B. D. Matthews, A. Mammoto, M. Montoya-Zavala, H. Y. Hsin and D. E. Ingber, Science, 2010, 328, 1662-1668.
24. M. D. Peterson and M. S. Mooseker, J Cell Sci, 1992, 102 (Pt 3), 581-600.
25. M. D. Basson, G. D. Li, F. Hong, O. Han and B. E. Sumpio, Journal of Cellular Physiology, 1996, 168, 476-488.
26. J. H. Zhang, W. Li, M. A. Sanders, B. E. Sumpio, A. Panja and M. D. Basson, Faseb Journal, 2003, 17, 926-+.
27. M. D. Basson, G. Turowski and N. J. Emenaker, Experimental Cell Research, 1996, 225, 301-305.
28. M. D. Basson, Digestion, 2003, 68, 217-225.
29. M. Furuse, T. Hirase, M. Itoh, A. Nagafuchi, S. Yonemura and S. Tsukita, Journal of Cell Biology, 1993, 123, 1777-1788.
30. C. Piana, I. Gull, S. Gerbes, R. Gerdes, C. Mills, J. Samitier, M. Wirth and F. Gabor, Differentiation, 2007, 75, 308-317.

31. I. Hubatsch, E. G. Ragnarsson and P. Artursson, Nat Protoc, 2007, 2, 2111-2119.
32. M. Saxelin, Food Reviews International, 1997, 13, 293-313.
33. L. G. Durrant, E. Jacobs and M. R. Price, European Journal of Cancer, 1994, 30A, 355-363.
34. R. G. Lentle and P. W. M. Janssen, Journal of Comparative Physiology B-Biochemical Systemic and Environmental Physiology, 2008, 178, 673-690.
35. S. P. Olesen, D. E. Clapham and P. F. Davies, Nature, 1988, 331, 168-170.
36. T. Ishikawa, T. Sato, G. Mohit, Y. Imai and T. Yamaguchi, Journal of Theoretical Biology, 2011, 279, 63-73.
37. T. F. Bullen, S. Forrest, F. Campbell, A. R. Dodson, M. J. Hershman, D. M. Pritchard, J. R. Turner, M. H. Montrose and A. J. Watson, Lab Invest, 2006, 86, 1052-1063.
38. G. Wilson, I. F. Hassan, C. J. Dix, I. Williamson, R. Shah, M. Mackay and P. Artursson, Journal of Controlled Release, 1990, 11, 25-40.
39. S. B. Ho, G. A. Niehans, C. Lyftogt, P. S. Yan, D. L. Cherwitz, E. T. Gum, R. Dahiya and Y. S. Kim, Cancer Research, 1993, 53, 641-651.
40. E. Marshman, C. Booth and C. S. Potten, Bioessays, 2002, 24, 91-98.
41. F. Radtke and H. Clevers, Science, 2005, 307, 1904-1909.
42. P. Shah, V. Jogani, T. Bagchi and A. Misra, Biotechnol Prog, 2006, 22, 186-198.
43. A. Avdeef and K. Y. Tam, Journal of Medicinal Chemistry, 2010, 53, 3566-3584.
44. H. Lennernas, K. Palm, U. Fagerholm and P. Artursson, International Journal of Pharmaceutics, 1996, 127, 103-107.
45. S. Y. Yee, Pharmaceutical Research, 1997, 14, 763-766.
46. I. J. Hidalgo, K. M. Hillgren, G. M. Grass and R. T. Borchardt, Pharmaceutical Research, 1991, 8, 222-227.
47. H. Lennernas, Xenobiotica, 2007, 37, 1015-1051.
48. S. Howell, A. J. Kenny and A. J. Turner, Biochemical Journal, 1992, 284, 595-601.
49. F. Shanahan, Best Practice & Research in Clinical Gastroenterology, 2002, 16, 915-931.
50. H. W. Fang, S. B. Fang, J. S. C. Chiau, C. Y. Yeung, W. T. Chan, C. B. Jiang, M. L. Cheng and H. C. Lee, Journal of Medical Microbiology, 2010, 59, 573-579.
51. C. Dai, D.-H. Zhao and M. Jiang, International journal of molecular medicine, 2012, 29, 202-208.
52. P. J. Turnbaugh, R. E. Ley, M. Hamady, C. M. Fraser-Liggett, R. Knight and J. I. Gordon, Nature, 2007, 449, 804-810.
53. F. H. Karlsson, I. Nookaew, D. Petranovic and J. Nielsen, Trends in Biotechnology, 2011, 29, 251-258.
54. J. K. Nicholson, E. Holmes and I. D. Wilson, Nat Rev Microbiol, 2005, 3, 431-438.
55. P. W. Lin, T. R. Nasr, A. J. Berardinelli, A. Kumar and A. S. Neish, Pediatric Research, 2008, 64, 511-516.
56. G. Chauviere, M. H. Coconnier, S. Kerneis, J. Fourniat and A. L. Servin, Journal of General Microbiology, 1992, 138, 1689-1696.
57. M. H. Coconnier, M. F. Bernet, S. Kerneis, G. Chauviere, J. Fourniat and A. L. Servin, Fems Microbiology Letters, 1993, 110, 299-305.
58. P. Harvey, T. Battle and S. Leach, Journal of Medical Microbiology, 1999, 48, 461-469.
59. J. Kim, M. Hegde and A. Jayaraman, Lab on a Chip, 2010, 10, 43-50.
60. G. Zoumpopoulou, E. Tsakalidou, J. Dewulf, B. Pot and C. Grangette, International Journal of Food Microbiology, 2009, 131, 40-51.
61. M. Moussavi and M. C. Adams, Current Microbiology, 2010, 60, 327-335.
62. H. Annuk, J. Shchepetova, T. Kullisaar, E. Songisepp, M. Zilmer and M. Mikelsaar, Journal of Applied Microbiology, 2003, 94, 403-412.
63. J. Shao, L. Wu, J. Wu, Y. Zheng, H. Zhao, Q. Jin and J. Zhao, Lab Chip, 2009, 9, 3118-3125.
64. E. S. Kaneshiro, M. A. Wyder, Y. P. Wu and M. T. Cushion, Journal ofMicrobiologicalMethods, 1993, 17, 1-16.

TABLE 1

Design Parameters for an embodiment of Gut-on-a-Chip described in Examples 1 and 2

| DESCRIPTOR | VALUE |
|---|---|
| Cell microchannel | |
| width × length × height | 1,000 × 10,000 × 150 μm |
| volume of the top microchannel | ~1.2 μL |
| growth surface area | 0.11 cm$^2$ |
| effective pore area | 0.021 cm$^2$ |
| porosity of a PDMS membrane | 19.5% |
| residence time of fluid (at 30 μL/h) | ~4.51 min |
| Vacuum Chamber Dimensions | |
| width × length × height$^a$ | 1,684 × 9,089 × 330 μm |
| Physiological Parameters | |
| range of volumetric flow rate | 10-100 μL/hr |
| range of shear stress$^{b,c}$ | 0.006-0.06 dyne/cm$^2$ |
| range of cyclic mechanical strain | 0-30% (in cell strain) |
| frequency of cyclic mechanical strain | 0.15 Hz |

$^a$The height of the vacuum chamber was estimated by considering the total height in the hollow area, in which the height of an upper and lower layer (150 μm) and the thickness of a porous membrane (30 μm) were all taken into account.
$^b$The range of shear stress corresponds to the range of fluid flow rate designated in this table.
$^c$Shear stress was calculated by the equation in ESI Experimental.

What is claimed herein is:

1. A method for maintaining the viability of intestinal cells and bacterial cells in co-culture comprising:
    a) providing a fluidic device having:
        a fluid channel connected to a fluid source, the fluid source supplying culture media to the fluid channel; and
        a membrane positioned within the channel between membrane support elements;
    b) introducing, to at least one surface of the membrane viable intestinal epithelial cells;
    c) pre-culturing said intestinal epithelial cells such that a layer of cells is formed that is attached to said membrane, said layer exhibiting tight junctions;
    d) introducing viable bacterial cells to produce a co-culture comprising at least a portion of the bacterial cells adhered to the intestinal epithelial cells;
    e) flowing the culture media over the co-culture at a flow rate sufficient to wash non-adherent bacterial cells out of the fluidic device; and
    f) culturing the intestinal epithelial cells and bacterial cells for at least 48 hours wherein more than 95% of the intestinal epithelial cells are viable after at least 48 hours of culture.

2. The method of claim 1, wherein the culture media is supplied at a flow rate of less than 500 μL/hr.

3. The method of claim 1, wherein the culture media is supplied at a flow rate of less than 100 μL/hr.

4. The method of claim 1, wherein the culture media is supplied at a flow rate of 50 μL/hr.

5. The method of claim 1, wherein the culture media is supplied at a flow rate of approximately 30 μL/hr.

6. The method of claim 1, wherein:
at least a portion of the membrane is flexible; and
a membrane strain mechanism capable of moving the membrane support elements is coupled to the membrane support elements; and
the method further comprises stretching the membrane along at least one dimension of the membrane during the culturing step.

7. The method of claim 6, wherein the membrane is stretched from 0% to 50%.

8. The method of claim 6, wherein the membrane is stretched from 5% to 15%.

9. The method of claim 6, wherein the membrane is stretched in a cyclic manner at a rate in the range of 0.01 Hz to 2 Hz.

10. The method of claim 6, wherein the membrane is stretched in a cyclic manner at a rate in the range of 0.05 Hz to 0.25 Hz.

11. The method of claim 6, wherein the membrane is stretched in a cyclic manner at a rate greater than 0.2 Hz to create an abnormal condition/state of the intestinal epithelial cells.

12. The method of claim 6, wherein the membrane is stretched in an irregular or intermittent manner.

13. The method of claim 1, wherein the membrane is at least partially porous.

14. The method of claim 1, wherein the membrane is coated in at least one type of attachment molecule selected from the group consisting of:
collagen; collagen type I; MATRIGEL™; extracellular matrix; laminin; proteoglycan;
vitronectin; fibronection; poly-D-lysine; polypeptides; oligonucleotides; DNA; and polysaccharide.

15. The method of claim 1, wherein the intestinal epithelial cells are selected from the group consisting of:
Caco2 cells; HT-29 cells; primary small intestine epithelial cells; primary large intestine epithelial cells; iPS cells; ESC cells; stem cells; paneth cells; crypt cells; and mucus-secreting cells.

16. The method of claim 1, wherein the bacterial cells are selected from the group consisting of:
Lactobacillus; Bacterioides; Ruminococcus; Peptococcus; Peptostreptococcus;
Bifidobacterium; Escherichia; Achromobacter; Acidaminococcus fermentans; Acinetobacter cacoaceticus; Aeromonas; Alcaligenes faecalis; Bacillus; Butyriviberio fibrosolvens; Camplyobacter; Campylobacter coli; Clostridium difficile; Clostridium sordelli; Enterobacter cloacae; Enterococcus faecalis; Enterococcus faecium; Escherichia coli; Flavobacterium; Mycobacterium; Mycoplasma; Plesiomonas shigelloides; Propionibacterium acnes; Pseudomonas aeruginosa; Ruminococcus bromii; Sarcina; Staphylococcus aureus; Streptococcus anginosus; Veillonella; Vibrio; Yersinia enterocolitica; Lactobacillus rhamnosus; Lactobacillus rhamnosus GG; Bifidobacterium breve; Bifidobacterium longum; Bifidobacterium infant's; Lactobacillus acidophilus; Lactobacillus plantarum; Lactobacillus paracasei; Lactobacillus bulgaricus; and Streptococcus thermophilus.

17. The method of claim 1, wherein the bacterial cells are aerobic.

18. The method of claim 1, wherein the bacterial cells comprise both aerobic and anaerobic bacterial cells.

19. The method of claim 1, wherein viability of said bacterial cells is evident from beta.-galactosidase activity.

20. The method of claim 1, wherein the method further comprises culturing at least one layer of endothelial cells on the opposite surface of the membrane.

21. A method for maintaining the viability of intestinal cells and bacterial cells in co-culture comprising:
a) providing a fluidic device having:
a fluid channel connected to a fluid source, the fluid source supplying culture media to the fluid channel; and
a membrane positioned within the channel between membrane support elements;
b) introducing, to at least one surface of the membrane, viable intestinal epithelial cells;
c) pre-culturing said intestinal epithelial cells such that a layer of cells is formed that is attached to said membrane, said layer exhibiting barrier function;
d) introducing viable bacterial cells to produce a co-culture comprising at least a portion of the bacterial cells adhered to the intestinal epithelial cells;
e) flowing the culture media over the co-culture at a flow rate sufficient to wash non-adherent bacterial cells out of the fluidic device; and
f) culturing the intestinal epithelial cells and bacterial cells for at least 48 hours wherein more than 95% of the intestinal epithelial cells are viable after at least 48 hours of culture.

22. The method of claim 21, wherein the culture media is supplied at a flow rate of approximately 50 μL/hr.

23. The method of claim 21, wherein the culture media is supplied at a flow rate of approximately 30 μL/hr.

24. The method of claim 21, wherein said barrier function is measured by transepithelial electrical resistance (TEER).

25. The method of claim 21, wherein the culturing the intestinal epithelial cells to produce the layer is in antibiotic-free culture medium.

26. The method of claim 21, wherein intestinal epithelial integrity is maintained or increased over said 48 hours.

27. A method for maintaining the viability of intestinal cells and bacterial cells in co-culture comprising:
a) providing a fluidic device having:
a fluid channel connected to a fluid source, the fluid source supplying culture media to the fluid channel; and
a membrane positioned within the channel between membrane support elements;
b) introducing, to at least one surface of the membrane: viable intestinal epithelial cells;
c) pre-culturing said intestinal epithelial cells such that a layer of cells is formed that is attached to said membrane, said layer comprising polarized intestinal epithelial cells;
d) introducing viable bacterial cells to produce a co-culture comprising at least a portion of the bacterial cells adhered to the intestinal epithelial cells;
e) flowing the culture media over the co-culture at a flow rate sufficient to wash non-adherent bacterial cells out of the fluidic device; and
f) culturing the intestinal epithelial cells and bacterial cells for at least 48 hours wherein more than 95% of the intestinal epithelial cells are viable after at least 48 hours of culture.

28. The method of claim 27, wherein the culture media is supplied at a flow rate of approximately 50 μL/hr.

29. The method of claim 27, wherein the culture media is supplied at a flow rate of approximately 30 μL/hr.

30. The method of claim 27, wherein said layer displays intestinal barrier integrity.

31. A method for maintaining the viability of intestinal cells and bacterial cells in co-culture comprising:
   a) providing a fluidic device having:
      a fluid channel connected to a fluid source, the fluid source supplying culture media to the fluid channel; and
      a membrane positioned within the channel between membrane support elements;
   b) introducing, to at least one surface of the membrane, viable intestinal epithelial cells;
   c) pre-culturing said intestinal epithelial cells such that a layer of cells is formed that is attached to said membrane, said layer comprising intestinal epithelial cells comprising villi structures;
   d) introducing viable bacterial cells to produce a co-culture comprising at least a portion of the bacterial cells adhered to the intestinal epithelial cells;
   e) flowing the culture media over the co-culture at a flow rate sufficient to wash non-adherent bacterial cells out of the fluidic device; and
   f) culturing the intestinal epithelial cells and bacterial cells for at least 48 hours wherein more than 95% of the intestinal epithelial cells are viable after at least 48 hours of culture.

32. The method of claim 31, wherein the culture media is supplied at a flow rate of approximately 50 μL/hr.

33. The method of claim 31, wherein the culture media is supplied at a flow rate of approximately 30 μL/hr.

34. The method of claim 31, wherein said layer displays intestinal barrier integrity.

* * * * *

UNITED STATES PATENT AND TRADEMARK OFFICE
CERTIFICATE OF CORRECTION

PATENT NO. : 10,472,612 B2  
APPLICATION NO. : 15/388171  
DATED : November 12, 2019  
INVENTOR(S) : Donald E. Ingber and Hyun Jung Kim Page 1 of 1

It is certified that error appears in the above-identified patent and that said Letters Patent is hereby corrected as shown below:

In the Claims

At Column 51, Claim 16, Line 63, "infant's;" should be replaced with -- infantis; --.

Signed and Sealed this  
Seventh Day of January, 2020

Andrei Iancu  
*Director of the United States Patent and Trademark Office*